United States Patent
Laffont et al.

(10) Patent No.: US 10,646,484 B2
(45) Date of Patent: May 12, 2020

(54) METHODS TO TREAT OPIOID USE DISORDER

(71) Applicant: Indivior UK Limited, Slough, Berkshire (GB)

(72) Inventors: Celine M. Laffont, Richmond, VA (US); Malcolm A. Young, Richmond, VA (US); Norma L. Fox, Richmond, VA (US); Barbara R. Haight, Richmond, VA (US); Susan M. Learned, Richmond, VA (US)

(73) Assignee: INDIVIOR UK LIMITED, Hull (GB)

(*) Notice: Subject to any disclaimer, the term of this patent is extended or adjusted under 35 U.S.C. 154(b) by 0 days.

(21) Appl. No.: 16/016,250

(22) Filed: Jun. 22, 2018

(65) Prior Publication Data

US 2018/0360821 A1 Dec. 20, 2018

Related U.S. Application Data

(63) Continuation of application No. PCT/US2018/037921, filed on Jun. 15, 2018.

(60) Provisional application No. 62/680,935, filed on Jun. 5, 2018, provisional application No. 62/656,216, filed on Apr. 11, 2018, provisional application No. 62/632,995, filed on Feb. 20, 2018, provisional application No. 62/598,338, filed on Dec. 13, 2017, provisional application No. 62/572,996, filed on Oct. 16, 2017, provisional application No. 62/572,331, filed on Oct. 13, 2017, provisional application No. 62/521,121, filed on Jun. 16, 2017.

(51) Int. Cl.
| | |
|---|---|
| *A61K 31/485* | (2006.01) |
| *A61K 9/00* | (2006.01) |
| *A61P 25/36* | (2006.01) |
| *A61K 47/22* | (2006.01) |
| *A61K 47/34* | (2017.01) |

(52) U.S. Cl.
CPC .......... *A61K 31/485* (2013.01); *A61K 9/0019* (2013.01); *A61K 9/0024* (2013.01); *A61K 47/22* (2013.01); *A61K 47/34* (2013.01); *A61P 25/36* (2018.01)

(58) Field of Classification Search
CPC ...... A61K 31/485; A61K 47/22; A61K 47/34; A61K 9/0019; A61K 9/0024; A61P 25/36
See application file for complete search history.

(56) References Cited

U.S. PATENT DOCUMENTS

| | | |
|---|---|---|
| 4,599,354 A | 7/1986 | Shulman |
| 4,804,663 A | 2/1989 | Kennis et al. |
| 4,938,763 A | 7/1990 | Dunn et al. |
| 5,324,519 A | 6/1994 | Dunn et al. |
| 5,346,903 A | 9/1994 | Ackerman et al. |
| 5,453,425 A | 9/1995 | Francois et al. |
| 5,486,362 A | 1/1996 | Kitchell et al. |
| 5,616,587 A | 4/1997 | Francois et al. |
| 5,648,093 A | 7/1997 | Gole et al. |
| 5,688,801 A | 11/1997 | Mesens et al. |
| 5,702,716 A | 12/1997 | Dunn et al. |
| 5,744,153 A | 4/1998 | Yewey et al. |
| 5,770,231 A | 6/1998 | Mesens et al. |
| 5,792,477 A | 8/1998 | Rickey |
| 5,990,194 A | 11/1999 | Dunn et al. |
| 6,224,905 B1 | 5/2001 | Lawrence et al. |
| 6,261,583 B1 | 7/2001 | Dunn et al. |
| 6,264,987 B1 | 7/2001 | Wright et al. |
| 6,528,080 B2 | 3/2003 | Dunn et al. |
| 6,565,874 B1 | 5/2003 | Dunn et al. |
| 6,596,316 B2 | 7/2003 | Lyons et al. |
| 6,630,155 B1 | 10/2003 | Chandrashekar et al. |
| 7,041,320 B1 | 5/2006 | Nuwayser |
| 7,824,700 B2 | 11/2010 | Cleland et al. |
| 8,173,148 B2 | 5/2012 | Dadey et al. |
| 8,221,778 B2 | 7/2012 | Siegel et al. |
| 8,236,292 B2 | 8/2012 | Thuresson et al. |
| 8,236,755 B2 | 8/2012 | Thuresson et al. |
| 8,313,763 B2 | 11/2012 | Margaron et al. |
| 8,324,343 B2 | 12/2012 | Moore et al. |
| 8,329,203 B2 | 12/2012 | Siegel et al. |
| 8,475,832 B2 | 7/2013 | Myers et al. |
| 8,501,216 B2 | 8/2013 | Cleland et al. |
| 8,545,832 B2 | 10/2013 | Thuresson et al. |
| 8,852,638 B2 | 10/2014 | Luk et al. |
| 8,921,387 B2 | 12/2014 | Norton et al. |
| 8,975,270 B2 | 3/2015 | Norton et al. |
| 9,044,450 B2 | 6/2015 | Luk et al. |
| 9,272,044 B2 | 3/2016 | Norton et al. |

(Continued)

FOREIGN PATENT DOCUMENTS

| | | |
|---|---|---|
| GB | 784659 A | 10/1957 |
| WO | WO-91/19474 A1 | 12/1991 |

(Continued)

OTHER PUBLICATIONS

Thaxter et al. (Indivior, http://www.indivior.com/investor-news/rbp-6000-phase-3-top-line-results/, May 2016). (Year: 2016).*

(Continued)

*Primary Examiner* — Umamaheswari Ramachandran

(74) *Attorney, Agent, or Firm* — Edward D. Grieff; Mintz, Levin, Cohn, Ferris, Glovsky and Popeo, P.C.

(57) ABSTRACT

The disclosure provides sustained-release buprenorphine formulations that produce therapeutic plasma concentration levels of buprenorphine in patients to treat opioid use disorder.

29 Claims, 13 Drawing Sheets

(56) References Cited

U.S. PATENT DOCUMENTS

| | | |
|---|---|---|
| 9,295,645 B2 | 3/2016 | Norton et al. |
| 9,498,432 B2 | 11/2016 | Norton et al. |
| 9,782,402 B2 | 10/2017 | Norton et al. |
| 2003/0004100 A1 | 1/2003 | Dasch et al. |
| 2003/0211157 A1 | 11/2003 | Simon |
| 2004/0018238 A1 | 1/2004 | Shukla |
| 2004/0033250 A1 | 2/2004 | Patel et al. |
| 2004/0101557 A1 | 5/2004 | Gibson et al. |
| 2004/0151670 A1 | 8/2004 | Blondino et al. |
| 2005/0032781 A1 | 2/2005 | Ehrich |
| 2005/0048115 A1 | 3/2005 | Mangena et al. |
| 2005/0048123 A1 | 3/2005 | Su et al. |
| 2005/0079202 A1 | 4/2005 | Chen et al. |
| 2005/0106214 A1 | 5/2005 | Chen |
| 2006/0002979 A1 | 1/2006 | Ashammakhi et al. |
| 2006/0210604 A1 | 9/2006 | Dadey et al. |
| 2007/0077304 A1 | 4/2007 | Luk et al. |
| 2007/0117828 A1 | 5/2007 | Simmons et al. |
| 2007/0265190 A1 | 11/2007 | Thuresson et al. |
| 2008/0299168 A1 | 12/2008 | Dadey et al. |
| 2009/0061011 A1 | 3/2009 | Talton |
| 2009/0092650 A1 | 4/2009 | Warren et al. |
| 2010/0266655 A1 | 10/2010 | Dadey |
| 2010/0292195 A1 | 11/2010 | Dadey et al. |
| 2013/0071477 A1 | 3/2013 | Fischer |
| 2013/0190341 A1 | 7/2013 | Tiberg et al. |
| 2013/0202658 A1 | 8/2013 | Norton et al. |
| 2013/0203796 A1 | 8/2013 | Norton et al. |
| 2013/0210853 A1 | 8/2013 | Norton et al. |
| 2014/0193347 A1 | 7/2014 | Thuresson et al. |
| 2015/0064118 A1 | 3/2015 | Thuresson et al. |
| 2015/0182522 A1 | 7/2015 | Tiberg et al. |
| 2015/0231258 A1 | 8/2015 | Luk et al. |
| 2016/0128997 A1 | 5/2016 | Nasser |
| 2017/0079976 A1 | 3/2017 | Norton et al. |
| 2017/0281618 A1 | 10/2017 | Norton et al. |
| 2017/0354653 A1 | 12/2017 | Nasser |
| 2018/0243292 A1 | 8/2018 | Nasser |

FOREIGN PATENT DOCUMENTS

| | | | |
|---|---|---|---|
| WO | WO-95/27481 A1 | 10/1995 | |
| WO | WO-00/06117 A1 | 2/2000 | |
| WO | WO-00/024374 A1 | 5/2000 | |
| WO | WO-01/15699 A1 | 3/2001 | |
| WO | WO-01/35929 A2 | 5/2001 | |
| WO | WO-01/35929 A3 | 5/2001 | |
| WO | WO-02/30393 A2 | 4/2002 | |
| WO | WO-2003/041684 A2 | 5/2003 | |
| WO | WO-2003/041684 A3 | 5/2003 | |
| WO | WO-2004/043432 A2 | 5/2004 | |
| WO | WO-2004/043432 A3 | 5/2004 | |
| WO | WO-2004/081196 A2 | 9/2004 | |
| WO | WO-2004/081196 A3 | 9/2004 | |
| WO | WO-2005/048989 A1 | 6/2005 | |
| WO | WO-2006/041942 A2 | 4/2006 | |
| WO | WO-2006/041942 A3 | 4/2006 | |
| WO | WO-2006/053175 A2 | 5/2006 | |
| WO | WO-2006-053175 A3 | 5/2006 | |
| WO | WO-2007/041410 A2 | 4/2007 | |
| WO | WO-2007/041410 A3 | 4/2007 | |
| WO | WO-2007/061828 A2 | 5/2007 | |
| WO | WO-2007/061828 A3 | 5/2007 | |
| WO | WO-2007/103185 A2 | 9/2007 | |
| WO | WO-2007/103185 A3 | 9/2007 | |
| WO | WO-02/30393 A3 | 4/2008 | |
| WO | WO-2008/045516 A1 | 4/2008 | |
| WO | WO-2008/100532 A1 | 8/2008 | |
| WO | WO-2008/153611 A2 | 12/2008 | |
| WO | WO-2008/153611 A3 | 12/2008 | |
| WO | WO-2009/091737 A2 | 7/2009 | |
| WO | WO-2009/091737 A3 | 7/2009 | |
| WO | WO-2011/154724 A2 | 12/2011 | |
| WO | WO-2011/154724 A3 | 12/2011 | |
| WO | WO-2011/154724 A9 | 12/2011 | |
| WO | WO-2011/154725 A2 | 12/2011 | |
| WO | WO-2011/154725 A3 | 12/2011 | |
| WO | WO-2014/016428 A1 | 1/2014 | |
| WO | WO-2014/144241 A1 | 9/2014 | |
| WO | WO-2015/136253 A1 | 9/2015 | |
| WO | WO-2016/102683 A1 | 3/2016 | |
| WO | WO-2016/066655 A1 | 5/2016 | |
| WO | WO-2016/071767 A1 | 5/2016 | |
| WO | WO-2017/046384 A1 | 3/2017 | |

OTHER PUBLICATIONS

Nasser et al. (J Clin Psychopharmacol, Feb. 2016, 36(1), p. 1-19) (Year: 2016).*

Laffont et al. (Applicants' cited IDS: The J of Clin. Pharmacology, 2016, p. 806-815). (Year: 2016).*

Aird, J. (Apr. 2003). Controlled Release—SMi Conference. Feb. 12-13, 2003, London,UK, *IDrugs* 6(4):334-336.

Amass, L. et al. (Jan. 2012, e-published Oct. 12, 2011). "A prospective, randomized, multicenter acceptability and safety study of direct buprenorphine/naloxone induction in heroin-dependent individuals," *Addiction* 107(1):142-151.

Astaneh, R. et al. (Jan. 2009). "Changes in morphology of in situ forming PLGA implant prepared by different polymer molecular weight and its effect on release behavior," J Pharm Sci 98(1):134-145.

Baker, D.L. et al. (Oct. 2004). "Gonadotropin-releasing hormone agonist: a new approach to reversible contraception in female deer," *J Wildl Dis* 40(4):713-724.

Bartsch, W. et al. (1976). "Acute Toxicity in Various Solvents in the Mouse and Rat," *Arzneim-Forsch, Drug Res* 26:1581-1583.

Basu, S.K. et al. (Mar. 2004). "Protein crystals for the delivery of biopharmaceuticals," *Expert Opin Biol Ther* 4(3):301-317.

Becci, P.J. et al. (1983). "Subchronic feeding study in beagle dogs of N-methylpyrrolidone," *J Appl Toxicol* 3(2):83-86.

Berges, R. et al. (2005). "Eligard®: Pharmacokinetics, effect on Testosterone and PSA Levels and Tolerability," *European Urology Supplements* 4:20-25.

Bickel WK, et al. Buprenorphine: dose-related blockade of opioid challenge effects in opioid dependent humans. J Pharmacol Exp Ther. 1988; 247:47-53.

Bickel, W.K. et al. (1995). "Buprenorphine Treatment of Opioid Dependence: A Review," Experimental and Clinical Psychopharmacology 3(4):477-489.

Boongird, A. et al. (Jan. 2011). "Biocompatibility study of glycofurol in rat brains," *Exp Biol Med* 236(1):77-83.

Bowersock, T.L. et al. (1999). "Vaccine delivery to animals," *Adv Drug Deliv Rev* 38(2):167-194.

Bromberg, L.E. et al. (Jul. 31, 2000). "Sustained release of silver from periodontal wafers for treatment of periodontitis," *J Control Release* 68(1):63-72.

Chandrashekar, B.L. et al. (Jul. 1999). "Sustained Release of Leuprolide Acetate from an In-situ Forming Biodegradable Polymeric Implant as the Delivery Vehicle," *Proceed Int'l Symp Control Rel Bioact Mater* 26, 3 pages.

Chen, F.A. et al. (Jul. 2003). "Biodegradable polymer-mediated intratumoral delivery of cisplatin for treatment of human head and neck squamous cell carcinoma in a chimeric mouse model," *Head Neck* 25(7):554-560.

Chu, F.M. et al. (Sep. 2002). "A clinical study of 22.5 mg. La-2550: A new subcutaneous depot delivery system for leuprolide acetate for the treatment of prostate cancer," *Journal of Urology* 168(3):1199-1203.

Comer S, et al, Buprenorphine sublingual tablets: effects on IV heroin self-administration by humans, Psychopharmacology, vol. 154, pp. 28-37 (2001).

Comer, S.D. et al. (Oct. 2005, e-published Sep. 29, 2005). "Buprenorphine/naloxone reduces the reinforcing and subjective effects of heroin in heroin-dependent volunteers," Psychopharmacology 181(4):664-675.

(56) References Cited

OTHER PUBLICATIONS

Comer S, et al, Abuse liability of intravenous buprenorphine/naloxone and buprenorphine alone in buprenorphine-maintained intravenous heroin abusers, Addiction, vol. 105, No. 4, pp. 709-718 (2010).
Contet C, Kieffer BL, Befort K. Mu opioid receptor: a gateway to drug addiction. *Curr Opin Neurobiol* 14:370-378, 2004.
Coonts, B.A. et al. (Oct. 1993). "Plasma Concentrations of Naltrexone Base Following Subcutaneous and Intramuscluar Injections of Atrigel™ Formulations in Dogs," *Pharmaceutical Research: Official Journal of the American Association of Pharmaceutical Scientists* PHREEB 10(10):PDD 7071, 2 pages.
Correia CJ, et al. Effects associated with double-blind omission of buprenorphine/naloxone over a 98-h period. Psychopharmacology (Berl). 2006; 189:297-306.
Cox, M.C. et al. (Aug. 2005). "Leuprolide acetate given by a subcutaneous extended-release injection: less of a pain?" *Expert Rev Anticancer Ther* 5(4):605-611.
Crawford, E.D. et al. (Feb. 2006). "A 12-month clinical study of LA-2585 (45.0 mg): a new 6-month subcutaneous delivery system for leuprolide acetate for the treatment of prostate cancer," *Journal of Urology* 175(2):533-536.
Crist, R.C. et al. (Sep. 2013, e-published Apr. 23, 2013). "An intronic variant in OPRD1 predicts treatment outcome for opioid dependence in African-Americans," *Neuropsychopharmacology* 38(10):2003-2010.
Dadey, E.J. (2008). The Atrigel Drug Delivery System. In: Rathbone et al Eds, Modified-Release Drug Delivery Technology, $2^{nd}$ Ed., New York, pp. 183-190.
Dernell, W.S. et al. (1998). "Apparent interaction of dimethyl sulfoxide with cisplatin released from polymer delivery devices injected subcutaneously in dogs," *J Drug Target* 5(5):391-396.
Domb, A.J. et al. (1989). "Solid-State and Solution Stability of Poly(anhydrides) and Poly(esters)," *Macromolecules* 22(5):2117-2122.
Dunn, R.S., (2003). "The Atrigel Drug Delivery System," *Modified-Release Drug Delivery Technology*, Edited by Rathbone, Hadgraft, Roberts, Marcel Dekker, Inc., Chapter 54, pp. 647-655.
Dunn, R.L. et al (1996). "Sustained Release of Cisplatin in Dogs from an Injectable Implant Delivery System," *Journal of Bioactive and Compatible Polymers*, 11:286-300.
Duysen, E.G. et al (1992). "Bioactivity of Polypeptide Growth Factors Released from the ATRIGEL Drug Delivery System," *PHREED*, 9(10):573, Abstract No. 2028.
Duysen, E.G. et al (1993). "Release of Bioactive Growth Factors from the ATRIGEL Delivery System in Tibial Defect and Dermal Wound Models," *PHREEB*, 10(10):S83, Abstract No. 2043.
Duysen, E.G. et al (1994). "An Injectable, Biodegradable Delivery System for Antineoplastic Agents," *PHREED*, 11(10):588, Abstract No. 2071.
Eliaz, R.E. et al. (Dec. 2000). "Delivery of soluble tumor necrosis factor receptor from in-situ forming PLGA implants: in-vivo," *Pharm Research* 17(12):1546-1550.
Erickson, N.M. et al. (2001). "An in Vitro Degradation Study Comparing Poly (DL-Lactide-Co-Glycolide) with Acid End Groups and Ester End Groups," $20^{th}$ Southern Biomedical Engineering Conference, 1 page.
Evans, H.C., et al (2004). "Leuprorelin: Subcutaneous Depot Formulation (ELIGARD) for Advanced Prostate Cancer," *Am J. Cancer*, 3(3):197-201.
FDA Document K982865 (1998). Atrix Laboratories, Inc. 13 pages.
FDA Document K994137 (2000). Atrix Laboratories, Inc. 9 pages.
Frank, K.R. et al (1994). "Controlled Release of Bioactive Growth Factors from a Biodegradable Delivery System," PHREEB, 11(10):S88, Abstract No. 2070.
Frost, J.J., Wagner, H.N. Jr., Dannals, R.F., Ravert, H.T., Links, J.M., Wilson, A.A., Burns, H.D., Wong, D.F., McPherson, R.W., Rosenbaum, A.E., Kuhar, M.J. & Snyder, S.H. (1985). Imaging opiate receptors in the human brain by positron tomography. *J Comp Assist Tomogr*, 9, 231-236.

Fudala, P.J. et al. (Sep. 4, 2003). "Office-based treatment of opiate addiction with a sublingual-tablet formulation of buprenorphine and naloxone," N Engl J Med 349(10):949-958.
Gerentes, P. et al. (2002). "Study of a chitin-based gel as injectable material in periodontal surgery," *Biomaterials* 23(5):1295-1302.
Gerstein, D.R. et al. (Sep. 20, 1990). "Treating drug problems," *N Engl J Med* 323(12):844-848.
Graves, R.A. et al. (Aug. 3, 2007). "In vitro dissolution method for evaluation of buprenorphine in situ gel formulation: a technical," *AAPS PharmSciTech* 8(3): Article 62, El-E4.
Greenwald MK, et al. Effects of buprenorphine sublingual tablet maintenance on opioid drug-seeking behavior by humans. Psychopharmacology (Berl). 2002; 160:344-352.
Greenwald, M.K. et al. (Nov. 2003). "Effects of buprenorphine maintenance dose on mu-opioid receptor availability, plasma concentrations, and antagonist blockade in heroin-dependent volunteers," Neuropsychopharmacology 28(11):2000-2009.
Greenwald, M. et al. (Jan. 1, 2007, e-published Sep. 1, 2006). "Buprenorphine duration of action: mu-opioid receptor availability and pharmacokinetic and behavioral indices," Biol Psychiatry 61(1):101-110.
Greenwald MK, et al. Sustained release d-amphetamine reduces cocaine but not 'speedball'-seeking in buprenorphine-maintained volunteers: a test of dual-agonist pharmacotherapy for cocaine/heroin polydrug abusers. Neuropsychopharmacology. 2010; 35:2624-2637.
Greenwald, M.K. et al. (Nov. 1, 2014, e-published Aug. 19, 2014). "Buprenorphine maintenance and mu-opioid receptor availability in the treatment of opioid use disorder: implications for clinical use and policy," Drug Alcohol Depend 144:1-11.
Griffeth, R.J. et al. (2002). "Is Lucteal Production of $PGF_2\alpha$ Required for Luteolysis?" *Biology of Reproduction* 66(Supplement 1), Abstract 465, 2 pages.
Hempel, G. et al. (May 1, 2007). "Cytotoxicity of dimethylacetamide and pharmacokinetics in children receiving intravenous busulfan," *J Clin Oncol* 25(13)1772-1778.
Henriksen, G. et al. (May 2008, e-published Nov. 29, 2007). "Imaging of opioid receptors in the central nervous system," Brain 131(Pt. 5):1171-1196.
Hillhouse, M. et al. (Sep. 2011). "Participant characteristics and buprenorphine dose," *Am J Drug Alcohol Abuse* 37(5):453-459.
Hoffman, K. et al. (May/Jun. 2017). "Safety of a Rapidly Dissolving Buprenorphine/Naloxone Sublingual Tablet (BNX-RDT) for Treatment of Opioid Dependence: A Multicenter, Open-label Extension Study," *J Addict Med* 11(3):217-223.
Hser, Y. et al. (Jan. 2014, e-published Oct. 9, 2013). "Treatment retention among patients randomized to buprenorphine/naloxone compared to methadone in a multi-site trial," *Addiction* 109(1):79-87.
International Search Report dated Jun. 11, 2015, for PCT Application No. PCT/GB2015/050676, filed on Mar. 9, 2015, 6 pages.
International Search Report dated Mar. 24, 2016 for PCT Application No. PCT/IB2015/002269, filed on Nov. 6, 2015, 5 pages.
Jain, R.A. (Dec. 2000). "The manufacturing techniques of various drug loaded biodegradable poly(lactide-co-glycolide) (PLGA) devices," Biomaterials 21(23):2475-2490.
Jarr, E.M. et al. (Jul. 1999). "Sustained Release of Lidocaine from an Injectable Implant System for Treatmenr of Post-Operative," *Proceedings Int'l Symp Control Rel Bioact Materials* Abstract #5423, 4 pages.
Johnson, O.L. et al. (Jun. 1997). "The stabilization and encapsulation of human growth hormone into biodegradable microspheres," Pharm res 14(6):730-735.
Kaul, S. et al. (Feb. 2000). "Polymeric-based perivascular delivery of a nitric oxide donor inhibits intimal thickening after balloon denudation arterial injury: role of nuclear factor-kappaB," *J Am Coll Cardiol* 35(2):493-501.
Kissel, T. (Jan. 2002). "ABA-triblock copolymers from biodegradable polyester A-blocks and hydrophilic poly(ethylene oxide) B-blocks as a candidate for in situ forming hydrogel delivery systems for proteins," *Adv Drug Deliv Rev* 54(1):99-134.

(56) References Cited

OTHER PUBLICATIONS

Kuhlman, J.J. et al. (Apr. 1998). "Relationship of plasma buprenorphine and norbuprenorphine to withdrawal symptoms during dose induction, maintenance and withdrawal from sublingual buprenorphine," Addiction 93(4):549-559.

Kranz, H. et al. (Jan. 5, 2001). "Myotoxicity studies of injectable biodegradable in-situ forming drug delivery systems," *Int J Pharm* 212(1):11-18.

Laffont, C.M. et al. (Jul. 2016, e-published Mar. 11 2016). "Population Pharmacokinetic Modeling After Repeated Administrations of RBP-6000, a New, Subcutaneously Injectable, Long-Acting, Sustained-Release Formulation of Buprenorphine, for the Treatment of Opioid Use Disorder," *J Clin Pharmacol* 56(7):806-815.

Lee, K.P. et al. (Aug. 1987). "Toxicity of N-methyl-2-pyrrolidone (NMP): teratogenic, subchronic, and two-year inhalation studies," *Fundam Appl Toxicol* 9(2):222-235.

Lester PA, Traynor JR. Comparison of the in vitro efficacy of mu, delta, kappa and ORL1 receptor agonists and non-selective opioid agonists in dog brain membranes. *Brain Res*. 2006;1073-1074:290-296.

Lewis JW., Buprenorphine. Drug Alcohol Depend. 1985; 14:363-372.

Li, M. et al. (Nov. 2003). "A novel, non-prostanoid EP2 receptor-selective prostaglandin E2 agonist stimulates local bone formation and enhances fracture healing," *Bone Miner Res* 18(11):2033-2042.

Liao, C-L. et al. (2008). "In vitro skin permeation of buprenorphine transdermal patch," Journal of Food and Drug Analysis 16(6):8-15.

Lindhardt et al, "Intranasal Absorption of Buprenorphine—in vivo biovavailability study in sheep." Int. J. Pharm., 205(1-2):159-163 (2000).

Ling W, Wesson DR, Charuvastra C, Klett CJ. A controlled trial comparing buprenorphine and methadone maintenance in opioid dependence. *Arch. Gen. Psychiatry*. 1996; 53:401-407.

Ling W, Charuvastra C, Collins JF, Batki S, Brown LS, Jr, Kintaudi P, Wesson DR, McNicholas L, Tusel DJ, Malkerneker U, Renner JA, Jr, Santos E, Casadonte P, Fye C, Stine S, Wang RI, Segal D. Buprenorphine maintenance treatment of opiate dependence: a multicenter, randomized clinical trial. *Addiction*. 1998; 93:475-486.

Ling, W. et al. (Oct. 13, 2010). "Buprenorphine implants for treatment of opioid dependence: a randomized controlled trial," *JAMA* 304(14):1576-1583.

Lutfy K, Cowan A. Buprenorphine: a unique drug with complex pharmacology. *Curr. Neuropharmacol*. 2004; 2:395-402.

Lynch, G.S. et al. (November 204). "Emerging drugs for sarcopenia: age-related muscle wasting," *Expert Opin Emerg Drugs* 9(2);345-361.

Makadia, H.K. et al. (Sep. 1, 2011, e-published Aug. 26, 2011). "Poly Lactic-co-Glycolic Acid (PLGA) as Biodegradable Controlled Drug Delivery Carrier," *Polymers* 3(3):1377-1397.

Malik, K. et al. (2010). "Atrigel: A Potential Parenteral Controlled Drug Delivery System," *Der Pharmacia Sinica* 1(1):74-81.

Matschke, C. et al. (Dec. 2002). "Sustained-release injectables formed in situ and their potential use for veterinary products," *J Control Release* 85(1-3):1-15.

Matthes HW, Maldonado R, Simonin F, Valverde O, Slowe S, Kitchen I, Befort K, Dierich A, Le Meur M, Dolle P, Tzavara E, Hanoune J, Rogues BP, Kieffer BL. Loss of morphine-induced analgesia, reward effect and withdrawal symptoms in mice lacking the mu-opioid-receptor gene. *Nature* 1996; 383:819-823.

McLeod, D.G. et al. (Feb. 2003). "Hormonal therapy: historical perspective to future directions," *Urology* 61(2 Suppl 1):3-7.

Mealy (2004). "Treatment of Metabolic Disorders by Condition," Annual Update 2003/2004—*Drugs of the Future* 29(8):843-872.

Medicott, N.J. et al. (Jun. 23, 2004). "Sustained release veterinary parenteral products," *Adv Drug Deliv Rev* 56(10):1345-1365.

Miller, R.A. et al. (Sep. 1977). "Degradation rates of oral resorbable implants (polylactates and polyglycolates): rate modification with changes in PLA/PGA copolymer ratios," *Biomed Mater Res* 11(5):711-719.

Mottu, F. et al. (Apr. 2000). "In vitro assessment of new embolic liquids prepared from preformed polymers and water-miscible solvents for aneurysm treatment," *Biomaterials* 21(8):803-811.

Nasser, A.F. et al. (Aug. 2015, e-published Jan. 21, 2015). "Pharmacokinetics of Sublingual Buprenorphine and Naloxone in Subjects with Mild to Severe Hepatic Impairment (Child-Pugh Classes A, B, and C), in Hepatitis C Virus-Seropositive Subjects, and in Healthy Volunteers," Clin Pharmacokinet 54(8):837-849.

Nasser, A.F. et al. (Feb. 2016). "Sustained-Release Buprenorphine (RBP-6000) Blocks the Effects of Opioid Challenge With Hydromorphone in Subjects With Opioid Use Disorder," *J Clin Psychopharmacol* 36(1):18-26.

Packhaeuser, C.B. et al. (Sep. 2004). "In situ forming parenteral drug delivery systems: an overview," *Eur J Pharm Biopharm* 58(2):445-455.

Panaccione, C. et al. (1997). "Use of a Trinomial Distribution Probability Model in Development of a Tier-Testing Scheme for Content Uniformity Testing," *Drug Information Journal* 31:903-909.

Paralkar, V.M. et al. (May 27, 2003, e-published May 14, 2003). "An EP2 receptor-selective prostaglandin E2 agonist induces bone healing," *PNAS USA* 100(11):6736-6740.

Parent, M. et al. (Nov. 28, 2013, e-published Sep. 1, 2013). "PLGA in situ implants formed by phase inversion: critical physicochemical parameters to modulate drug release," *J Control Release* 172(1):292-304.

Patel, R.B. et al. (Nov. 1, 2010, e-published Aug. 20, 2010). "Effect of injection site on in situ implant formation and drug release in vivo," *J Control Release* 147(3):350-358.

Pechenov, S. et al. (Apr. 16, 2004). "Injectable controlled release formulations incorporating protein crystals," *J Control Release* 96(1):149-158.

Perez-Merreno, R. (Nov. 2002). "A six-month, open-label study assessing a new formulation of leuprolide 7.5 mg for suppression of testosterone in patients with prostate cancer," *Clinical Therapuetics* 24(11):1902-1914.

Perez-Marrero, R. et al. (Feb. 2004). "A subcutaneous delivery system for the extended release of leuprolide acetate for the treatment of prostate cancer," *Expert Opin Pharmacother* 5(2):447-457.

Radomsky, M.L. et al. (1993). "The Controlled Release of Ganirelix from the Atrigel™ Injectable Implant System," Proceed Intern *Symp Control Rel Bioact Mater* 20:458-459.

Rathbone, M.J. et al. (Aug. 1, 2002). "Modified release drug delivery in veterinary medicine," *Drug Discov Today* 7(15):823-829.

Ravivarapu, H.B. et al. (Feb. 28, 2000). "Sustained activity and release of leuprolide acetate from an in situ forming polymeric implant," *AAPS PharmSciTech* 1(1):E1.

Ravivarapu, H.B. et al. (Jun. 2000). "Sustained suppression of pituitary-gonadal axis with an injectable, in situ forming implant of leuprolide acetate," *J Pharm Sci* 89(6):732-741.

Ravivarapu, H.B. et al. (Jan. 25, 2000). "Parameters affecting the efficacy of a sustained release polymeric implant of leuprolide," *Int J Pharm* 194(2):181-191.

Rosen MI, et al. Buprenorphine: duration of blockade of effects of intramuscular hydromorphone. Drug Alcohol Depend. 1994; 35:141-149.

Rosenthal, R.N. et al. (Dec. 2013, e-published Sep. 18, 2013). "Buprenorphine implants for treatment of opioid dependence: randomized comparison to placebo and sublingual buprenorphine/naloxone," Addiction 108(12):2141-2149.

Sacerdote, P. (2006). "Opioids and the immune system," Palliat Med 20 Suppl 1 s9-15.

Schoenhammer, K. et al. (Apr. 17, 2009, e-published Dec. 24, 2008). "Injectable in situ forming depot systems: PEG-DAE as novel solvent for improved PLGA storage stability," *Int J. Pharm* 371(1-2):33-39.

Schoenhammer, K. et al. (Dec. 2009, e-published Oct. 1, 2009). "Poly(ethyleneglycol) 500 dimethylether as novel solvent for injectable in situ forming depots," *Pharm Res* 26(12):2568-2577.

Schulman, C.C. (2005). "LHRH Agonists in Prostate Cancer Optimising Testosterone Control with Eligard®," *European Urology Supplements* 4:1-3.

(56) References Cited

OTHER PUBLICATIONS

Schwach-Abdellaoui, K. et al. (Jul. 2000). "Local delivery of antimicrobial agents for the treatment of periodontal diseases," *Eur J Pharm Biopharm* 50(1):83-99.

Sherman, J.M. et al. (1994). "Localized Delivery of Bupivacaine HCL from Astrigel™ Formulations for the Management of Postoperative Pain," *Pharmaceutical Research* 11(10), PDD7574, 2 pages.

Sigmon et al, "An injection depot formulation of buprenorphine: extended biodelivery and effects," Addiction, 101:420-432 (2006).

Sigmon SC, et al.. Evaluation of an injection depot formulation of buprenorphine: placebo comparison. Addiction. 2004; 99:1439-1449.

Sinha, V.R. et al. (Jun. 18, 2004). "Poly-epsilon-caprolactone microspheres and nanospheres: an overview," *Int J. Pharm* 278(1):1-23.

Smith, R.W. et al. (2004). "A Study of Water Diffusion, in Both Radial and Axial Directions, into Biodegradable Monolithic Depots Using Ion Beam Analysis," *Polymer* 45:4893-4908.

Sobel et al, "Open-label trial of an injection depot formulation of buprenorphine in opioid detoxification," Drug and Alcohol Dependence, 73:11-22 (2004).

Southard, G.L. et al. (Feb. 1998). "Subgingival controlled release of antimicrobial agents in the treatment of periodontal disease," *Int J Antimicrob Agents* 9(4):239-253.

Southard, G.L. et al. (Sep. 1998). "The drug delivery and biomaterial attributes of the ATRIGEL® technology in the treatment of periodontal disease," *Expert Opin Investig Drugs* 7(9):1483-1491.

Strain et al, "Blockade of hydromorphone effects by buprenorphine/naloxone and buprenorphine," Psychopharmacology, vol. 159, pp. 161-166 (2002).

Sundaram, S. et al. (2004). "Peptides: Nasal and Pulmonary Delivery of Deslorelin, a Peptide Drug," *American Pharmaceutical Review* 130-139.

Swanson, B.N. (Jan.-Jun. 1985). "Medical use of dimethyl sulfoxide (DMSO)," *Rev Clin Basic Pharm* 5(1-2):1-33.

Tipton, A.J. et al. (Oct. 1991). "A Biodegradable, Injectable Delivery System for NonSteroidal Anti-Flammatory Drugs," *Pharmaceutical Research* 8(10), PDD 7279, 2 pages.

Titeler, M., Lyon, R.A., Kuhar, M.J., Frost, J.J., Dannals, R.F., Leonhardt, S., Bullock, A., Rydelek, L.T., Price, D.L. & Struble, R.G. (1989). Mu opiate receptors are selectively labeled by [3H]-carfentanil in human and rat brain. *Eur J Pharmacol*, 167, 221-228.

Tkacz, J. et al. (Jan.-Feb. 2012, e-published Nov. 18, 2011). "Compliance with buprenorphine medication-assisted treatment and relapse to opioid use," Am J Addict 21(1):55-62.

Tserki, V. et al. (Feb. 2006). "Biodegradable aliphatic polyesters. Part II. Synthesis and characterization of chain extended poly(butylene succinate-co-butylene adipate)," *Polymer Degradation and Stability* 91(2):377-384.

Tunn, U.W. (Jul. 29, 2011). "A 6-month depot formulation of leuprolide acetate is safe and effective in daily clinical practice: a non-interventional prospective study in 1273 patients," *BMC Urology* 11:15.

Veilleux JC, Colvin PJ, Anderson J, York C, Heinz AJ. A review of opioid dependence treatment: pharmacological and psychosocial interventions to treat opioid addiction. Clin Psychol Rev 2010; 30: 155-166.

Walsh SL, et al. Clinical pharmacology of buprenorphine: ceiling effects at high doses. Clin Pharm Ther. 1994; 55:569-580.

Walsh SL, et al. Acute administration of buprenorphine in humans: partial agonist and blockade effects. J Pharmacol Exp Ther. 1995; 274:361-372.

Wang, L. et al. (Jul. 31, 2003). "Structure formation in injectable poly(lactide-co-glycolide) depots," *J Control Release* 90(3):345-354.

Wang, L. et al. (Sep. 30, 2004). "Drug release from injectable depots: two different in vitro mechanisms," J Control Release 99(2):207-216.

Wiens, B.L. et al. (Nov. 2013). "Missing Data in Noninferiority Trials," *Stat Biopharm* 5(4):383-393.

Winzenburg, G. et al. (Jun. 23, 2004). "Biodegradable polymers and their potential use in parenteral veterinary drug delivery systems," *Adv Drug Deliv Rev* 56(10):1453-1466.

Wolff, E.D. et al. (1994). "Use of Bio-Beads SM-4 Adsorbent for Bioburden Testing of Atrigel™ Biodegradable Delivery System Containing 10% Doxycycline," ASM Las Vegas 1994, Abstracts, 3 pages.

World Health Organization (2001). N-Methyl-2-Pyrrolidone, Concise International Chemical Assessment Document 35, 39 pages.

Written Opinion dated Jun. 11, 2015, for PCT Application No. PCT/GB2015/050676, filed on Mar. 9, 2015, 6 pages.

Written Opinion dated Mar. 24, 2016 for PCT Application No. PCT/IB2015/002269, filed on Nov. 6, 2015, 10 pages.

Xia, Y. et al. (Jul. 18, 2002). "Uniform biodegradable microparticle systems for controlled release," *J Control Release* 82(1):137-147.

Zhu, G. et al. (2000). "Stabilization of proteins encapsulated in cylindrical poly(lactide-co-glycolide) implants: mechanism of stabilization by basic additives," *Pharm Res* 17(3):351-357.

Zubieta, J-K et al. (Sep. 2000). "Buprenorphine-induced changes in mu-opioid receptor availability in male heroin-dependent volunteers: a preliminary study," Neuropsychopharmacology 23(3):326-334.

https://clinicaltrials.gov/archive/NCT01738503/2012_11_29 (Reckitt Benckiser Pharmaceuticals, Inc., An Open-Label, Multicenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects, ClinicalTrials.Gov, Identifier: NCT01738503, Nov. 29, 2012).

https://clinicaltrials.gov/archive/NCT01738503/2013_07_29 (Reckitt Benckiser Pharmaceuticals, Inc., An Open-Label, Multicenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects, ClinicalTrials.Gov, Identifier: NCT01738503, Jul. 29, 2013).

https://clinicaltrials.gov/archive/NCT01738503/2014_01_15 (Reckitt Benckiser Pharmaceuticals, Inc., An Open-Label, Multicenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects, ClinicalTrials.Gov, Identifier: NCT01738503, Jan. 15, 2014).

https://clinicaltrials.gov/archive/NCT01738503/2014_09_28 (Reckitt Benckiser Pharmaceuticals, Inc., An Open-Label, Multicenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects, ClinicalTrials.Gov, Identifier: NCT01738503, Sep. 28, 2014).

https://clinicaltrials.gov/archive/NCT01738503/2015_06_03 (Reckitt Benckiser Pharmaceuticals, Inc., An Open-Label, Multicenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects, ClinicalTrials.Gov, Identifier: NCT01738503, Jun. 3, 2015).

https://clinicaltrials.gov/archive/NCT01738503/2015_08_06 (Reckitt Benckiser Pharmaceuticals, Inc., An Open-Label, Multicenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects, ClinicalTrials.Gov, Identifier: NCT01738503, Aug. 6, 2015).

https://clinicaltrials.gov/archive/NCT02044094/2014_01_22 (Reckitt Benckiser Pharmaceuticals, Inc., A Multiple-Dose Study of Blockade of Subjective Opioid Effects, Plasma Levels, and Safety of Subcutaneous Injections of Depot Buprenorphine (RBP-6000) in Subjects With Opioid Use Disorder, ClinicalTrials.Gov, Identifier: NCT02044094, Jan. 22, 2014).

https://clinicaltrials.gov/archive/NCT02044094/2014_01_27 (Reckitt Benckiser Pharmaceuticals, Inc., A Multiple-Dose Study of Blockade of Subjective Opioid Effects, Plasma Levels, and Safety of Subcutaneous Injections of Depot Buprenorphine (RBP-6000) in Subjects With Opioid Use Disorder, ClinicalTrials.Gov, Identifier: NCT02044094, Jan. 27, 2014).

(56) References Cited

OTHER PUBLICATIONS https://clinicaltrials.gov/archive/NCT02044094/2014_09_28 (Reckitt Benckiser Pharmaceuticals, Inc., A Multiple-Dose Study of Blockade of Subjective Opioid Effects, Plasma Levels, and Safety of Subcutaneous Injections of Depot Buprenorphine (RBP-6000) in Subjects With Opioid Use Disorder, ClinicalTrials.Gov, Identifier: NCT02044094, Sep. 28, 2014).
https://clinicaltrials.gov/archive/NCT02044094/2015_02_17 (Reckitt Benckiser Pharmaceuticals, Inc., A Multiple-Dose Study of Blockade of Subjective Opioid Effects, Plasma Levels, and Safety of Subcutaneous Injections of Depot Buprenorphine (RBP-6000) in Subjects With Opioid Use Disorder, ClinicalTrials.Gov, Identifier: NCT02044094, Feb. 17, 2015).
https://clinicaltrials.gov/archive/NCT02044094/2015_08_21 (Reckitt Benckiser Pharmaceuticals, Inc., A Multiple-Dose Study of Blockade of Subjective Opioid Effects, Plasma Levels, and Safety of Subcutaneous Injections of Depot Buprenorphine (RBP-6000) in Subjects With Opioid Use Disorder, ClinicalTrials.Gov, Identifier: NCT02044094, Aug. 21, 2015).
Anon (Nov. 1, 2017). "Highlights of Prescribing Information Sublocade," located at <http://indivior.com/wp-content/uploads/2017/11/SOBLOCADE-Prescribing-Information.pdf> last accessed Nov. 28, 2018, 39 pages.
Anon (Nov. 30, 2017). "FDA Approves SUBLOCADE™ (Buprenorphine Extended-Release), the First and Only Once-Monthly Injectable Buprenorphine Formulation to Treat Moderate to Severe Opioid Use Disorder," located at <https://web.arch ive/org/web/20171204174528/https://www.multivu.com/players/English/8221151-indivior-sublocade-buprenorphine-fda-approval> last accessed Nov. 29, 2018 11 pages.
International Search Report dated Dec. 12, 2018, for PCT Application No. PCT/IB2018/000770, filed Jun. 15, 2018, 6 pages.
Written Opinion dated Dec. 12, 2018, for PCT Application No. PCT/IB2018/000770, filed Jun. 15, 2018, 9 pages.
*Diagnostic and Statistical Manual of Mental Disorders*, Fifth Edition DSM-5, American Psychiatric Publishing, pp. 541-546 (2013).
Fareed, A. et al. (2012). "Effect of buprenorphine dose on treatment outcome," *J Addict Dis* 31(1):8-18.
Johanson, C.E. et al. (Jan. 1, 2012, e-published Aug. 21, 2011). "Diversion and abuse of buprenorphine: findings from national surveys of treatment patients and physicians," *Drug Alcohol Depend* 120(1-3):190-195.
Johnson, B. et al. (Feb. 2015, e-published Oct. 30, 2014). "Diversion of methadone and buprenorphine by patients in opioid substitution treatment in Sweden: prevalence estimates and risk factors," *Int J Drug Policy* 26(2):183-190.
Kampman, K. et al. (Sep.-Oct. 2015). "American Society of Addiction Medicine (ASAM) National Practice Guideline for the Use of Medications in the Treatment of Addiction Involving Opioid Use," *J Addict Med* 9(5):358-367.
Lofwall, M.R. et al. (Dec. 1, 2012, e-published Jun. 15, 2012). "Inability to access buprenorphine treatment as a risk factor for using diverted buprenorphine," *Drug Alcohol Depend* 26(3):379-383.
Nasser, A.F. et al. (Sep. 2014). "A population pharmacokinetic and pharmacodynamic modelling approach to support the clinical development of RBP-6000, a new, subcutaneously injectable, long-acting, sustained-release formulation of buprenorphine, for the treatment of opioid dependence," *Clin Pharmacokinet* 53(9):813-824.
Romero-Gonzalez, M. et al. (Dec. 2017, e-published Nov. 16, 2017). "Buprenorphine-naloxone treatment responses differ between young adults with heroin and prescription opioid use disorders," *Am J Addict* 26(8):838-844.
Saxon, A.J. et al. (Feb. 1, 2013, e-published Aug. 22, 2012). "Buprenorphine/Naloxone and methadone effects on laboratory indices of liver health: a randomized trial," *Drug Alcohol Depend* 128(1-2):71-76.
Shukla, V.K. et al. (1991). "Antagonism of acute cocaine toxicity by buprenorphine," *Life Sci* 49(25):1887-1893.
Sublocade, Highlights of Prescribing Information (2002), 39 pages.
Suboxone®, Highlights of Prescribing Information (2002, revised Feb. 2018), 31 pages.
Subutex®, Highlights of Prescribing Information (2002, revised Dec. 2011, revised Mar. 2018) 14 pages.
Vahia, V.N. et al. (Jul. 2013). "Diagnostic and statistical manual of mental disorders 5: A quick glance," Indian J Psychiatry 55(3):220-223.
Van Ameijden, E.J. et al. (Jul.-Aug. 1999). "Dose-effect relationship between overdose mortality and prescribed methadone dosage in low-threshold maintenance programs," *Addict Behav* 24(4):559-563.
Wroblewski, F. et al. (1958). "The clinical significance of alterations in transaminase activities of serum and other body fluids," *Adv Clin Chem* 1(2):313-351.

\* cited by examiner

METHODS TO TREAT OPIOID USE DISORDER

CROSS-REFERENCE TO RELATED APPLICATIONS

This application is a continuation of International Application PCT/US2018/037921 filed Jun. 15, 2018, pending, which claims priority to U.S. Application No. 62/680,935 filed Jun. 5, 2018; U.S. Application No. 62/656,216 filed Apr. 11, 2018; U.S. Application No. 62/632,995 filed Feb. 20, 2018; U.S. Application No. 62/598,338 filed Dec. 13, 2017; U.S. Application No. 62/572,996 filed Oct. 16, 2017; U.S. Application No. 62/572,331 filed Oct. 13, 2017; and U.S. Application No. 62/521,121 filed Jun. 16, 2017, the disclosures of which are incorporated by reference herein in their entirety.

BACKGROUND

According to the Diagnostic and Statistical Manual for Mental Disorders, 5$^{th}$ Edition (DSM-5), opioid use disorder is characterized by signs and symptoms that reflect compulsive, prolonged self-administration of opioid substances that are used for no legitimate medical purpose or, if another medical condition is present that requires opioid treatment, they are used in doses greatly in excess of the amount needed for that medical condition. In a 2015 report from the National Survey on Drug Use and Health, 12.4 million Americans engaged in non-medical use of prescription pain relievers, including opioids. Approximately 2.06 million Americans met criteria for prescription pain reliever use disorder. The same report suggested that 5.1 million people aged 12 and older have used heroin at some point in their lives, with 828,000 using in the past year and 329,000 using in the past month. There were approximately 580,000 people who had a heroin use disorder in the past year. Perhaps most concerning, deaths from overdose of opioid analgesics (including opioids, methadone and other synthetic narcotics) showed a 5.2-fold increase from 5,528 to 28,647 deaths between 2001 and 2015. Similarly, heroin-related overdose fatalities showed a 5.4-fold increase during this same period, from 1,779 deaths in 2001 to 12,989 in 2015. An emerging concern contributing to recent increases in opioid overdose deaths were 9,580 deaths due to synthetic opioids (other than methadone) which increased 72% in one year (since 2014).

Opioid receptors are located in both the central nervous system (CNS) and the periphery. In the CNS, they are found in high concentrations in the limbic system and the spinal cord. The natural ligands for the opioid receptors are a group of neuropeptides known as endorphins. Opioid analgesics mimic the action of these natural ligands, but have a more prolonged action as they are not subject to rapid local metabolism. Three major opioid receptor subclasses have been identified: μ-, κ- and δ-. Buprenorphine is a partial agonist at the μ-opioid receptor, an antagonist at the κ- and δ-opioid receptors and an agonist at the nociceptin/orphanin FQ (N/OFQ) receptor. In contrast to a full agonist at the μ-opioid receptor, buprenorphine has less maximal euphoric effect, and a ceiling on its respiratory depressant effects. By binding to μ-opioid receptors in the brain, buprenorphine reduces craving for opioids and opiate withdrawal symptoms, minimizing the need of opioid-dependent patients to use illicit opiate drugs. For the maintenance treatment of opioid use disorder, SUBUTEX® tablets (buprenorphine; Indivior, Inc.), SUBOXONE® tablets (buprenorphine/naloxone; Indivior, Inc.), or SUBOXONE® film (buprenorphine/naloxone; Indivior, Inc.) may be given as a single daily dose.

The disclosure provides dosing regimens of sustained-release buprenorphine formulations that provide, among other benefits, optimal dosages, optimal treatment periods, therapeutic steady-state buprenorphine plasma concentrations, and therapeutic steady-state μ-opioid receptor occupancy in the brain for the treatment of opioid use disorder.

SUMMARY

The disclosure provides buprenorphine formulations and monthly dosing regimens that achieve opioid blockade (i) from the first dose of treatment and across the entire monthly dosing interval, (ii) at buprenorphine concentrations that are safe, therapeutic, and well-tolerated; and (iii) that reduce the need for rescue medications. The buprenorphine formulations and monthly dosing regimens achieve clinically significant control of craving and withdrawal symptoms, prevent illicit opioid use, and limit the possibility of misuse and diversion of buprenorphine and enable treatment concordance.

BRIEF DESCRIPTION OF THE FIGURES

FIG. 10A shows the treatment arm of Formulation D at a dose of 300 mg for two months and 100 mg for 4 months. FIG. 10B shows the treatment arm of Formulation D at a dose of 300 mg for 6 months. FIG. 10C shows the placebo arm. The solid lines are the Kaplan Meier curves for observations, while the dashed line are the Kaplan Meier curves for model predictions. In FIG. 10C, the upper line represents the age group of 51-64; the next lower line represents the age group of 41-50; the next lower line represents the age group of 31-40; and the lowest line represents the age group of 19-30.

FIG. 14A shows the treatment arm of Formulation D at a dose of 300 mg for two months and 100 mg for 4 months. FIG. 14B shows the treatment arm of Formulation D at a dose of 300 mg for 6 months. FIG. 14C shows the placebo arm.

FIG. 15A shows the treatment arm of Formulation D at a dose of 300 mg for two months and 100 mg for 4 months. FIG. 15B shows the treatment arm of Formulation D at a dose of 300 mg for 6 months. FIG. 15C shows the placebo arm. The solid lines are the Kaplan Meier curves for observations, while the dashed line are the Kaplan Meier curves for model predictions. In each figure, the upper line represents black/African-American patients and the lower line represents all other races combined (primarily Caucasian patients). The data shows that race was a significant predictor in all treatment arms, with dropout rates reduced by about 40% in black/African American patients compared to Caucasian/other patients.

FIG. 16A shows the treatment arm of Formulation D at a dose of 300 mg for two months and 100 mg for 4 months. FIG. 16B shows the treatment arm of Formulation D at a dose of 300 mg for 6 months. FIG. 16C shows the placebo arm. The solid lines are the Kaplan Meier curves for observations, while the dashed line are the Kaplan Meier curves for model predictions. A higher dropout rate (the lower line in FIG. 16C) was only seen in the placebo group when the CGI-S score was less 1-3 (normal to mildly ill).

FIG. 18A shows that patients in the treatment groups who had a craving score greater than 20 had a dropout rate that was three times higher than those patients who had a craving score of 1-5. FIG. 18B shows that patients in the placebo group who had a craving score greater than 20 had a dropout rate that was 3.6 times higher than those patients who had a craving score of 1-5.

In FIGS. 19A-B, "Injecting Users" refers to injection drug patients. With reference to week 24 in FIGS. 19A and 19B, the upper line represents injection drug patients administered the 300/300 mg dosing regimen, and the lower line represents injection drug patients administered the 300/100 mg dosing regimen. With reference to FIG. 19B, at Week 24 the abstinence risk was increased 1.7 fold (54% v. 32%) in patients administered the 300/300 mg vs. the 300/100 mg dosing regimen (95% CI: 1.2-2.4).

With reference to FIG. 20 at week 49, the top line (c) refers to de novo subjects; the middle line (a) refers to roll-over subjects on the 300 mg/100 mg dosing regimen; and the bottom line (b) refers to roll-over subjects on the 300 mg/300 mg dosing regimen.

DETAILED DESCRIPTION

Figure 1:
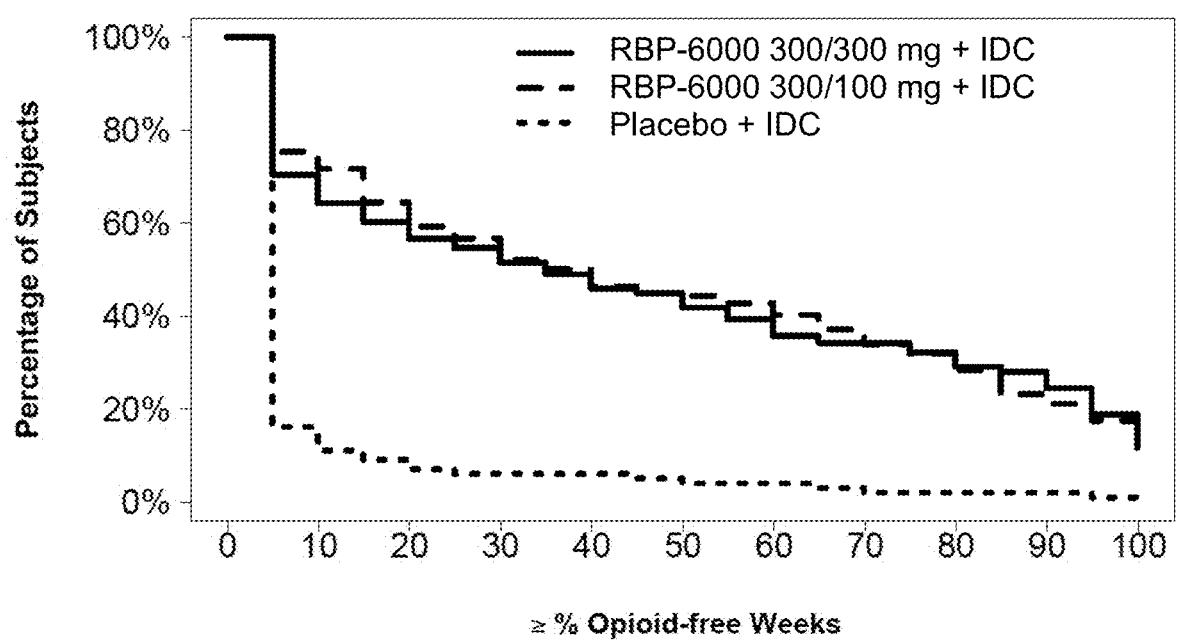
FIG. 1 shows the cumulative distribution function (CDF) of the percentage of urine samples negative for illicit opioids combined with self-reports negative for illicit opioid use collected from Weeks 5 to 24 of the study. The x-axis represents the percentage of abstinence and the y-axis represents the percentage of patients. With reference to Week 10, the top line is "RBP-6000 300/100 mg+IDC," the middle line is "RBP-6000 300/300 mg+IDC," and the bottom line is "Placebo+IDC."

"Buprenorphine" refers to buprenorphine free base and buprenorphine pharmaceutically acceptable salts (e.g., buprenorphine hydrochloride). Buprenorphine free base is a semisynthetic derivative of thebaine, and is mixed partial agonist opioid receptor modulator. Buprenorphine free base has a chemical formula $C_{29}H_{41}NO_4$, and a chemical name 21-cyclopropyl-7α-[(S)-1-hydroxy-1,2,2-trimethylpropyl]-6,14-endo-ethano-6,7,8,14-tetrahydrooropavine. In aspects, buprenorphine refers to buprenorphine free base.

"Sustained-release buprenorphine formulation," "buprenorphine composition," "composition," "formulation" or "buprenorphine formulation" refer to any formulation comprising buprenorphine that can provide therapeutic plasma concentration levels of buprenorphine for at least 1 month. In aspects, buprenorphine compositions are injectable depot formulations or surgically implantable depot formulations. In aspects, the sustained-release buprenorphine formulation is an injectable formulation. In aspects, the sustained-release buprenorphine formulation is a subcutaneous injectable formulation. In aspects, the buprenorphine composition is Formulation A, Formulation B, Formulation C, Formulation D, Formulation D300, Formulation D100, Formulation E, or variations thereof.

"Therapeutic levels" of buprenorphine refers to buprenorphine plasma concentrations that are effective: (a) in the treatment of opioid use disorder; (b) in suppressing opioid withdrawal symptoms; (c) in eliminating opioid withdrawal symptoms; (d) in reducing opioid craving; (e) in eliminating opioid craving; (f) in reducing illicit opioid use; (g) in preventing illicit opioid use; (h) in inducing opioid abstinence; or (i) a combination of two or more of the foregoing. "Therapeutic levels" can also be described in terms of steady-state minimum buprenorphine plasma concentration levels, steady-state average buprenorphine plasma concentration levels, and steady-state maximum buprenorphine plasma concentration levels, all of which are described in more detail herein.

"One month" means 24 days to 32 days. In aspects, one month is 26 days to 32 days. In aspects, one month is 26 days to 30 days. In aspects, one month is 27 days to 29 days. In aspects, one month is 28 days to 31 days. In aspects, one month is 28 days. In aspects, one month is 29 days. In aspects, one month is 30 days. In aspects, one month is 31 days.

"Patient" or "subject" refers to a human. In aspects, the "patient" is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene. Methods for identifying whether a patient has a TC genotype for SNP rs678849 on OPRD1 gene or a TT genotype for SNP rs678849 on OPRD1 gene are known in the art, and include commercially available genotypying assays, e.g., TAQMAN® SNP Genotyping Assays (Applied Biosystems Inc. (ABI); Foster City, Calif., USA).

"Injection drug patient" refers to a patient who used illicit opioids by an injectable route at baseline (e.g., upon entry into the treatment program described herein or prior to beginning treatment with the methods and formulations described herein). "Injection drug patient" can be used interchangeably with "patient injecting illicit opioids" and "patient using illicit opioids by injectable route." In aspects, the injectable route is intravenous. In aspects, the injectable route is intramuscular. In aspects, the injectable route is subcutaneous. In aspects, the "injection drug patient" is an intravenous injection drug patient, i.e., the patient intravenously injects illicit opioids. In aspects, the "injection drug patient" is an intramuscular injection drug patient, i.e., the patient intramuscularly injects illicit opioids. In aspects, the "injection drug patient" is a subcutaneous injection drug patient, i.e., the patient subcutaneously injects illicit opioids.

"Illicit opioid" refers to any opioid that is abused or misused by a patient. The illicit opioid can be a street drug (e.g., heroin) or a prescription drug (e.g., fentanyl, oxycodone, hydrocodone, hydromorphone, oxymorphone, meperidine, morphine, codeine, methadone). In aspects, the illicit opioids are abused by an injectable route. In aspects, the illicit opioids are abused by a non-injectable route, such as pulmonary route (e.g., smoking), oral route (e.g., swallowing), nasal route (e.g., snorting), or rectal route (e.g., suppository).

"Black" or "African-American" refers to a patient who self-identifies their race as black or African-American.

"OPRD1" refers to the opioid receptor delta 1 gene having the UniProtKB Accession Number P41143.

With reference to the Diagnostic and Statistical Manual for Mental Disorders, 5th Edition, American Psychiatric Association, 2013 (also referred to herein as DSM5), the disclosure of which is incorporated by reference herein in its entirety, "opioid use disorder" is characterized by signs and symptoms that reflect compulsive, prolonged self-administration of opioid substances that are used for no legitimate medical purpose or, if another medical condition is present that requires opioid treatment, they are used in doses greatly in excess of the amount needed for that medical condition. In aspects, the opioid use disorder is moderate opioid use disorder. "Moderate opioid use disorder" is defined by reference to the DSM5 Opioid Use Disorder Checklist (ICD-9-CM code 304.00 or ICD-10-CM code F11.20) as having the presence of 4 or 5 symptoms indicated in the DSM5 Opioid Use Disorder Checklist. In aspects, the opioid use disorder is severe opioid use disorder. "Severe opioid use disorder" is defined by reference to the DSM5 Opioid Use Disorder Checklist (ICD-9-CM code 304.00 or ICD-10-CM code F11.20) as having the presence of 6 or more symptoms indicated in the DSM5 Opioid Use Disorder Checklist. In aspects, the opioid use disorder is moderate-to-severe opioid use disorder. Moderate-to-severe opioid use disorder refers to the presence of 4 or more symptoms indicated in the DSM5 Opioid Use Disorder Checklist. In aspects, the opioid use disorder is mild opioid use disorder. "Mild opioid use disorder" is defined by reference to the DSM5 Opioid Use Disorder Checklist (ICD-9-CM code 305.50 or ICD-10-CM code F11.10) as having the presence of 2 or 3 symptoms indicated in the DSM5 Opioid Use Disorder Checklist. In aspects, the opioid use disorder is mild-to-moderate opioid use disorder. Mild-to-moderate opioid use disorder refers to the presence of 2 to 5 symptoms indicated in the DSM5 Opioid Use Disorder Checklist. In aspects, "treating opioid use disorder" encompasses one or more of: (i) reducing opioid withdrawal symptoms, (ii) eliminating opioid withdrawal symptoms, (iii) reducing opioid craving, (iv) eliminating opioid craving, (v) reducing illicit opioid use, (vi) eliminating illicit opioid use, and (vii) inducing opioid abstinence.

"Opioid withdrawal symptoms" refers to one or more symptoms associated with withdrawal from illicit opioids. Such symptoms can include one or more of the following: agitation, anxiety, muscle aches, increased tearing, insomnia, runny nose, sweating, yawning, abdominal cramping, diarrhea, dilated pupils, goose bumps, nausea, and vomiting. Opioid withdrawal symptoms can begin to occur within a few hours to a few days after the last intake of an opioid. Opiate withdrawal symptoms can be measured by the Clinical Opiate Withdrawal Scale (COWS).

"Reducing opioid withdrawal symptoms" refers to a patient who has fewer or milder illicit opioid withdrawal symptoms when compared to the withdrawal symptoms at a baseline time point. In aspects, the method of reducing opioid withdrawal symptoms refers to a patient who has a lower score on the COWS when compared to a baseline time point. In aspects, the baseline time point is prior to beginning treatment with the methods and formulations described herein.

"Eliminating opioid withdrawal symptoms" refers to a patient who does not have any withdrawal symptoms when compared to the withdrawal symptoms at a baseline time point. In aspects, the method of eliminating illicit opioid withdrawal symptoms refers to a patient who has a score of 0 to 4 on the COWS. In aspects, the baseline time point is prior to beginning treatment with the methods and formulations described herein.

"Craving" refers to a desire of a patient to take an illicit opioid, and may have physical, behavioral, or cognitive underpinnings. Craving can be measured, for example, by the Opioid Craving Visual Analog Scale (VAS), which is a self-report by patients of the intensity of their illicit opioid craving on a 0 to 100 mm scale. In aspects, craving is a symptom of opioid use disorder where the patient is actively taking illicit opioids or where the patient has stopped taking illicit opioids.

"Reducing opioid craving" refers to a patient who has less or milder craving for illicit opioids when compared to the craving at a baseline time point. In aspects, the method of reducing opioid craving refers to a patient who achieves a lower score on opioid craving VAS when compared to a baseline time point. In aspects, the baseline time point is prior to beginning treatment with the methods and formulations described herein.

"Eliminating opioid craving" refers to a patient who does not have any craving for an illicit opioid. In embodiments, the methods of eliminating opioid craving refers to a patient who has a score of 0 on opioid craving VAS.

"Reducing illicit opioid use" and "reducing opioid use" refer to a patient who consumes (e.g., injectable/non-injectable routes) less illicit opioids when compared to a baseline time point or time frame. In aspects, the baseline time point is prior to beginning treatment with the methods and formulations described herein.

"Preventing illicit opioid use" or "preventing opioid use," refer to a patient who does not or no longer consumes (e.g., injectable/non-injectable routes) illicit opioids. "Preventing illicit opioid use" results in "opioid abstinence." In aspects, "preventing illicit opioid use" refers to prevent illicit opioid use in a patient who has previously consumed illicit opioids.

"Eliminating illicit opioid use" or "eliminating opioid use" refers to a patient who is abstinent from opioid use during and/or following treatment with the formulations and dosing regimens described herein.

"Opioid abstinence" or "opioid abstinent" refers to a patient who does not take illicit opioids at the time of the assessment. In aspects, opioid abstinence is identified by negative urine drug screens for illicit opioids combined with negative self-reports for illicit opioid use. In aspects, the methods described herein allow for a patient to maintain opioid abstinence over a period of time. In aspects, "percentage abstinence" refers to the number of times the patient was abstinent (e.g., urine drug screen negative for illicit opioids and/or self-report negative for illicit opioid use) over a defined time period. Complete/full abstinence means percentage abstinence is 100%. Treatment success means percentage abstinence is 80% or more.

"Detecting illicit opioid use, opioid craving, or opioid withdrawal symptoms" refers to evaluating a patient for illicit opioid use, opioid craving, or opioid withdrawal symptoms. In aspects, the detection occurs by a doctor or other medical professional speaking with a patient and diagnosing or identifying the craving, symptom, or use based on patient self-reporting (i.e., the patient tells the doctor or other medical professional that they have used illicit opioids). In aspects, the detection occurs by a medical test, such as a urine drug screen that can identify illicit opioid use by the presence of opioids and/or opioid metabolites in urine. Urine drug screens to detect illicit opioid use are known in the art. In aspects, the detection occurs by a medical test such as opioid craving Visual Analog Scale (VAS) or the Clinical Opiate Withdrawal Scale (COWS).

"Detecting a buprenorphine plasma concentration" and "measuring a buprenorphine plasma concentration" refer to a test or assay where a biological sample obtained from a patient is analyzed and the buprenorphine concentration therein is measured. In aspects, the biological sample is blood. In aspects, the biological sample is plasma. In aspects, the biological sample is serum. Methods for analyzing and measuring buprenorphine concentrations from biological samples are known in the art and described for example, in WO 2017/077389 and Liu et al, Journal of Pharmaceutical and Biomedical Analysis, 120:142-152 (2016), the disclosures of which are incorporated by reference herein.

"RBP-6000" refers to Formulation D, described herein. RBP-6000, also known as SUBLOCADE™ (Indivior, Richmond, Va.), was approved by the US Food and Drug Administration on Nov. 30, 2017, for the treatment of opioid use disorder. In aspects, RBP-6000 contains about 300 mg buprenorphine free base. In aspects, RBP-6000 contains about 100 mg buprenorphine free base.

"300/100 mg," "300/100," and "300 mg/100 mg" refer to a treatment program where Formulation D containing 300 mg buprenorphine was administered to a patient once per month for two months, and then Formulation D containing 100 mg buprenorphine was administered to a patient once per month for at least four months. Generally, the treatment program includes IDC.

"300/300 mg," "300/300," or "300 mg/300 mg" refer to a treatment program where Formulation D containing 300 mg buprenorphine was administered to a patient once per month for at least six months. Generally, the treatment program includes IDC.

A dosing regimen that is "once per month for two months" means that the buprenorphine composition is administered one time in one month and one time in the following month. For example, the buprenorphine composition is administered the first time on January 1, and then is administered a second time on February 1.

A dosing regimen that is "once per month for at least four months" means that the buprenorphine composition is administered one time in an initial month, one time in the following second month, one time in the following third month, one time in the following further month, and then administration can be discontinued or can continue for another month, two months, 6 months, 1 year, 2 years, or indefinitely. For example, the buprenorphine composition is administered the first time on January 1, is administered a second time on February 1, is administered a third time on March 1, is administered a fourth time on April 1, and can then optionally continue to be administered monthly thereafter.

"IDC" refers to individual drug counseling.

"Administering" means parenteral administration of the formulations described herein to the patient or the implantation of a slow-release device in the patient. Parenteral administration includes, for example, intravenous, intramuscular, intra-arterial, intradermal, intrathecal, subcutaneous, intraperitoneal, intraventricular, and intracranial. In aspects, "administering" refers to subcutaneously injecting the formulations described herein.

"Pharmaceutically acceptable salt" refers to acid or base salts of buprenorphine. Examples of pharmaceutically acceptable salts include mineral acid (hydrochloric acid, hydrobromic acid, phosphoric acid, and the like) salts, organic acid (acetic acid, propionic acid, glutamic acid, citric acid and the like) salts, quaternary ammonium salts, and the like.

"$EC_{50}$" is the buprenorphine plasma concentration yielding half of the maximal effect ($E_{max}$) in the $E_{max}$ model used for logistic regression modeling of abstinence data "Equation 1" refers to the maximal effect ($E_{max}$) model that is used to describe the relationship between buprenorphine plasma concentrations and μ-opioid receptor occupancy (μORO) as follows:

$$\mu ORO = \frac{E_{max} \cdot Cp}{EC_{50} + Cp}$$

where Cp is buprenorphine plasma concentration and $EC_{50}$ is buprenorphine plasma concentration expected to achieve 50% of the maximal μORO ($E_{max}$). This model was developed assuming a direct relationship between plasma concentration and μORO without equilibration delay. This model assumes that the metabolite norbuprenorphine has negligible activity with respect to brain μORO. Equation 1 is further described in WO 2016/071767, the disclosure of which is incorporated by reference herein in its entirety.

"Steady state" or "steady-state" refers to the situation where the overall intake of a drug is in dynamic equilibrium with its elimination.

"$C_{min}$" or "minimum concentration" refers to the lowest concentration of a drug present in a patient's plasma over the dosing interval. The lowest concentration generally occurs immediately preceding administration of a drug in a dosing regimen.

"Steady-state minimum buprenorphine plasma concentration" refer to the lowest concentration of buprenorphine present in the patient's plasma over the dosing interval at steady state. In aspects, the steady-state $C_{min}$ is achieved after about 5 months of treatment with the buprenorphine formulations described herein. In aspects, the steady-state $C_{min}$ is achieved after about 6 months of treatment with the buprenorphine formulations described herein. Six months of treatment refers to the once-monthly administration of six doses of the buprenorphine formulations described herein. In aspects, the minimum buprenorphine plasma concentration is the average of individual values for the minimum buprenorphine plasma concentrations for a group of patients in a study or a group of patients taking the formulations described herein. In aspects, the minimum buprenorphine plasma concentration is that for a single patient.

"$C_{max}$" or "maximum concentration" refer to the highest concentration of drug present in the patient's plasma over the dosing interval.

"Steady-state maximum buprenorphine plasma concentration" refer to the highest steady-state concentration of buprenorphine present in the patient's plasma. The steady-state $C_{max}$ is generally reached within the first day (e.g., about 18-36 hours; or about 20-24 hours) after administration of the buprenorphine formulations described herein. In aspects, the steady-state $C_{max}$ is achieved after about 5 months of treatment with the buprenorphine formulations described herein. In aspects, the steady-state $C_{max}$ is achieved after about 6 months of treatment with the buprenorphine formulations described herein. Six months of treatment refers to the once-monthly administration of six doses of the buprenorphine formulations described herein. In aspects, the maximum buprenorphine plasma concentration is the average of individual values for the maximum buprenorphine plasma concentrations for a group of patients in a study or a group of patients taking the formulations described herein. In aspects, the maximum buprenorphine plasma concentration is that for a single patient.

"$C_{avg}$" or "average concentration" refer to the average concentration of drug that is present in the patient's plasma over a dosing interval.

"Steady-state average buprenorphine concentration," and "mean steady-state buprenorphine concentration" refer to the steady-state average concentration of buprenorphine that is present in the patient's plasma. In aspects, the steady-state $C_{avg}$ is achieved after about 5 months of treatment with the buprenorphine formulations described herein. In aspects, the steady-state $C_{avg}$ is achieved after about 6 months of treatment with the buprenorphine formulations described herein. Six months of treatment refers to the once-monthly administration of six doses of the buprenorphine formulations described herein. In aspects, the average buprenorphine plasma concentration is the average of individual values for the average buprenorphine plasma concentrations for a group of patients in a study or a group of patients taking the formulations described herein. In aspects, the average buprenorphine plasma concentration is that for a single patient.

In one embodiment, the sustained-release buprenorphine formulation is Formulation E. "Formulation E" is a composition that comprises or consists of: (i) buprenorphine free base; (ii) a poly(lactide-co-glycolide) copolymer; and (iii) N-methyl-2-pyrrolidone. In aspects, the poly(lactide-co-glycolide) copolymer is a 50:50 to 95:5 poly(lactide-co-glycolide) copolymer. In aspects, the poly(lactide-co-glycolide) copolymer is a 50:50 to 80:20 poly(lactide-co-glycolide) copolymer. In aspects, the poly(DL-lactide-co-glycolide) copolymer is a 50:50 poly(lactide-co-glycolide) copolymer. In aspects, the poly(lactide-co-glycolide) copolymer is a poly(DL-lactide-co-glycolide) copolymer. In aspects, the poly(lactide-co-glycolide) copolymer has an average molecular weight of about 1,000 Daltons to about 50,000 Daltons. In aspects, the poly(lactide-co-glycolide) copolymer has an average molecular weight of about 5,000 Daltons to about 25,000 Daltons. In aspects, the poly(lactide-co-glycolide) copolymer has an average molecular weight of about 9,000 Daltons to about 19,000 Daltons. In aspects, the poly(lactide-co-glycolide) copolymer has a carboxy terminal group.

In one embodiment, the sustained-release buprenorphine formulation is Formulation D. "Formulation D" is a composition that comprises or consists of: (i) about 18 wt % buprenorphine free base; (ii) about 32 wt % of a 50:50 poly(DL-lactide-co-glycolide) copolymer having a carboxy terminal group and having an average molecular weight of about 9,000 Daltons to about 19,000 Daltons; and (iii) about 50 wt % of N-methyl-2-pyrrolidone. Formulation D is also known as SUBLOCADE' (buprenorphine extended-release by Indivior, Inc.).

"Formulation D300" refers to Formulation D containing about 300 mg of buprenorphine free base. Formulation D300 is also known as the 300 mg dose of SUBLOCADE™ (buprenorphine extended-release by Indivior, Inc.).

"Formulation D100" refers to Formulation D containing about 100 mg of buprenorphine free base. Formulation D100 is also known as the 100 mg dose of SUBLOCADE™ (buprenorphine extended-release by Indivior, Inc.).

In one embodiment, the sustained-release buprenorphine formulation is Formulation C. "Formulation C" is a composition that comprises or consists of: (i) about 14 wt % to about 22 wt % buprenorphine in the form of the free base; (ii) about 22 wt % to about 42 wt % of a 50:50 to 80:20 poly(DL-lactide-co-glycolide) copolymer having an average molecular weight of about 5,000 Daltons to about 30,000 Daltons; and (iii) about 40 wt % to about 60 wt % of N-methyl-2-pyrrolidone. In aspects, the poly(DL-lactide-co-glycolide) copolymer has a carboxy terminal group.

In one embodiment, the sustained-release buprenorphine formulation is Formulation B. "Formulation B" is a composition that comprises or consists of: (i) about 10 wt % to about 30 wt % buprenorphine in the form of the free base or a pharmaceutically acceptable salt; (ii) about 10 wt % to about 60 wt % of a 50:50 to 95:5 poly(DL-lactide-co-glycolide) copolymer having an average molecular weight of about 5,000 Daltons to about 40,000 Daltons; and (iii) about 30 wt % to about 70 wt % of N-methyl-2-pyrrolidone. In aspects of Formulation B, the buprenorphine is in the form of the free base. In aspects, the poly(DL-lactide-co-glycolide) copolymer has a carboxy terminal group.

In one embodiment, the sustained-release buprenorphine formulation is Formulation A. "Formulation A" is a composition that comprises or consists of: (i) at least one biodegradable polymer; (ii) at least one organic solvent which comprises an amide, an ester, a carbonate, a ketone, a lactam, an ether, a sulfonyl, or a combination thereof; and (iii) about 5 wt % to about 30 wt % of buprenorphine in the form of a free base or pharmaceutically acceptable salt. In aspects, the buprenorphine is in the form of a free base. In other aspects, the buprenorphine is present in an amount from about 10 wt % to about 25 wt %; or in an amount from about 15 wt % to about 20 wt %. In other aspects, the organic solvent is present in an amount of about 30 wt % to about 70 wt %; or in an amount of about 40 wt % to about 60 wt %. In aspects, the organic solvent is N-methyl-2-pyrrolidone, 2-pyrrolidone, propylene glycol, polyethylene glycol, ethanol, acetone, tetrahydrofurfuryl alcohol, dimethyl isosorbide, acetic acid, lactic acid, methyl lactate, ethyl lactate, monomethyl succinate acid, monomethyl citric acid, glycofurol, glycerol formal, isopropylidene glycol, 2,2-dimethyl-1,3-dioxolone-4-methanol, dimethylformamide, dimethylacetamide, N,N-dimethylformamide, propylene carbonate, triacetin, dimethylsulfoxide, dimethylsulfone, epsilon-caprolactone, butyrolactone, caprolactam, and a mixture of two or more thereof. In other aspects, the organic solvent is N-methyl-2-pyrrolidone, 2-pyrrolidone, N,N-dimethylformamide, dimethyl sulfoxide, propylene carbonate, caprolactam, polyethylene glycol, ethanol, or a mixture of two or more thereof. In other aspects, the organic solvent is N-methyl-2-pyrrolidone. The term "biodegradable polymer" refers to any polymer that can degrade in vivo and be eliminated from a patient's body. In other aspects, the biodegradable polymer is present in an amount of about 10 wt % to about 90 wt %; or in an amount of about 10 wt % to about 80 wt %; or in an amount of about 10 wt % to about 70 wt %; or in an amount of about 10 wt % to about 60 wt %; or in an amount of about 10 wt % to about 50 wt %; or in an amount of about 20 wt % to about 40 wt %. In aspects, the polymer is a polylactide, a polyglycolide, a polycaprolactone, a copolymer thereof, a terpolymer thereof, any combination thereof, or a mixture of two or more thereof. In aspects, the polymer is a poly(DL-lactide-co-glycolide) copolymer. The polymer, such as the poly(DL-lactide-co-glycolide) copolymer, can have an average molecular weight of about 1,000 Daltons to about 50,000 Daltons; or from about 5,000 Daltons to about 40,000 Daltons; or from about 5,000 Daltons to about 30,000 Daltons; or from about 5,000 Daltons to about 20,000 Daltons; or from about 10,000 Daltons to about 20,000 Daltons. The poly(DL-lactide-co-glycolide) copolymer can be a 50:50 to 95:5 poly(DL-lactide-co-glycolide) copolymer; or a 50:50 to 80:20 poly (DL-lactide-co-glycolide) copolymer; or a 50:50 poly(DL-lactide-co-glycolide) copolymer. In aspects, the poly(DL-lactide-co-glycolide) copolymer has a carboxy terminal group.

The phrase "average molecular weight" refers to the weight average molecular weight of a polymer as determined by gel permeation chromatography (also known as GPC or size exclusion chromatography) using tetrahydrofuran as the solvent and using a molecular weight calibration curve using polystyrene standards.

In one embodiment, the buprenorphine formulations comprise from about 295 mg to about 305 mg of buprenorphine, or about 300 mg of buprenorphine. In aspects, the buprenorphine formulation is Formulation D comprising from about 295 mg to about 305 mg of buprenorphine free base; or from about 296 mg to about 304 mg of buprenorphine free base; or from about 297 mg to about 303 mg of buprenorphine free base; or from about 298 mg to about 302 mg of buprenorphine free base; or about 299 mg to about 301 mg of buprenorphine free base. In aspects, the buprenorphine formulations comprise about 300 mg buprenorphine free base.

In one embodiment, the buprenorphine formulations comprise from about 95 mg to about 105 mg buprenorphine, or about 100 mg buprenorphine. In aspects, the buprenorphine formulation is Formulation D comprising from about 95 mg to about 105 mg of buprenorphine free base; alternatively from about 96 mg to about 104 mg, alternatively from about 97 mg to about 103 mg, alternatively from about 98 mg to about 102 mg, alternatively from about 99 mg to about 101 mg, alternatively about 100 mg of buprenorphine free base.

In embodiments, the sustained-release buprenorphine formulation is a formulation described in U.S. Pat. Nos. 8,921, 387, 8,975,270, 9,272,044, 9,498,432, 9,782,402, 9,827,241, and WO 2016/071767, the disclosures of which are incorporated by reference herein in their entirety. In aspects, the sustained-release buprenorphine formulation is a formulation described in U.S. Pat. Nos. 8,236,292, 8,236,755, 8,545,832, and 9,526,788, the disclosures of which is incorporated by reference herein in its entirety.

In embodiments, the disclosure provides methods of treating moderate-to-severe opioid use disorder in an injection drug patient in need thereof comprising subcutaneously administering a buprenorphine composition once per month for at least six months to the injection drug patient; wherein the buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone. In aspects, the methods comprise subcutaneously administering the buprenorphine composition once per month for at least twelve months. In aspects, the methods produce opioid abstinence in the injection drug user.

In embodiments, the disclosure provides methods of treating moderate-to-severe opioid use disorder in an injection drug patient in need thereof comprising subcutaneously administering a buprenorphine composition once per month for at least six months to the injection drug patient; wherein the buprenorphine composition comprises: (i) about 300 mg buprenorphine free base at 18 wt %; (ii) about 32 wt % of a poly(DL-lactide-co-glycolide) copolymer; and (iii) about 50 wt % of N-methyl-2-pyrrolidone. In aspects, the methods comprise subcutaneously administering the buprenorphine composition once per month for at least twelve months. In aspects, the methods produce opioid abstinence in the injection drug user.

In embodiments, the disclosure provides methods of treating opioid use disorder in an injection drug patient in need thereof comprising subcutaneously administering to the injection drug patient a buprenorphine composition once per month for at least six months to the injection drug patient; wherein the buprenorphine composition comprises about 300 mg buprenorphine free base, a poly(lactide-co-glycolide) copolymer, and N-methyl-2-pyrrolidone. In aspects, the opioid use disorder is moderate-to-severe opioid use disorder. In aspects, the opioid use disorder is moderate opioid use disorder. In aspects, the opioid use disorder is severe opioid use disorder. In aspects, the method of treating opioid use disorder is a method for reducing opioid craving. In aspects, the method of treating opioid use disorder is a method for eliminating opioid craving. In aspects, the method of treating opioid use disorder is a method for reducing opioid withdrawal symptoms. In aspects, the method of treating opioid use disorder is a method for eliminating opioid withdrawal symptoms. In aspects, the method of treating opioid use disorder is a method for reducing illicit opioid use. In aspects, the method of treating opioid use disorder is a method for eliminating illicit opioid use. In aspects, the method of treating opioid use disorder is a method for inducing opioid abstinence. In aspects, the buprenorphine composition comprises: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone. In aspects, the buprenorphine composition comprises: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone. In aspects, the buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone. In aspects, the methods comprise subcutaneously administering the buprenorphine composition once per month for at least twelve months. In aspects, the injection drug patient is an intravenous injection drug patient. In aspects, the injection drug patient is an intramuscular injection drug patient. In aspects, the injection drug patient is a subcutaneous injection drug patient. In aspects, the injection drug patient has a TC genotype for SNP rs678849 on OPRD1 gene. In aspects, the injection drug patient has a TT genotype for SNP rs678849 on OPRD1 gene. In aspects, the injection drug patient is black.

In embodiments, the disclosure provides methods of treating opioid use disorder in a patient in need thereof, the method comprising the steps, in order, of: (i) subcutaneously administering a first buprenorphine composition to the patient once per month for two months; wherein the first buprenorphine composition comprises about 300 mg buprenorphine free base, a poly(lactide-co-glycolide) copolymer, and N-methyl-2-pyrrolidone; and thereafter: (ii) subcutaneously administering a second buprenorphine composition to the patient once per month for at least one month; wherein the second buprenorphine composition comprises about 100 mg buprenorphine free base, a poly(lactide-co glycolide) copolymer, and N-methyl-2-pyrrolidone; and thereafter: (iii) detecting illicit opioid use, opioid craving, or opioid withdrawal symptoms in the patient; and thereafter (iv) subcutaneously administering a third buprenorphine composition to the patient once per month for at least one month; wherein the third buprenorphine composition comprises about 300 mg buprenorphine free base, a poly(lactide-co-glycolide) copolymer, and N-methyl-2-pyrrolidone. In aspects, the opioid use disorder is moderate-to-severe opioid use disorder. In aspects, the opioid use disorder is moderate opioid use disorder. In aspects, the opioid use disorder is severe opioid use disorder. In aspects, the method of treating opioid use disorder is a method for reducing opioid craving. In aspects, the method of treating opioid use disorder is a method for eliminating opioid craving. In aspects, the method of treating opioid use disorder is a method for reducing opioid withdrawal symptoms. In aspects, the method of treating opioid use disorder is a method for eliminating opioid withdrawal symptoms. In aspects, the method of treating opioid use disorder is a method for reducing illicit opioid use. In aspects, the method of treating opioid use disorder is a method for eliminating illicit opioid use. In aspects, the method of treating opioid use disorder is a method for inducing opioid abstinence. In aspects, step (ii) comprises subcutaneously administering the second buprenorphine composition to the patient once per month for one month to twenty-four months. In aspects, step (ii) comprises subcutaneously administering the second buprenorphine composition to the patient once per month for one month twelve months. In aspects, step (ii) comprises subcutaneously administering the second buprenorphine composition to the patient once per month for one month to six months. In aspects, step (ii) comprises subcutaneously administering the second buprenorphine composition to the patient once per month for one month to five months. In aspects, step (ii) comprises subcutaneously administering the second buprenorphine composition to the patient once per month for one month to four months. In aspects, step (ii) comprises subcutaneously administering the second buprenorphine composition to the patient once per month for one month to three months. In aspects, step (ii) comprises subcutaneously administering the second buprenorphine composition to the patient once per month for one month or two months. In aspects, step (iii) comprises detecting illicit opioid use in the patient. In aspects, detecting illicit opioid use comprises self-reporting of illicit opioid use by the patient, e.g., the patient tells their doctor or other medical professional that they have used illicit opioids. In aspects, detecting illicit opioid use comprises detecting a positive urine drug screen for an illicit opioid, thereby confirming through the urine drug screen that the patient has used an illicit opioid. In aspects, detecting illicit opioid use comprises self-reporting of illicit opioid use by the patient and detecting a positive urine drug screen for an illicit opioid. In aspects, step (iii) comprises detecting opioid craving in the patient. In aspects, detecting opioid craving comprises detecting a buprenorphine plasma concentration of less than 4 ng/mL in the patient. In aspects, detecting opioid craving comprises detecting a buprenorphine plasma concentration of less than 3.5 ng/mL in the patient. In aspects, detecting opioid craving comprises detecting a buprenorphine plasma concentration of less than 3 ng/mL in the patient. In aspects, detecting opioid craving comprises detecting a buprenorphine plasma concentration of less than 2.5 ng/mL in the patient. In aspects, detecting opioid craving comprises detecting a buprenorphine plasma concentration of less than 2 ng/mL in the patient. In aspects, step (iii) comprises detecting opioid withdrawal symptoms in the patient. In aspects, detecting the opioid withdrawal symptom comprises detecting a buprenorphine plasma concentration of less than 4 ng/mL in the patient. In aspects, detecting the opioid withdrawal symptom comprises detecting a buprenorphine plasma concentration of less than 3.5 ng/mL in the patient. In aspects, detecting the opioid withdrawal symptom comprises detecting a buprenorphine plasma concentration of less than 3 ng/mL in the patient. In aspects, detecting the opioid withdrawal symptom comprises detecting a buprenorphine plasma concentration of less than 2.5 ng/mL in the patient. In aspects, detecting the opioid withdrawal symptom comprises detecting a buprenorphine plasma concentration of less than 2 ng/mL in the patient. In aspects, the first buprenorphine composition and the third buprenorphine composition comprise: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone; and wherein the second buprenorphine composition comprises: (i) about 100 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone. In aspects, the first buprenorphine composition and the third buprenorphine composition comprise: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone; and wherein the second buprenorphine composition comprises: (i) about 100 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone. In aspects, the first buprenorphine composition and the third buprenorphine composition comprise: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone; and wherein the second buprenorphine composition comprises: (i) about 100 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone. In aspects, the injection drug patient is an intravenous injection drug patient. In aspects, the injection drug patient is an intramuscular injection drug patient. In aspects, the injection drug patient is a subcutaneous injection drug patient. In aspects, the injection drug patient has a TC genotype for SNP rs678849 on OPRD1 gene. In aspects, the injection drug patient has a TT genotype for SNP rs678849 on OPRD1 gene. In aspects, the injection drug patient is black.

In embodiments, the disclosure provides methods of treating opioid use disorder in a patient in need thereof, the method comprising the steps, in order, of: (i) subcutaneously administering a first buprenorphine composition to the patient once per month for two months; wherein the first buprenorphine composition comprises about 300 mg buprenorphine free base, a poly(lactide-co-glycolide) copolymer, and N-methyl-2-pyrrolidone; and thereafter: (ii) subcutaneously administering a second buprenorphine composition to the patient once per month for at least one month; wherein the second buprenorphine composition comprises about 100 mg buprenorphine free base, a poly(lactide-co glycolide) copolymer, and N-methyl-2-pyrrolidone; and thereafter: (iii) detecting a buprenorphine plasma concentration of less than 4 ng/mL in the patient; and thereafter (iv) subcutaneously administering a third buprenorphine composition to the patient once per month for at least one month; wherein the third buprenorphine composition comprises about 300 mg buprenorphine free base, a poly(lactide-co-glycolide) copolymer, and N-methyl-2-pyrrolidone. In aspects, the opioid use disorder is moderate-to-severe opioid use disorder. In aspects, the opioid use disorder is moderate opioid use disorder. In aspects, the opioid use disorder is severe opioid use disorder. In aspects, the method of treating opioid use disorder is a method for reducing opioid craving. In aspects, the method of treating opioid use disorder is a method for eliminating opioid craving. In aspects, the method of treating opioid use disorder is a method for reducing opioid withdrawal symptoms. In aspects, the method of treating opioid use disorder is a method for eliminating opioid withdrawal symptoms. In aspects, the method of treating opioid use disorder is a method for reducing illicit opioid use. In aspects, the method of treating opioid use disorder is a method for eliminating illicit opioid use. In aspects, the method of treating opioid use disorder is a method for inducing opioid abstinence. In aspects, step (ii)

comprises subcutaneously administering the second buprenorphine composition to the patient once per month for one month to twenty-four months. In aspects, step (ii) comprises subcutaneously administering the second buprenorphine composition to the patient once per month for one month twelve months. In aspects, step (ii) comprises subcutaneously administering the second buprenorphine composition to the patient once per month for one month to six months. In aspects, step (ii) comprises subcutaneously administering the second buprenorphine composition to the patient once per month for one month to five months. In aspects, step (ii) comprises subcutaneously administering the second buprenorphine composition to the patient once per month for one month to four months. In aspects, step (ii) comprises subcutaneously administering the second buprenorphine composition to the patient once per month for one month to three months. In aspects, step (ii) comprises subcutaneously administering the second buprenorphine composition to the patient once per month for one month or two months. In aspects, step (iii) comprises detecting a buprenorphine plasma concentration of less than 3.9 ng/mL. In aspects, step (iii) comprises detecting a buprenorphine plasma concentration of less than 3.8 ng/mL. In aspects, step (iii) comprises detecting a buprenorphine plasma concentration of less than 3.7 ng/mL. In aspects, step (iii) comprises detecting a buprenorphine plasma concentration of less than 3.6 ng/mL. In aspects, step (iii) comprises detecting a buprenorphine plasma concentration of less than 3.5 ng/mL. In aspects, step (iii) comprises detecting a buprenorphine plasma concentration of less than 3.4 ng/mL. In aspects, step (iii) comprises detecting a buprenorphine plasma concentration of less than 3.3 ng/mL. In aspects, step (iii) comprises detecting a buprenorphine plasma concentration of less than 3.2 ng/mL. In aspects, step (iii) comprises detecting a buprenorphine plasma concentration of less than 3.1 ng/mL. In aspects, step (iii) comprises detecting a buprenorphine plasma concentration of less than 3 ng/mL. In aspects, step (iii) comprises detecting a buprenorphine plasma concentration of less than 2.9 ng/mL. In aspects, step (iii) comprises detecting a buprenorphine plasma concentration of less than 2.8 ng/mL. In aspects, step (iii) comprises detecting a buprenorphine plasma concentration of less than 2.7 ng/mL. In aspects, step (iii) comprises detecting a buprenorphine plasma concentration of less than 2.6 ng/mL. In aspects, step (iii) comprises detecting a buprenorphine plasma concentration of less than 2.5 ng/mL. In aspects, step (iii) comprises detecting a buprenorphine plasma concentration of less than 2.4 ng/mL. In aspects, step (iii) comprises detecting a buprenorphine plasma concentration of less than 2.3 ng/mL. In aspects, step (iii) comprises detecting a buprenorphine plasma concentration of less than 2.2 ng/mL. In aspects, step (iii) comprises detecting a buprenorphine plasma concentration of less than 2.1 ng/mL. In aspects, step (iii) comprises detecting a buprenorphine plasma concentration of less than 2 ng/mL. In aspects, the first buprenorphine composition and the third buprenorphine composition comprise: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone; and wherein the second buprenorphine composition comprises: (i) about 100 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone. In aspects, the first buprenorphine composition and the third buprenorphine composition comprise: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone; and wherein the second buprenorphine composition comprises: (i) about 100 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone. In aspects, the first buprenorphine composition and the third buprenorphine composition comprise: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone; and wherein the second buprenorphine composition comprises: (i) about 100 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone. In aspects, the injection drug patient is an intravenous injection drug patient. In aspects, the injection drug patient is an intramuscular injection drug patient. In aspects, the injection drug patient is a subcutaneous injection drug patient. In aspects, the injection drug patient has a TC genotype for SNP rs678849 on OPRD1 gene. In aspects, the injection drug patient has a TT genotype for SNP rs678849 on OPRD1 gene. In aspects, the injection drug patient is black.

In embodiments, the disclosure provides methods of treating opioid use disorder in a patient having a TC genotype for SNP rs678849 on OPRD1 gene or a TT genotype for SNP rs678849 on OPRD1 gene in need thereof, the method comprising subcutaneously administering a buprenorphine composition to the patient once per month; wherein the buprenorphine composition comprises about 100 mg buprenorphine free base, a poly(lactide-co-glycolide) copolymer, and N-methyl-2-pyrrolidone. In aspects, the method comprising subcutaneously administering the buprenorphine composition to the patient once per month for at least six months. In aspects, the method comprising subcutaneously administering the buprenorphine composition to the patient once per month for at least twelve months. In aspects, the opioid use disorder is moderate-to-severe opioid use disorder. In aspects, the opioid use disorder is moderate opioid use disorder. In aspects, the opioid use disorder is severe opioid use disorder. In aspects, the method of treating opioid use disorder is a method for reducing opioid craving. In aspects, the method of treating opioid use disorder is a method for eliminating opioid craving. In aspects, the method of treating opioid use disorder is a method for reducing opioid withdrawal symptoms. In aspects, the method of treating opioid use disorder is a method for eliminating opioid withdrawal symptoms. In aspects, the method of treating opioid use disorder is a method for reducing illicit opioid use. In aspects, the method of treating opioid use disorder is a method for eliminating illicit opioid use. In aspects, the method of treating opioid use disorder is a method for inducing opioid abstinence. In aspects, the methods comprise subcutaneously administering the buprenorphine composition to the patient once per month for at least twelve months. In aspects, the buprenorphine composition comprise: (i) about 100 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone. In aspects, the buprenorphine composition comprise: (i) about 100 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone. In aspects, the buprenorphine composition comprise: (i) about 100 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone. In aspects, the injection drug patient is an intravenous injection drug patient. In aspects, the injection drug patient is an intramuscular injection drug patient. In aspects, the injection drug patient is a subcutaneous injection drug patient. In aspects, the injection drug patient has a TC genotype for SNP rs678849 on OPRD1 gene. In aspects, the injection drug patient has a TT genotype for SNP rs678849 on OPRD1 gene. In aspects, the injection drug patient is black.

The disclosure provides methods of treating opioid use disorder in a patient in need thereof comprising the steps, in order, of: (i) subcutaneously administering a first buprenorphine composition to the patient once per month for one month or two months; wherein the first buprenorphine composition comprises about 300 mg buprenorphine free base, a poly(lactide-co-glycolide) copolymer, and N-methyl-2-pyrrolidone; and thereafter: (ii) identifying the patient as having a TC genotype for SNP rs678849 on OPRD1 gene or a TT genotype for SNP rs678849 on OPRD1 gene; and thereafter (iii) subcutaneously administering a second buprenorphine composition to the patient once per month; wherein the second buprenorphine composition comprises about 100 mg buprenorphine free base, a poly(lactide-co-glycolide) copolymer, and N-methyl-2-pyrrolidone. In aspects, step (i) comprises subcutaneously administering the first buprenorphine composition to the patient once per month for one month. In aspects, step (i) comprises subcutaneously administering the first buprenorphine composition to the patient once per month for two months. In aspects, step (iii) comprises subcutaneously administering the second buprenorphine composition to the patient once per month for at least six months. In aspects, step (iii) comprises subcutaneously administering the second buprenorphine composition to the patient once per month for at least twelve months. In aspects, the opioid use disorder is moderate-to-severe opioid use disorder. In aspects, the opioid use disorder is moderate opioid use disorder. In aspects, the opioid use disorder is severe opioid use disorder. In aspects, the first buprenorphine composition comprises: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone; and wherein the second buprenorphine composition comprises: (i) about 100 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons. In aspects, the first buprenorphine composition comprises: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone; and wherein the second buprenorphine composition comprises: (i) about 100 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone. In aspects, the first buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone; and wherein the second buprenorphine composition comprises: (i) about 100 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone. In aspects, the method of treating opioid use disorder is a method for reducing opioid craving. In aspects, the method of treating opioid use disorder is a method for eliminating opioid craving. In aspects, the method of treating opioid use disorder is a method for reducing opioid withdrawal symptoms. In aspects, the method of treating opioid use disorder is a method for eliminating opioid withdrawal symptoms. In aspects, the method of treating opioid use disorder is a method for reducing illicit opioid use. In aspects, the method of treating opioid use disorder is a method for eliminating illicit opioid use. In aspects, the patient is an injection drug patient. In aspects, the injection drug patient is an intravenous injection drug patient, an intramuscular injection drug patient, or a subcutaneous injection drug patient. In aspects, the patient is black. In aspects, the patient has the TC genotype for SNP rs678849 on OPRD1 gene. In aspects, the patient has the TT genotype for SNP rs678849 on OPRD1 gene.

In embodiments, the disclosure provides methods of reducing the incidence of QT prolongation in a patient undergoing treatment for opioid use disorder, the method comprising the steps: (i) subcutaneously administering a first buprenorphine composition to the patient once per month for two months; wherein the first buprenorphine composition comprises about 300 mg buprenorphine free base, a poly(lactide-co-glycolide) copolymer, and N-methyl-2-pyrrolidone; and thereafter: (ii) subcutaneously administering a second buprenorphine composition to the patient once per month for at least one month; wherein the second buprenorphine composition comprises about 100 mg buprenorphine free base, a poly(lactide-co glycolide) copolymer, and N-methyl-2-pyrrolidone. "Reducing the incidence of QT prolongation" means that a patient will be less likely to experience a clinical occurrence of an increased QT interval when compared to a control. In aspects, the QT interval is the corrected QT (QTc) interval which accounts for the effect of relevant concomitant medications and illicit drug use on heart rate and/or QT in opioid-dependent patients, as described further in Example 6. In aspects, the control is an oral mucosal buprenorphine product. See Darpo et al, Clinical Therapeutics, 38(2):315-326 (2016). In aspects, the control is a transdermal buprenorphine product. See Kapil et al, Journal of Pain and Symptom Management, 46(1):65-75 (2013). In aspects, the opioid use disorder is moderate-to-severe opioid use disorder. In aspects, the opioid use disorder is moderate opioid use disorder. In aspects, the opioid use disorder is severe opioid use disorder. In aspects, the method of treating opioid use disorder is a method for reducing opioid craving. In aspects, the method of treating opioid use disorder is a method for eliminating opioid craving. In aspects, the method of treating opioid use disorder is a method for reducing opioid withdrawal symptoms. In aspects, the method of treating opioid use disorder is a method for eliminating opioid withdrawal symptoms. In aspects, the method of treating opioid use disorder is a method for reducing illicit opioid use. In aspects, the method of treating opioid use disorder is a method for eliminating illicit opioid use. In aspects, the method of treating opioid use disorder is a method for inducing opioid abstinence. In aspects, the first buprenorphine composition comprise: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone; and wherein the second buprenorphine composition comprises: (i) about 100 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone. In aspects, the first buprenorphine composition comprises: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone; and wherein the second buprenorphine composition comprises: (i) about 100 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone. In aspects, the first buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone; and wherein the second buprenorphine composition comprises: (i) about 100 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone. In aspects, the injection drug patient is an intravenous injection drug patient. In aspects, the injection drug patient is an intramuscular injection drug patient. In aspects, the injection drug patient is a subcutaneous injection drug patient. In aspects, the injection drug patient has a TC genotype for SNP rs678849 on OPRD1 gene. In aspects, the injection drug patient has a TT genotype for SNP rs678849 on OPRD1 gene. In aspects, the injection drug patient is black.

The disclosure provides methods for treating opioid use disorder, methods for reducing opioid craving, methods for eliminating opioid craving, methods for reducing opioid withdrawal symptoms, methods for eliminating opioid withdrawal symptoms, methods for reducing illicit opioid use, and methods for eliminating illicit opioid use in a patient in need thereof by administering Formulation A, Formulation B, Formulation C, Formulation D, or Formulation E to the patient once per month for at least six months; where the Formulation comprises from about 295 mg to about 305 mg of buprenorphine; or from about 296 mg to about 304 mg of buprenorphine; or from about 297 mg to about 303 mg of buprenorphine; or about 298 mg to about 302 mg of buprenorphine; or from about 299 mg to about 301 mg of buprenorphine; or about 300 mg of buprenorphine. In aspects, the methods comprise administering Formulation A, Formulation B, Formulation C, Formulation D, or Formulation E to the patient once per month for at least twelve months. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E. In aspects, each of Formulation A, Formulation B, Formulation C, Formulation D, or Formulation E contain about 300 mg buprenorphine. In aspects, the buprenorphine is buprenorphine free base. In aspects, the injection is a subcutaneous injection. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid use disorder, methods for reducing opioid craving, methods for eliminating opioid craving, methods for reducing opioid withdrawal symptoms, methods for eliminating opioid withdrawal symptoms, methods for reducing illicit opioid use, and methods for eliminating illicit opioid use in a patient in need thereof by administering Formulation A, Formulation B, Formulation C, Formulation D, or Formulation E, each of which comprise from about 295 mg to about 305 mg of buprenorphine (e.g., 300 mg buprenorphine free base), for at least six months to provide a steady-state average buprenorphine plasma concentration from about 5.1 ng/mL to about 10 ng/mL; or from 5.1 ng/mL to about 10 ng/mL; or from about 5.2 ng/mL to about 9 ng/mL; or from 5.2 ng/mL to about 9 ng/mL; or from about 5.3 ng/mL to about 8 ng/mL; or from 5.3 ng/mL to about 8 ng/mL; or from about 5.4 ng/mL to about 7.5 ng/mL; or from 5.4 ng/mL to about 7.5 ng/mL; or from about 5.5 ng/mL to about 7.5 ng/mL; or from 5.5 ng/mL to about 7.5 ng/mL; or from about 5.5 ng/mL to about 7 ng/mL; or from 5.5 ng/mL to about 7 ng/mL; or from about 5.8 ng/mL to about 7.2 ng/mL; or from 5.8 ng/mL to about 7.2 ng/mL; or from about 5.9 ng/mL to about 7.0 ng/mL; or from 5.9 ng/mL to 7.0 ng/mL; or from about 6.0 ng/mL to about 7.0 ng/mL; or from 6.0 ng/mL to about 7.0 ng/mL; or from 6.1 ng/mL to 7.0 ng/mL; or from 6.2 ng/mL to 7.0 ng/mL; or from 6.3 ng/mL to 7.0 ng/mL; or about 6.0 ng/mL to about 6.8 ng/mL; or 6.0 ng/mL to about 6.8 ng/mL; or 6.1 ng/mL to about 6.8 ng/mL; or 6.2 ng/mL to about 6.8 ng/mL; or 6.3 ng/mL to about 6.8 ng/mL; or from about 6.1 ng/mL to about 6.5 ng/mL; or from 6.1 ng/mL to about 6.5 ng/mL; or from about 6.2 ng/mL to about 6.4 ng/mL; or from 6.2 ng/mL to about 6.4 ng/mL; or from about 6.3 ng/mL to about 6.4 ng/mL; or from 6.3 ng/mL to about 6.4 ng/mL; or about 6.3 ng/mL. In aspects, the steady-state average buprenorphine plasma concentration ($C_{avg}$) is from about 6.0 ng/mL to about 7.0 ng/mL. In aspects, the steady-state average buprenorphine plasma concentration ($C_{avg}$) from about 6.3 ng/mL to about 6.7 ng/mL. In aspects, the steady-state average buprenorphine plasma concentration ($C_{avg}$) is about 6.5 ng/mL. In aspects, the patient is administered Formulation A, Formulation B, Formulation C, Formulation D, or Formulation E, any of which comprise from about 295 mg to about 305 mg of buprenorphine (e.g., 300 mg buprenorphine free base), for at least twelve months. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid use disorder, methods for reducing opioid craving, methods for eliminating opioid craving, methods for reducing opioid withdrawal symptoms, methods for eliminating opioid withdrawal symptoms, methods for reducing illicit opioid use, and methods for eliminating illicit opioid use in a patient in need thereof by administering Formulation A, Formulation B, Formulation C, Formulation D, or Formulation E, which comprise about 300 mg buprenorphine free base, for at least six months to provide a steady-state average buprenorphine plasma concentration from about 6.2 ng/mL to about 6.4 ng/mL; or from about 6.3 ng/mL to about 6.4 ng/mL; or about 6.3 ng/mL. In aspects, the patient is administered Formulation A, Formulation B, Formulation C, Formulation D, or Formulation E, which comprise about 300 mg buprenorphine free base, for at least twelve months. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid use disorder, methods for reducing opioid craving, methods for eliminating opioid craving, methods for reducing opioid withdrawal symptoms, methods for eliminating opioid withdrawal symptoms, methods for reducing illicit opioid use, and methods for eliminating illicit opioid use in a patient in need thereof by administering Formulation A, Formulation B, Formulation C, Formulation D, or Formulation E, which comprise from about 295 mg to about 305 mg of buprenorphine (e.g., 300 mg buprenorphine free base), for at least six months to provide a steady-state minimum buprenorphine plasma concentration ($C_{min}$) from about 5.0 ng/mL to a steady-state maximum buprenorphine plasma concentration ($C_{max}$) of about 11 ng/mL; or from about 5.0 ng/mL to about 10 ng/mL, respectively; or from about 5.0 ng/mL to about 9 ng/mL, respectively; or from 5.0 ng/mL to about 11 ng/mL, respectively; or from 5.0 ng/mL to about 10 ng/mL, respectively; or from 5.0 ng/mL to about 9 ng/mL, respectively; or from about 5.1 ng/mL to about 11 ng/mL, respectively; or from about 5.1 ng/mL to about 10 ng/mL, respectively; or from about 5.1 ng/mL to about 9 ng/mL, respectively; or from 5.1 ng/mL to about 11 ng/mL, respectively; or from 5.1 ng/mL to about 10 ng/mL, respectively; or from 5.1 ng/mL to about 9 ng/mL, respectively. In aspects, the steady-state minimum buprenorphine plasma concentration ($C_{min}$) from about 4.5 ng/mL to about 5.5 ng/mL; a steady-state average buprenorphine plasma concentration ($C_{avg}$) from about 6.0 ng/mL to about 7.0 ng/mL; and a steady-state maximum plasma buprenorphine concentration ($C_{max}$) from about 8 ng/mL to about 12 ng/mL in the patient. In aspects, the steady-state minimum buprenorphine plasma concentration ($C_{min}$) from about 4.8 ng/mL to about 5.2 ng/mL; a steady-state average buprenorphine plasma concentration ($C_{avg}$) from about 6.3 ng/mL to about 6.7 ng/mL; and a steady-state maximum plasma buprenorphine concentration ($C_{max}$) from about 9 ng/mL to about 11 ng/mL in the patient. In aspects, the methods described herein provide a steady-state minimum buprenorphine plasma concentration ($C_{min}$) of about 5 ng/mL; a steady-state average buprenorphine plasma concentration ($C_{avg}$) of about 6.5 ng/mL; and a steady-state maximum buprenorphine plasma concentration ($C_{max}$) of about 10.1 ng/mL. In aspects, the patient is administered Formulation A, Formulation B, Formulation C, Formulation D, or Formulation E, which comprise from about 295 mg to about 305 mg of buprenorphine (e.g., 300 mg buprenorphine free base), for at least twelve months. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid dependence, methods for reducing opioid craving, methods for eliminating opioid craving, methods for reducing opioid withdrawal symptoms, methods for eliminating opioid withdrawal symptoms, methods for reducing illicit opioid use, and methods for eliminating illicit opioid use in a patient in need thereof by administering Formulation A, Formulation B, Formulation C, Formulation D, or Formulation E, which comprise about 300 mg buprenorphine free base, for at least six months to provide a steady-state minimum buprenorphine plasma concentration ($C_{min}$) from about 5.1 ng/mL to a steady-state maximum buprenorphine plasma concentration ($C_{max}$) of about 9 ng/mL. In aspects, the patient is administered Formulation A, Formulation B, Formulation C, Formulation D, or Formulation E, which comprise about 300 mg buprenorphine free base, for at least twelve months. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid use disorder, methods for reducing opioid craving, methods for eliminating opioid craving, methods for reducing opioid withdrawal symptoms, methods for eliminating opioid withdrawal symptoms, methods for reducing illicit opioid use, and methods for eliminating illicit opioid use in a patient in need thereof by administering Formulation A, Formulation B, Formulation C, Formulation D, or Formulation E, which comprise from about 295 mg to about 305 mg of buprenorphine (e.g., 300 mg buprenorphine free base), for at least six months produce a steady-state minimum buprenorphine plasma concentration ($C_{min}$) from about 5.0 ng/mL to about 5.2 ng/mL; a steady-state average buprenorphine plasma concentration ($C_{avg}$) from about 6.2 ng/mL to about 6.4 ng/mL; and a steady-state maximum plasma buprenorphine concentration ($C_{max}$) from about 8 ng/mL to about 9 ng/mL in the patient. In aspects, the methods described herein provide a steady-state minimum buprenorphine plasma concentration ($C_{min}$) of about 5.1 ng/mL; a steady-state average buprenorphine plasma concentration ($C_{avg}$) of about 6.3 ng/mL; and a steady-state maximum buprenorphine plasma concentration ($C_{max}$) of about 9 ng/mL. In aspects, the methods described herein provide a steady-state minimum buprenorphine plasma concentration ($C_{min}$) of about 5.1 ng/mL; a steady-state average buprenorphine plasma concentration ($C_{avg}$) of about 6.3 ng/mL; and a steady-state maximum buprenorphine plasma concentration ($C_{max}$) of about 8.7 ng/mL. In aspects, the steady-state minimum buprenorphine plasma concentration ($C_{min}$) from about 4.5 ng/mL to about 5.5 ng/mL; a steady-state average buprenorphine plasma concentration ($C_{avg}$) from about 6.0 ng/mL to about 7.0 ng/mL; and a steady-state maximum plasma buprenorphine concentration ($C_{max}$) from about 8 ng/mL to about 12 ng/mL in the patient. In aspects, the steady-state minimum buprenorphine plasma concentration ($C_{min}$) from about 4.8 ng/mL to about 5.2 ng/mL; a steady-state average buprenorphine plasma concentration ($C_{avg}$) from about 6.3 ng/mL to about 6.7 ng/mL; and a steady-state maximum plasma buprenorphine concentration ($C_{max}$) from about 9 ng/mL to about 11 ng/mL in the patient. In aspects, the methods described herein provide a steady-state minimum buprenorphine plasma concentration ($C_{min}$) of about 5 ng/mL; a steady-state average buprenorphine plasma concentration ($C_{avg}$) of about 6.5 ng/mL; and a steady-state maximum buprenorphine plasma concentration ($C_{max}$) of about 10.1 ng/mL. In aspects, the patient is administered Formulation A, Formulation B, Formulation C, Formulation D, or Formulation E, which comprise from about 295 mg to about 305 mg of buprenorphine (e.g., 300 mg buprenorphine free base), for at least twelve months. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid use disorder, methods for reducing opioid craving, methods for eliminating opioid craving, methods for reducing opioid withdrawal symptoms, methods for eliminating opioid withdrawal symptoms, methods for reducing illicit opioid use, and methods for eliminating illicit opioid use in a patient in need thereof by administering Formulation A, Formulation B, Formulation C, Formulation D, or Formulation E, which comprise from about 295 mg to about 305 mg of buprenorphine (e.g., 300 mg buprenorphine free base), for at least six months provide a steady-state μ-opioid receptor occupancy in the brain, as predicted by the maximal effect model of Equation 1, of at least 80% in the patient. In aspects, the methods provide a steady-state μ-opioid receptor occupancy (as predicted by Equation 1) of at least 81% alternatively at least 82%, alternatively at least 83%, alternatively at least 85%, alternatively at least 90%, alternatively at least 95%, alternatively at least about 98%, alternatively at least 80% to about 90% or about 95% or about 98%, alternatively at least about 81% to about 90% or about 95% or about 98%, alternatively at least about 82% to about 90% or about 95% or about 98%, alternatively at least about 83% to about 90% or about 95% or about 98% or to 100%. In one aspect, the μ-opioid receptor occupancy (as predicted by a maximal effect model of Equation 1) is 100%. Of note, Equation 1 has a maximal effect of 91.4%, but when variability is added, individual measurements as predicted by the model can go up to 100%. In another embodiment, the receptor occupancy is sustained for at least one month after dosing. In another aspect, the receptor occupancy period is at least two months, alternatively at least three months, alternatively at least four months, alternatively at least five months. In aspects, the brain mu-opioid receptor occupancy can be measured by [11C]carfentanil Positron Emission Tomography scans (see Greenwald et al, Biological Psychiatry, 61:101-110 (2007), the disclosure of which is incorporated herein by reference). In aspects, μ-opioid receptor occupancy is the average of individual predicted values for μ-opioid receptor occupancy. In aspects, μ-opioid receptor occupancy is the predicted value for an average plasma concentration. In aspects, μ-opioid receptor occupancy is the predicted or observed value for a single patient. In aspects, the patient is administered Formulation A, Formulation B, Formulation C, Formulation D, or Formulation E, which comprise from about 295 mg to about 305 mg of buprenorphine (e.g., 300 mg buprenorphine free base), for at least twelve months. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods of treating opioid use disorder in an injection drug patient in need thereof by administering Formulation A, Formulation B, Formulation C, Formulation D, or Formulation E to the injection drug patient once per month to treat the opioid use disorder; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the opioid use disorder is mild opioid use disorder, moderate opioid use disorder, severe opioid use disorder, or moderate-to-severe opioid use disorder. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of reducing opioid craving and/or eliminating opioid craving in an injection drug patient in need thereof by administering Formulation A, Formulation B, Formulation C, Formulation D, or Formulation E to the injection drug patient once per month to reduce or eliminate opioid craving; wherein F Formulation A, Formulation B, Formulation C, Formulation D, or Formulation E Formulation D is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the methods are for reducing opioid craving. In aspects, the methods are for eliminating opioid craving. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of reducing opioid withdrawal symptoms and/or eliminating opioid withdrawal symptoms in an injection drug patient in need thereof by administering Formulation A, Formulation B, Formulation C, Formulation D, or Formulation E to the injection drug patient once per month to reduce or eliminate the opioid withdrawal symptoms; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the methods are for reducing opioid withdrawal symptoms. In aspects, the methods are for eliminating opioid withdrawal symptoms. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of reducing illicit opioid use or eliminating illicit opioid use in an injection drug patient in need thereof by administering Formulation A, Formulation B, Formulation C, Formulation D, or Formulation E to the injection drug patient once per month to induce opioid abstinence; wherein Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the methods comprise reducing illicit opioid use. In aspects the methods comprise eliminating illicit opioid use. In aspects, the methods further comprising maintaining opioid abstinence. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of inducing opioid abstinence in an injection drug patient in need thereof by administering Formulation A, Formulation B, Formulation C, Formulation D, or Formulation E to the injection drug patient once per month to induce opioid abstinence; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of maintaining opioid abstinence in an injection drug patient in need thereof by administering Formulation A, Formulation B, Formulation C, Formulation D, or Formulation E to the injection drug patient once per month to maintain opioid abstinence; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of treating opioid use disorder in an injection drug patient in need thereof by administering Formulation A, Formulation B, Formulation C, Formulation D, or Formulation E to the injection drug patient once per month to treat the opioid use disorder; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, the opioid use disorder is mild opioid use disorder, moderate opioid use disorder, or severe opioid use disorder. In aspects, the opioid use disorder is moderate-to-severe opioid use disorder. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene.

The disclosure provides methods of reducing opioid craving and/or eliminating opioid craving in an injection drug patient in need thereof by administering Formulation A, Formulation B, Formulation C, Formulation D, or Formulation E to the injection drug patient once per month to reduce and/or eliminate opioid craving; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, the methods are for reducing opioid craving. In aspects, the methods are for eliminating opioid craving. In aspects, the methods are for reducing opioid craving and for eliminating opioid craving. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene.

The disclosure provides methods of reducing opioid withdrawal symptoms and/or eliminating opioid withdrawal symptoms in an injection drug patient in need thereof by administering Formulation A, Formulation B, Formulation C, Formulation D, or Formulation E to the injection drug patient once per month to reduce and/or eliminate the opioid withdrawal symptoms; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, the methods are for reducing opioid withdrawal symptoms. In aspects, the methods are for eliminating opioid withdrawal symptoms. In aspects, the methods are for reducing opioid withdrawal symptoms, and for eliminating opioid withdrawal symptoms. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene.

The disclosure provides methods of reducing illicit opioid use or eliminating illicit opioid use in an injection drug patient in need thereof by parenterally administering Formulation A, Formulation B, Formulation C, Formulation D, or Formulation E to the injection drug patient once per month to induce opioid abstinence; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, Formulation A, Formulation B, Formulation C, Formulation D, or Formulation E is administered by subcutaneous injection. In aspects, the methods further comprising maintaining opioid abstinence. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene. In aspects, the methods are for reducing illicit opioid use. In aspects, the methods are for eliminating illicit opioid use.

The disclosure provides methods for maintaining opioid abstinence in an injection drug patient in need thereof by parenterally administering Formulation A, Formulation B, Formulation C, Formulation D, or Formulation E to the injection drug patient once per month to for maintaining opioid abstinence; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, the injection drug patient is black or African-American. In aspects, the injection drug patient has a TT genotype for SNP rs678849 on OPRD1 gene. In aspects, the injection drug patient has a TC genotype for SNP rs678849 on OPRD1 gene. In aspects, the injection drug patient is black or African-American with a TT genotype for SNP rs678849 on OPRD1 gene. In aspects, the injection drug patient is black or African-American with a TC genotype for SNP rs678849 on OPRD1 gene.

The disclosure provides methods of treating opioid use disorder in a black or African-American patient in need thereof by administering Formulation A, Formulation B, Formulation C, Formulation D, or Formulation E to the injection drug patient once per month to treat the opioid use disorder; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the opioid use disorder is mild opioid use disorder, moderate opioid use disorder, severe opioid use disorder, or moderate-to-severe opioid use disorder. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of reducing and/or eliminating opioid craving in a black or African-American patient in need thereof by administering Formulation A, Formulation B, Formulation C, Formulation D, or Formulation E to the injection drug patient once per month to reduce or eliminate opioid craving; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the methods are for reducing opioid craving. In aspects, the methods are for eliminating opioid craving. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of reducing and/or eliminating opioid withdrawal symptoms in a black or African-American patient in need thereof by administering Formulation A, Formulation B, Formulation C, Formulation D, or Formulation E to the injection drug patient once per month to reduce or eliminate the opioid withdrawal symptoms; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the methods are for reducing opioid withdrawal symptoms. In aspects, the methods are for eliminating opioid withdrawal symptoms. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of reducing illicit opioid use in a black or African-American patient in need thereof by administering Formulation A, Formulation B, Formulation C, Formulation D, or Formulation E to the injection drug patient once per month to induce opioid abstinence; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the methods further comprising maintaining opioid abstinence. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of eliminating illicit opioid use in a black or African-American patient in need thereof by administering Formulation A, Formulation B, Formulation C, Formulation D, or Formulation E to the injection drug patient once per month to induce opioid abstinence; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the methods further comprising maintaining opioid abstinence. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of inducing opioid abstinence in a black or African-American patient in need thereof by administering Formulation A, Formulation B, Formulation C, Formulation D, or Formulation E to the injection drug patient once per month to induce opioid abstinence; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of maintaining opioid abstinence in a black or African-American patient in need thereof by administering Formulation A, Formulation B, Formulation C, Formulation D, or Formulation E to the injection drug patient once per month to maintain opioid abstinence; wherein Formulation A, Formulation B, Formulation C, Formulation D, or Formulation E comprises about 300 mg buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient. In aspects, the methods comprise administering Formulation A. In aspects, the methods comprise administering Formulation B. In aspects, the methods comprise administering Formulation C. In aspects, the methods comprise administering Formulation D. In aspects, the methods comprise administering Formulation E.

The disclosure provides methods of treating opioid use disorder in a black or African-American patient in need thereof by administering Formulation A, Formulation B, Formulation C, Formulation D, or Formulation E to the injection drug patient once per month to treat the opioid use disorder; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, the opioid use disorder is mild opioid use disorder, moderate opioid use disorder, severe opioid use disorder, or moderate-to-severe opioid use disorder. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient.

The disclosure provides methods of reducing and/or eliminating opioid craving in a black or African-American patient in need thereof by administering Formulation A, Formulation B, Formulation C, Formulation D, or Formulation E to the injection drug patient once per month to reduce and/or eliminate opioid craving; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, the methods are for reducing opioid craving. In aspects, the methods are for eliminating opioid craving. In aspects, the methods are for reducing opioid craving and for eliminating opioid craving. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient.

The disclosure provides methods of reducing and/or eliminating opioid withdrawal symptoms in a black or African-American patient in need thereof by administering Formulation A, Formulation B, Formulation C, Formulation D, or Formulation E to the injection drug patient once per month to reduce and/or eliminate the opioid withdrawal symptoms; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, the methods are for reducing opioid withdrawal symptoms. In aspects, the methods are for eliminating opioid withdrawal symptoms. In aspects, the methods are for reducing opioid withdrawal symptoms, and for eliminating opioid withdrawal symptoms. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient.

The disclosure provides methods of reducing illicit opioid use in a black or African-American patient in need thereof by parenterally administering Formulation A, Formulation B, Formulation C, Formulation D, or Formulation E to the injection drug patient once per month to induce opioid abstinence; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, Formulation A, Formulation B, Formulation C, Formulation D, or Formulation E is administered by subcutaneous injection. In aspects, the methods further comprising maintaining opioid abstinence. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient.

The disclosure provides methods of eliminating illicit opioid use in a black or African-American patient in need thereof by parenterally administering Formulation A, Formulation B, Formulation C, Formulation D, or Formulation E to the injection drug patient once per month to induce opioid abstinence; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In aspects, Formulation A is administered. In aspects, Formulation B is administered. In aspects, Formulation C is administered. In aspects, Formulation D is administered. In aspects, Formulation E is administered. In aspects, Formulation A, Formulation B, Formulation C, Formulation D, or Formulation E is administered by subcutaneous injection. In aspects, the methods further comprising maintaining opioid abstinence. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient.

The disclosure provides methods for maintaining opioid abstinence in a black or African-American patient in need thereof by parenterally administering Formulation A, Formulation B, Formulation C, Formulation D, or Formulation E to the injection drug patient once per month to for maintaining opioid abstinence; wherein Formulation A, Formulation B, Formulation C, Formulation D, or Formulation E comprises from about 295 mg to about 305 mg buprenorphine; or from about 296 mg to about 304 mg buprenorphine; or from about 297 mg to about 303 mg buprenorphine; or from about 298 mg to about 302 mg buprenorphine; or from about 299 mg to about 301 mg buprenorphine; or about 300 mg buprenorphine. In aspects, the buprenorphine is buprenorphine free base. In aspects, Formulation A, Formulation B, Formulation C, Formulation D, or Formulation E is administered to the injection drug patient once per month for at least six months. In aspects, Formulation A, Formulation B, Formulation C, Formulation D, or Formulation E is administered to the injection drug patient once per month for at least twelve months. In aspects, Formulation A, Formulation B, Formulation C, Formulation D, or Formulation E is administered by subcutaneous injection. In one aspect, Formulation A is administered. In another aspect, Formulation B is administered. In other aspects, Formulation C is administered. In yet other aspects, Formulation D is administered. In aspects, the patient has a TT genotype for SNP rs678849 on OPRD1 gene. In aspects, the patient has a TC genotype for SNP rs678849 on OPRD1 gene. In aspects, the patent is an injection drug patient with a TT genotype for SNP rs678849 on OPRD1 gene. In aspects, the patient is an injection drug patient with a TC genotype for SNP rs678849 on OPRD1 gene. In aspects, the patient is an injection drug patient.

The disclosure provides methods for treating opioid dependence, reducing and/or eliminating opioid craving, reducing and/or eliminating opioid withdrawal symptoms, reducing and/or eliminating illicit opioid use, or a combination of two or more thereof, in a patient in need thereof by (a) administering a first composition of Formulation A, Formulation B, Formulation C, Formulation D, or Formulation E comprising buprenorphine to the patient once per month by injection for two months; and thereafter (b) administering a second composition of Formulation A, Formulation B, Formulation C, Formulation D, or Formulation E comprising buprenorphine to the patient once per month by injection beginning with the third month of administration and for each month thereafter for at least four months (such that step (a) is for 2 months, and step (b) is for at least for 4 months to provide a treatment period of at least 6 months or at least twelve months); wherein the amount of buprenorphine in the first composition is from about 295 mg to about 305 mg and the amount of buprenorphine in the second composition is from about 95 mg to about 105 mg. In some aspects, the amount of buprenorphine in the first composition is from about 296 mg to about 304 mg, alternatively from about 297 mg to about 303 mg, alternatively from about 298 mg to about 302 mg, alternatively from about 288 mg to about 301 and the amount of buprenorphine in the second composition is from about 96 mg to about 104 mg, alternatively from about 97 mg to about 103 mg, alternatively from about 98 mg to about 102 mg, alternatively from about 99 mg to about 101 mg. In aspects, the first composition comprises about 300 mg of buprenorphine, and the second composition comprises about 100 mg of buprenorphine. In aspects, the first and second compositions are Formulation A. In aspects, the first and second compositions are Formulation B. In aspects, the first and second compositions are Formulation C. In aspects, the first and second compositions are Formulation D. In aspects, the buprenorphine is buprenorphine free base. In aspects, the first composition is Formulation D containing about 300 mg of buprenorphine free base, and the second composition is Formulation D containing about 100 mg of buprenorphine free base. In aspects, the injections are subcutaneous injections. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid dependence, reducing and/or eliminating opioid craving, reducing and/or eliminating opioid withdrawal symptoms reducing and/or eliminating illicit opioid use, or a combination of two or more thereof, in a patient by administering a first composition of Formulation A, Formulation B, Formulation C, Formulation D, or Formulation E comprising from about 295 mg to about 305 mg of buprenorphine (e.g., 300 mg buprenorphine free base) for two months and thereafter administering a second composition of Formulation A, Formulation B, Formulation C, Formulation D, or Formulation E comprising from about 95 mg to about 105 mg of buprenorphine (e.g., 100 mg buprenorphine free base) for at least four months provide a steady-state average buprenorphine plasma concentration ($C_{avg}$) from about 2.6 ng/mL to about 3.6 ng/mL; or from about 2.7 ng/mL to about 3.5 ng/mL; or from about 2.8 ng/mL to about 3.4 ng/mL; or from about 2.9 ng/mL to about 3.3 ng/mL; or from about 3.0 ng/mL to about 3.2 ng/mL; or about 3.1 ng/mL. In aspects, the steady-state average buprenorphine plasma concentration ($C_{avg}$) is from about 2.5 ng/mL to about 4.0 ng/mL; or from about 2.7 ng/mL to about 3.7 ng/mL; or from about 2.8 ng/mL to about 3.6 ng/mL; or from about 2.9 ng/mL to about 3.5 ng/mL; or from about 3.0 ng/mL to about 3.4 ng/mL; or from about 3.1 ng/mL to about 3.3 ng/mL; or about 3.2 ng/mL. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid dependence, reducing and/or eliminating opioid craving, reducing and/or eliminating opioid withdrawal symptoms, reducing and/or eliminating illicit opioid use, or a combination of two or more thereof, in a patient by administering a first composition of Formulation A, Formulation B, Formulation C, Formulation D, or Formulation E comprising from about 295 mg to about 305 mg of buprenorphine (e.g., 300 mg buprenorphine free base) for two months and thereafter administering a second composition of Formulation A, Formulation B, Formulation C, Formulation D, or Formulation E comprising from about 95 mg to about 105 mg of buprenorphine (e.g., 100 mg buprenorphine free base) for at least four months provide a steady-state minimum buprenorphine plasma concentration ($C_{min}$) from about 2.2 ng/mL to about 2.9 ng/mL; or from about 2.3 ng/mL to about 2.9 ng/mL; or from about 2.4 ng/mL to about 2.9 ng/mL; or from about 2.5 ng/mL to about 2.9 ng/mL; or from about 2.6 ng/mL to about 2.9 ng/mL; or from about 2.7 ng/mL; to about 2.9 ng/mL; or from about 2.0 ng/mL to about 2.8 ng/mL; or from about 2.1 ng/mL to about 2.8 ng/mL; or from about 2.2 ng/mL to about 2.8 ng/mL; or from about 2.3 ng/mL to about 2.8 ng/mL; or from about 2.4 ng/mL to about 2.8 ng/mL; or from about 2.5 ng/mL to about 2.8 ng/mL; or from about 2.6 ng/mL to about 2.8 ng/mL; or from about 2.7 ng/mL; to about 2.8 ng/mL; or about 2.7 ng/mL; or about 2.73 ng/mL; or about 2.74 ng/mL; or about 2.75 ng/mL. In aspects, the steady-state minimum buprenorphine plasma concentration ($C_{min}$) is from about 2.0 ng/mL to about 3.0 ng/mL; or from about 2.1 ng/mL to about 2.9 ng/mL; or from about 2.2 ng/mL to about 2.8 ng/mL; or from about 2.3 ng/mL to about 2.7 ng/mL; or from about 2.4 ng/mL to about 2.6 ng/mL; or from about 2.4 ng/mL to about 2.5 ng/mL; or about 2.4 ng/mL; or about 2.5 ng/mL; or about 2.6 ng/mL. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

The disclosure provides methods for treating opioid dependence, reducing and/or eliminating opioid craving, reducing and/or eliminating opioid withdrawal symptoms, reducing and/or eliminating illicit opioid use, or a combination of two or more thereof, in a patient by administering a first composition of Formulation A, Formulation B, Formulation C, Formulation D, or Formulation E comprising from about 295 mg to about 305 mg of buprenorphine (e.g., 300 mg buprenorphine free base) for two months and thereafter administering a second composition of Formulation A, Formulation B, Formulation C, Formulation D, or Formulation E comprising from about 95 mg to about 105 mg of buprenorphine (e.g., 100 mg buprenorphine free base) for at least four months provide a steady-state maximum buprenorphine plasma concentration ($C_{max}$) about 3.6 ng/mL to about 4.6 ng/mL; about 3.7 ng/mL to about 4.5 ng/mL; about 3.8 ng/mL to about 4.4 ng/mL; about 3.9 ng/mL to about 4.3 ng/mL; from about 4.0 ng/mL to about 4.2 ng/mL; or about 4.1 ng/mL; or about 4.11 ng/mL; or about 4.12 ng/mL. In aspects, the steady-state maximum buprenorphine plasma concentration ($C_{max}$) is from about 4.0 ng/mL to about 6 ng/mL; or from about 4.3 ng/mL to about 5.5 ng/mL; or from about 4.4 ng/mL to about 5.4 ng/mL; or from about 4.5 ng/mL to about 5.3 ng/mL; or from about 4.6 ng/mL to about 5.2 ng/mL; or from about 4.7 ng/mL to about 5.1 ng/mL; or from about 4.8 ng/mL to about 5.0 ng/mL; or about 4.8 ng/mL; or about 4.9 ng/mL; or about 5.0 ng/mL. In aspects, the patient is an injection drug patient. In aspects, the patient is black or African-American. In aspects, the patient is a black or African-American injection drug patient. In aspects, the patient has a TT genotype for SNP rs678849 on OPRD1 gene. In aspects, the patient has a TC genotype for SNP rs678849 on OPRD1 gene. In aspects, the patient is an injection drug patient with a TT genotype for SNP rs678849 on OPRD1 gene. In aspects, the patient is an injection drug patient with a TC genotype for SNP rs678849 on OPRD1 gene. In aspects, the patient is black or African-American with a TT genotype for SNP rs678849 on OPRD1 gene. In aspects, the patient is black or African-American with a TC genotype for SNP rs678849 on OPRD1 gene. In aspects, the patient is a black or African-American injection drug patient with a TT genotype for SNP rs678849 on OPRD1 gene. In aspects, the patient is a black or African-American injection drug patient with a TC genotype for SNP rs678849 on OPRD1 gene.

Methods for making the sustained-release buprenorphine formulations described herein are known in the art and described, for example, in U.S. Pat. Nos. 8,921,387, 8,975,270, 9,272,044, 9,498,432, 9,782,402, 9,827,241, and WO 2016/071767, the disclosures of which are incorporated by reference herein in their entirety.

Embodiments P1-P65

Embodiment P1

A method treating opioid use disorder, reducing opioid craving, eliminating opioid craving, reducing opioid withdrawal symptoms, eliminating opioid withdrawal symptoms, reducing illicit opioid use, eliminating illicit opioid use, or a combination of two or more thereof, in an injection drug patient in need thereof, the method comprising administering to the injection drug patient a composition of Formulation A, Formulation B, Formulation C, Formulation D, or Formulation E once per month; wherein Formulation A, Formulation B, Formulation C, Formulation D, or Formulation E comprises about 300 mg buprenorphine.

Embodiment P2

A method treating opioid use disorder, reducing opioid craving, eliminating opioid craving, reducing opioid withdrawal symptoms, eliminating opioid withdrawal symptoms, reducing illicit opioid use, eliminating illicit opioid use, or a combination of two or more thereof, in an injection drug patient in need thereof, the method comprising: (i) administering to the injection drug patient a composition of Formulation A, Formulation B, Formulation C, Formulation D, or Formulation E once per month for two months; wherein Formulation A, Formulation B, Formulation C, Formulation D, or Formulation E comprises about 300 mg buprenorphine; and thereafter (ii) administering to the injection drug patient a composition of Formulation A, Formulation B, Formulation C, Formulation D, or Formulation E once per month for at least four months; wherein Formulation A, Formulation B, Formulation C, Formulation D, or Formulation E comprises about 100 mg buprenorphine.

Embodiment P3

The method of Embodiment 1 or 2, comprising administering the composition of Formulation A.

Embodiment P4

The method of Embodiment 1 or 2, comprising administering the composition of Formulation B.

Embodiment P5

The method of Embodiment 1 or 2, comprising administering the composition of Formulation C.

Embodiment P6

The method of Embodiment 1 or 2, comprising administering the composition of Formulation D.

Embodiment P7

The method of any one of Embodiments 1 to 6, comprising subcutaneously administering the composition.

Embodiment P8

The method of any one of Embodiments 1 to 7, comprising administering the composition once per month.

Embodiment P9

The method of any one of Embodiments 1 to 8, comprising administering the composition once per month for at least six months.

Embodiment P10

The method of any one of Embodiments 1 to 9 for treating opioid use disorder.

Embodiment P11

The method of Embodiment 10, wherein the opioid use disorder is moderate-to-severe opioid use disorder.

Embodiment P12

The method of Embodiment 10, wherein the opioid use disorder is moderate opioid use disorder.

Embodiment P13

The method of Embodiment 10, wherein the opioid use disorder is severe opioid use disorder.

Embodiment P14

The method of Embodiment 10, wherein the opioid use disorder is mild opioid use disorder.

Embodiment P15

The method of any one of Embodiments 1 to 9 for reducing opioid craving.

Embodiment P16

The method of any one of Embodiments 1 to 9 for eliminating opioid craving.

Embodiment P17

The method of any one of Embodiments 1 to 9 for reducing opioid withdrawal symptoms.

Embodiment P18

The method of any one of Embodiments 1 to 9 for eliminating opioid withdrawal symptoms.

Embodiment P19

The method of any one of Embodiments 1 to 9 for reducing illicit opioid use.

Embodiment P20

The method of any one of Embodiments 1 to 9 for preventing illicit opioid use.

Embodiment P21

The method of Embodiment 19, further comprising maintaining abstinence.

Embodiment P22

The method of any one of Embodiments 1 to 21, wherein the injection drug patient is an intravenous injection drug patient.

Embodiment P23

The method of any one of Embodiments 1 to 21, wherein the injection drug patient is an intramuscular injection drug patient.

Embodiment P24

The method of any one of claims 1 to 21, wherein the injection drug patient is a subcutaneous injection drug patient.

Embodiment P25

The method of any one of Embodiments 1 to 24, wherein the patient is black.

Embodiment P26

The method of any one of Embodiments 1 to 25, wherein the patient has a TC genotype for SNP rs678849 on OPRD1 gene.

Embodiment P27

The method of any one of Embodiments 1 to 25, wherein the patient has a TT genotype for SNP rs678849 on OPRD1 gene.

Embodiment P28

A method for treating opioid use disorder, reducing opioid craving, eliminating opioid craving, reducing opioid withdrawal symptoms, eliminating opioid withdrawal symptoms, reducing illicit opioid use, eliminating illicit opioid use, or a combination of two or more thereof in a patient in need thereof, the method comprising administering Formulation D to the patient once per month for at least six months; wherein Formulation D comprises about 300 mg buprenorphine free base; and wherein the method produces a steady-state average buprenorphine plasma concentration from about 5.5 ng/mL to about 7.5 ng/mL.

Embodiment P29

The method of Embodiment 28, wherein the steady-state average buprenorphine plasma concentration is from about 6.0 ng/mL to about 7.0 ng/mL.

Embodiment P30

The method of Embodiment 28, wherein the steady-state average buprenorphine plasma concentration is from 6.1 ng/mL to about 7.0 ng/mL.

Embodiment P31

The method of Embodiment 28, wherein the steady-state average buprenorphine plasma concentration is from 6.2 ng/mL to about 7.0 ng/mL.

Embodiment P32

The method of Embodiment 28, wherein the steady-state average buprenorphine plasma concentration is about 6.3 ng/mL.

Embodiment P33

A method for treating opioid use disorder, reducing opioid craving, eliminating opioid craving, reducing opioid withdrawal symptoms, eliminating opioid withdrawal symptoms, reducing illicit opioid use, eliminating illicit opioid use, or a combination of two or more thereof in a patient in need thereof, the method comprising administering Formulation D to the patient once per month for at least six months; wherein Formulation D comprises about 300 mg buprenorphine free base; and wherein the method produces a steady-state minimum buprenorphine plasma concentration from about 5.0 ng/mL to about 5.2 ng/mL; a steady-state average buprenorphine plasma concentration from about 6.2 ng/mL to about 6.4 ng/mL; and a steady-state maximum buprenorphine plasma concentration from about 8 ng/mL to about 9 ng/mL.

Embodiment P34

The method of Embodiment 33, wherein the steady-state average minimum buprenorphine plasma concentration is at least 5.1 ng/mL; the steady-state average buprenorphine plasma concentration is about 6.3 ng/mL; and the steady-state maximum buprenorphine plasma concentration is about 8.7 ng/mL.

Embodiment P35

The method of any one of Embodiments 28 to 34, wherein the steady-state buprenorphine plasma concentration is achieved after 5 months.

Embodiment P36

The method of any one of Embodiments 28 to 34, wherein the steady-state buprenorphine plasma concentration is achieved after 6 months.

Embodiment P37

The method of any one of Embodiments 28 to 34, wherein the method produces a mu-opioid receptor occupancy of at least 70%, as measured by Equation 1, after the first administration of Formulation D, and produces an average steady-state mu-opioid receptor occupancy of at least 83%, as measured by Equation 1, after further five administrations of Formulation D.

Embodiment P38

The method of Embodiment 37, wherein the steady-state mu-opioid receptor occupancy is produced after six total administrations of Formulation D.

Embodiment P39

The method of any one of Embodiments 28 to 38, comprising administering Formulation D by subcutaneous injection.

Embodiment P40

The method of any one of Embodiments 28 to 38, further comprising obtaining a blood sample from the patient; and measuring the buprenorphine plasma concentration in the blood sample.

Embodiment P41

The method of any one of Embodiments 28 to 40 for reducing opioid craving.

Embodiment P42

The method of any one of Embodiments 28 to 40 for eliminating opioid craving.

Embodiment P43

The method of any one of Embodiments 28 to 40 for reducing opioid withdrawal symptoms.

Embodiment P44

The method of any one of Embodiments 28 to 40 for eliminating opioid withdrawal symptoms.

Embodiment P45

The method of any one of Embodiments 28 to 40 for treating opioid use disorder.

Embodiment P46

The method of Embodiment 45, wherein the opioid use disorder is moderate-to-severe opioid use disorder.

Embodiment P47

The method of Embodiment 45, wherein the opioid use disorder is moderate opioid use disorder.

Embodiment P48

The method of Embodiment 45, wherein the opioid use disorder is severe opioid use disorder.

Embodiment P49

The method of Embodiment 45, wherein the opioid use disorder is mild opioid use disorder.

Embodiment P50

The method of any one of Embodiments 28 to 40 for reducing illicit opioid use.

Embodiment P51

The method of any one of Embodiments 28 to 40 for preventing illicit opioid use.

Embodiment P52

The method of any one of Embodiments 28 to 51, wherein the patient is an injection drug patient.

Embodiment P53

The method of Embodiment 52, wherein the injection drug patient is an intravenous injection drug patient.

Embodiment P54

The method of Embodiment 52, wherein the injection drug patient is an intramuscular injection drug patient.

Embodiment P55

The method of Embodiment 52, wherein the injection drug patient is a subcutaneous injection drug patient.

Embodiment P56

A method for treating opioid use disorder, reducing opioid craving, eliminating opioid craving, reducing opioid withdrawal symptoms, eliminating opioid withdrawal symptoms, reducing illicit opioid use, eliminating illicit opioid use in a patient in need thereof, the method comprising administering Formulation D300 to the patient once per month for two months, and thereafter administering Formulation D100 to the patient once per month for at least four months; wherein Formulation D300 comprises about 300 mg buprenorphine free base; wherein Formulation D100 comprises about 100 mg buprenorphine free base; and wherein the method produces a steady-state average buprenorphine plasma concentration from about 3.0 ng/mL to about 3.3 ng/mL.

Embodiment P57

The method of Embodiment 56, wherein the buprenorphine plasma concentration is from about 3.0 ng/mL to about 3.2 ng/mL.

Embodiment P58

A method for treating opioid use disorder, reducing opioid craving, eliminating opioid craving, reducing opioid withdrawal symptoms, eliminating opioid withdrawal symptoms, reducing illicit opioid use, eliminating illicit opioid use, maintaining abstinence, or a combination of two or more thereof in a patient in need thereof, the method comprising administering Formulation D300 to the patient once per month for two months, and thereafter administering Formulation D100 to the patient once per month for at least four months; wherein Formulation D300 comprises about 300 mg buprenorphine free base; wherein Formulation D100 comprises about 100 mg buprenorphine free base; and wherein the method produces a steady-state minimum buprenorphine plasma concentration from about 2.0 ng/mL to about 2.9 ng/mL; a steady-state average buprenorphine plasma concentration from about 3.0 ng/mL to about 3.3 ng/mL; and a steady-state maximum buprenorphine plasma concentration from about 3.9 ng/mL to about 4.3 ng/mL.

Embodiment P59

The method of any one of Embodiments 56 to 58, wherein the steady-state buprenorphine plasma concentration is achieved after 6 months.

Embodiment P60

The method of any one of Embodiments 56 to 59, wherein the method produces a mu-opioid receptor occupancy of at least 70%, as measured by Equation 1, after the first administration of Formulation D300, and produces an average steady-state mu-opioid receptor occupancy of at least 75%, as measured by Equation 1, after six months of administration.

Embodiment P61

The method of any one of Embodiments 56 to 60, comprising administering Formulation D300 and Formulation D100 by subcutaneous injection.

Embodiment P62

The method of any one of Embodiments 56 to 61, further comprising obtaining a blood sample from the patient; and measuring the buprenorphine plasma concentration in the blood sample.

Embodiment P63

The method of any one of Embodiments 28 to 62, wherein the patient has a TC genotype for SNP rs678849 on OPRD1 gene.

Embodiment P64

The method of any one of Embodiments 28 to 62, wherein the patient has a TT genotype for SNP rs678849 on OPRD1 gene.

Embodiment P65

The method of any one of Embodiments 28 to 64, wherein the patient is black.

Embodiments 1-93

Embodiment 1

A method of treating moderate-to-severe opioid use disorder in an injection drug patient in need thereof, the method comprising subcutaneously administering a buprenorphine composition once per month for at least six months to the injection drug patient; wherein the buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone.

Embodiment 2

The method of Embodiment 1, comprising subcutaneously administering the buprenorphine composition once per month for at least twelve months.

Embodiment 3

The method of Embodiment 1 or 2, wherein the method produces opioid abstinence in the injection drug user.

Embodiment 4

A method of treating opioid use disorder in an injection drug patient in need thereof, the method comprising subcutaneously administering to the injection drug patient a buprenorphine composition once per month for at least six months to the injection drug patient; wherein the buprenorphine composition comprises about 300 mg buprenorphine free base, a poly(lactide-co-glycolide) copolymer, and N-methyl-2-pyrrolidone.

Embodiment 5

The method of Embodiment 4, wherein the opioid use disorder is moderate-to-severe opioid use disorder.

Embodiment 6

The method of Embodiment 4, wherein the opioid use disorder is moderate opioid use disorder.

Embodiment 7

The method of Embodiment 4, wherein the opioid use disorder is severe opioid use disorder.

Embodiment 8

The method of Embodiment 4, wherein the method of treating opioid use disorder is a method of reducing opioid craving, a method of eliminating opioid craving, a method of reducing opioid withdrawal symptoms, a method of eliminating opioid withdrawal symptoms, a method of reducing illicit opioid use, a method of eliminating illicit opioid use, or a combination of two or more thereof.

Embodiment 9

The method of any one of Embodiments 4 to 8, wherein the buprenorphine composition comprises: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone.

Embodiment 10

The method of any one of Embodiments 4 to 8, wherein the buprenorphine composition comprises: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone.

Embodiment 11

The method of any one of Embodiments 4 to 8, wherein the buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone.

Embodiment 12

The method of any one of Embodiments 4 to 11, comprising subcutaneously administering the buprenorphine composition once per month for at least twelve months.

Embodiment 13

The method of any one of Embodiments 4 to 12, wherein the method produces opioid abstinence in the injection drug user.

Embodiment 14

The method of any one of Embodiments 8 to 13, for reducing opioid craving.

Embodiment 15

The method of any one of Embodiments 8 to 13, for eliminating opioid craving.

Embodiment 16

The method of any one of Embodiments 8 to 13, for reducing opioid withdrawal symptoms.

Embodiment 17

The method of any one of Embodiments 8 to 13, for eliminating opioid withdrawal symptoms.

Embodiment 18

The method of any one of Embodiments 8 to 13, for reducing illicit opioid use.

Embodiment 19

The method of any one of Embodiments 6 to 11, for eliminating illicit opioid use.

Embodiment 20

The method of any one of Embodiments 1 to 19, wherein the injection drug patient is an intravenous injection drug patient.

Embodiment 21

The method of any one of Embodiments 1 to 19, wherein the injection drug patient is an intramuscular injection drug patient.

Embodiment 22

The method of any one of Embodiments 1 to 19, wherein the injection drug patient is a subcutaneous injection drug patient.

Embodiment 23

The method of any one of Embodiments 1 to 22, wherein the injection drug patient has a TC genotype for SNP rs678849 on OPRD1 gene.

Embodiment 24

The method of any one of Embodiments 1 to 22, wherein the injection drug patient has a TT genotype for SNP rs678849 on OPRD1 gene.

Embodiment 25

The method of any one of Embodiments 1 to 24, wherein the injection drug patient is black.

Embodiment 26

A method of treating opioid use disorder in a patient in need thereof, the method comprising the steps, in order, of: (i) subcutaneously administering a first buprenorphine composition to the patient once per month for two months; wherein the first buprenorphine composition comprises about 300 mg buprenorphine free base, a poly(lactide-co-glycolide) copolymer, and N-methyl-2-pyrrolidone; and thereafter: (ii) subcutaneously administering a second buprenorphine composition to the patient once per month for at least one month; wherein the second buprenorphine composition comprises about 100 mg buprenorphine free base, a poly(lactide-co glycolide) copolymer, and N-methyl-2-pyrrolidone; and thereafter: (iii) detecting illicit opioid use, opioid craving, or opioid withdrawal symptoms in the patient; and thereafter (iv) subcutaneously administering a third buprenorphine composition to the patient once per month for at least one month; wherein the third buprenorphine composition comprises about 300 mg buprenorphine free base, a poly(lactide-co-glycolide) copolymer, and N-methyl-2-pyrrolidone.

Embodiment 27

The method of Embodiment 26, wherein step (iii) comprises detecting illicit opioid use in the patient.

Embodiment 28

The method of Embodiment 27, wherein detecting illicit opioid use comprises self-reporting of illicit opioid use by the patient.

Embodiment 29

The method of Embodiment 27, wherein detecting illicit opioid use comprises detecting a positive urine drug screen for an illicit opioid.

Embodiment 30

The method of Embodiment 26, wherein step (iii) comprises detecting opioid craving in the patient.

Embodiment 31

The method of Embodiment 30, wherein detecting opioid craving comprises detecting a buprenorphine plasma concentration of less than 4 ng/mL in the patient.

Embodiment 32

The method of Embodiment 26, wherein step (iii) comprises detecting the opioid withdrawal symptom in the patient.

Embodiment 33

The method of Embodiment 32, wherein detecting opioid withdrawal symptoms comprises detecting a buprenorphine plasma concentration of less than 4 ng/mL in the patient.

Embodiment 34

A method of treating opioid use disorder in a patient in need thereof, the method comprising the steps, in order, of: (i) subcutaneously administering a first buprenorphine composition to the patient once per month for two months; wherein the first buprenorphine composition comprises about 300 mg buprenorphine free base, a poly(lactide-co-glycolide) copolymer, and N-methyl-2-pyrrolidone; and thereafter: (ii) subcutaneously administering a second buprenorphine composition to the patient once per month for at least one month; wherein the second buprenorphine composition comprises about 100 mg buprenorphine free base, a poly(lactide-co glycolide) copolymer, and N-methyl-2-pyrrolidone; and thereafter: (iii) detecting a buprenorphine plasma concentration of less than 4 ng/mL in the patient; and thereafter: (iv) subcutaneously administering a third buprenorphine composition to the patient once per month for at least one month; wherein the third buprenorphine composition comprises about 300 mg buprenorphine free base, a poly(lactide-co-glycolide) copolymer, and N-methyl-2-pyrrolidone.

Embodiment 35

The method of any one of Embodiments 26 to 34, wherein step (ii) comprises subcutaneously administering the second buprenorphine composition to the patient once per month for one month to twenty-four months.

Embodiment 36

The method of any one of Embodiment 26 to 35, wherein the opioid use disorder is moderate-to-severe opioid use disorder.

Embodiment 37

The method of any one of Embodiment 26 to 35, wherein the opioid use disorder is moderate opioid use disorder.

Embodiment 38

The method of any one of Embodiment 26 to 35, wherein the opioid use disorder is severe opioid use disorder.

Embodiment 39

The method of any one of Embodiment 26 to 35, wherein the method of treating opioid use disorder is a method of reducing opioid craving, a method of eliminating opioid craving, a method of reducing opioid withdrawal symptoms, a method of eliminating opioid withdrawal symptoms, a method of reducing illicit opioid use, a method of eliminating illicit opioid use, or a combination of two or more thereof.

Embodiment 40

The method of any one of Embodiments 26 to 39, wherein the first buprenorphine composition and the third buprenorphine composition comprise: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone; and wherein the second buprenorphine composition comprises: (i) about 100 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone.

Embodiment 41

The method of any one of Embodiments 26 to 39, wherein the first buprenorphine composition and the third buprenorphine composition comprise: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone; and wherein the second buprenorphine composition comprises: (i) about 100 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone.

Embodiment 42

The method of any one of Embodiments 26 to 39, wherein the first buprenorphine composition and the third buprenorphine composition comprise: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone; and wherein the second buprenorphine composition comprises: (i) about 100 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone.

Embodiment 43

The method of any one of Embodiments 39 to 42, for reducing opioid craving.

Embodiment 44

The method of any one of Embodiments 39 to 42, for eliminating opioid craving.

Embodiment 45

The method of any one of Embodiments 39 to 42, for reducing opioid withdrawal symptoms.

Embodiment 46

The method of any one of Embodiments 39 to 42, for eliminating opioid withdrawal symptoms.

Embodiment 47

The method of any one of Embodiments 39 to 42, for reducing illicit opioid use.

Embodiment 48

The method of any one of Embodiments 39 to 42, for eliminating illicit opioid use.

Embodiment 49

The method of any one of Embodiments 26 to 48, wherein the patient is an injection drug patient.

Embodiment 50

The method of Embodiment 49, wherein the injection drug patient is an intravenous injection drug patient, an intramuscular injection drug patient, or a subcutaneous injection drug patient.

Embodiment 51

The method of any one of Embodiments 26 to 50, wherein the patient has a TC genotype for SNP rs678849 on OPRD1 gene.

Embodiment 52

The method of any one of Embodiments 26 to 50, wherein the patient has a TT genotype for SNP rs678849 on OPRD1 gene.

Embodiment 53

The method of any one of Embodiments 26 to 52, wherein the patient is black.

Embodiment 54

A method of treating opioid use disorder in a patient having a TC genotype for SNP rs678849 on OPRD1 gene or a TT genotype for SNP rs678849 on OPRD1 gene in need thereof, the method comprising subcutaneously administering a buprenorphine composition to the patient once per month; wherein the buprenorphine composition comprises about 100 mg buprenorphine free base, a poly(lactide-co-glycolide) copolymer, and N-methyl-2-pyrrolidone.

Embodiment 55

The method of Embodiment 54, comprising subcutaneously administering the buprenorphine composition to the patient once per month for at least twelve months.

Embodiment 56

The method of Embodiment 54 or 55, wherein the opioid use disorder is moderate-to-severe opioid use disorder.

Embodiment 57

The method of Embodiment 54 or 55, wherein the opioid use disorder is moderate opioid use disorder.

Embodiment 58

The method of Embodiment 54 or 55, wherein the opioid use disorder is severe opioid use disorder.

Embodiment 59

The method of Embodiment 54 or 55, wherein the method of treating opioid use disorder is a method of reducing opioid craving, a method of eliminating opioid craving, a method of reducing opioid withdrawal symptoms, a method of eliminating opioid withdrawal symptoms, a method of reducing illicit opioid use, a method of eliminating illicit opioid use, or a combination of two or more thereof.

Embodiment 60

The method of any one of Embodiments 54 to 59, wherein the buprenorphine composition comprises: (i) about 100 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone.

Embodiment 61

The method of any one of Embodiments 54 to 59, wherein the buprenorphine composition comprises: (i) about 100 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone.

Embodiment 62 wherein the buprenorphine composition comprises: (i) about 100 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone.

Embodiment 63

The method of any one of Embodiments 59 to 62, for reducing opioid craving.

Embodiment 64

The method of any one of Embodiments 59 to 62, for eliminating opioid craving.

Embodiment 65

The method of any one of Embodiments 59 to 62, for reducing opioid withdrawal symptoms.

Embodiment 66

The method of any one of Embodiments 59 to 62, for eliminating opioid withdrawal symptoms.

Embodiment 67

The method of any one of Embodiments 59 to 62, for reducing illicit opioid use.

Embodiment 68

The method of any one of Embodiments 59 to 62, for eliminating illicit opioid use.

Embodiment 69

The method of any one of Embodiments 54 to 68, wherein the patient is an injection drug patient.

Embodiment 70

The method of Embodiment 69, wherein the injection drug patient is an intravenous injection drug patient, an intramuscular injection drug patient, or a subcutaneous injection drug patient.

Embodiment 71

The method of any one of Embodiments 54 to 70, wherein the patient is black.

Embodiment 72

The method of any one of Embodiments 54 to 71, wherein the patient has the TC genotype for SNP rs678849 on OPRD1 gene.

Embodiment 73

The method of any one of Embodiments 54 to 71, wherein the patient has the TT genotype for SNP rs678849 on OPRD1 gene.

Embodiment 74

A method of treating opioid use disorder in a patient in need thereof, the method comprising the steps, in order, of: (i) subcutaneously administering a first buprenorphine composition to the patient once per month for one month or two months; wherein the first buprenorphine composition comprises about 300 mg buprenorphine free base, a poly(lactide-co-glycolide) copolymer, and N-methyl-2-pyrrolidone; and thereafter: (ii) identifying the patient as having a TC genotype for SNP rs678849 on OPRD1 gene or a TT genotype for SNP rs678849 on OPRD1 gene; and thereafter (iii) subcutaneously administering a second buprenorphine composition to the patient once per month; wherein the second buprenorphine composition comprises about 100 mg buprenorphine free base, a poly(lactide-co-glycolide) copolymer, and N-methyl-2-pyrrolidone.

Embodiment 75

The method of Embodiment 74, wherein step (i) comprises subcutaneously administering the first buprenorphine composition to the patient once per month for one month.

Embodiment 76

The method of Embodiment 74 or 75, wherein the opioid use disorder is moderate-to-severe opioid use disorder.

Embodiment 77

The method of Embodiment 74 or 75, wherein the opioid use disorder is moderate opioid use disorder.

Embodiment 78

The method of Embodiment 74 or 75, wherein the opioid use disorder is severe opioid use disorder.

Embodiment 79

The method of Embodiments 74 or 75, wherein the method of treating opioid use disorder is a method of reducing opioid craving, a method of eliminating opioid craving, a method of reducing opioid withdrawal symptoms, a method of eliminating opioid withdrawal symptoms, a method of reducing illicit opioid use, a method of eliminating illicit opioid use, or a combination of two or more thereof.

Embodiment 80

The method of any one of Embodiments 74 to 79, wherein the first buprenorphine composition comprises: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone; and wherein the second buprenorphine composition comprises: (i) about 100 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons.

Embodiment 81

The method of any one of Embodiments 74 to 79, wherein the first buprenorphine composition comprises: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone; and wherein the second buprenorphine composition comprises: (i) about 100 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone.

Embodiment 82

The method of any one of Embodiments 74 to 79, wherein the first buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone; and wherein the second buprenorphine composition comprises: (i) about 100 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone.

Embodiment 83

The method of any one of Embodiments 79 to 82, for reducing opioid craving.

Embodiment 84

The method of any one of Embodiments 79 to 82, for eliminating opioid craving.

Embodiment 85

The method of any one of Embodiments 79 to 82, for reducing opioid withdrawal symptoms.

Embodiment 86

The method of any one of Embodiments 79 to 82, for eliminating opioid withdrawal symptoms.

Embodiment 87

The method of any one of Embodiments 79 to 82, for reducing illicit opioid use.

Embodiment 88

The method of any one of Embodiments 79 to 82, for eliminating illicit opioid use.

Embodiment 89

The method of any one of Embodiments 74 to 88, wherein the patient is an injection drug patient.

Embodiment 90

The method of Embodiment 89, wherein the injection drug patient is an intravenous injection drug patient, an intramuscular injection drug patient, or a subcutaneous injection drug patient.

Embodiment 91

The method of any one of Embodiments 74 to 90, wherein the patient is black.

Embodiment 92

The method of any one of Embodiments 74 to 91, wherein the patient has the TC genotype for SNP rs678849 on OPRD1 gene.

Embodiment 93

The method of any one of Embodiments 74 to 91, wherein the patient has the TT genotype for SNP rs678849 on OPRD1 gene.

EXAMPLES

The following examples are for illustrative purposes and are not intended to limit the scope of the claims or the disclosure.

Example 1

A 6 month, double-blind, placebo-controlled, Phase 3 clinical study (NCT02357901) was conducted to test two different dosage regimens of Formulation D on patients seeking treatment for opioid use disorder. Formulation D300 (Formulation D containing 300 mg buprenorphine free base) and Formulation D100 (Formulation D containing 100 mg buprenorphine free base) were used. After screening, all patients went through a 3 day induction phase using SUBOXONE® film, followed by a 4-11 day stabilization phase using SUBOXONE® film. After the induction and stabilization phases, patients were randomized to three groups.

Patient Group 1 (n=194 patients) was administered Formulation D300 on Month 1 (Day 1) and Month 2 (Day 29), and was subsequently administered Formulation D100 on Month 3 (Day 57), Month 4 (Day 85), Month 5 (Day 113), and Month 6 (Day 141). Formulation D300 contained about 300 mg buprenorphine free base, and Formulation D100 contained about 100 mg buprenorphine free base. This dosing regimen is also referred to as 300 mg/100 mg (i.e., 300 mg for the first two months, and 100 mg for the subsequent four months).

Patient Group 2 (n=196 patients) was administered Formulation D300 on Month 1 (Day 1), Month 2 (Day 29), Month 3 (Day 57), Month 4 (Day 85), Month 5 (Day 113), and Month 6 (Day 141). Formulation D300 contained about 300 mg buprenorphine free base. This dosing regimen is also referred to as 300 mg/300 mg (i.e., 300 mg for the first two months, and 300 mg for the subsequent four months).

Patient Group 3 (n=99) was administered a placebo on Month 1 (Day 1), Month 2 (Day 29), Month 3 (Day 57), Month 4 (Day 85), Month 5 (Day 113), and Month 6 (Day 141).

Each Patient Group received individual drug counseling (IDC) during the course of the study. Through the course of the study, each Patient Group provided a weekly urine sample for opioid testing. The primary measure of efficacy was assessed by centrally tested urine drug screening (UDS) results and self-reported illicit opioid use. Additionally, scores for Opioid Craving VAS, COWS and SOWS were assessed.

Urine drug screens and self-reports were assessed at screening, and then on a weekly basis following each subcutaneous injection of Formulation D or placebo (Days 1, 8, 15, 22, 29, 36, 43, 50, 57, 64, 71, 78, 85, 92, 99, 106, 113, 120, 127, 134, 141, 148, 155, 162 and 169), as well as at a safety follow-up visit (Day 197). Urine drug screens were also assessed on the day after each subcutaneous injection at 24 hours post-dose (Days 2, 30, 58, 86, 114 and 142).

Figure 2:
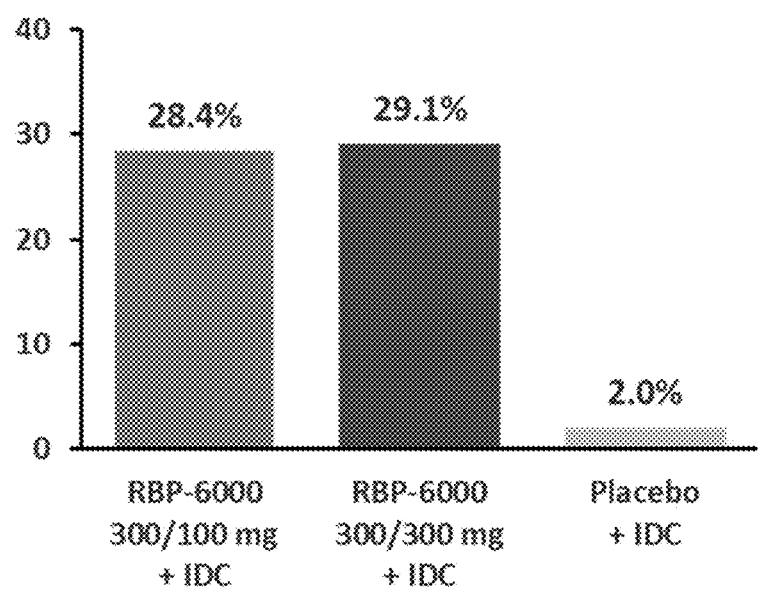
FIG. 2 shows the percentage of patients who had at least 80% of their weekly urine samples negative for illicit opioids combined with self-reports negative for illicit opioid use from Weeks 5 to 24 of the study. The treatment program included IDC.

The results of the urine drug screens and self-reports are shown in FIG. 1 and FIG. 2. FIG. 2 shows that about 28.4% of the patients in Group 1 and 29.1% of the patients in Group 2 had at least 80% negative urine samples for illicit opioids combined with negative self-reports of illicit opioid use from Weeks 5 to 24 in the study. In contrast, only about 2% of the patients in the placebo group had at least 80% negative urine samples for illicit opioids combined with negative self-reports of illicit opioid use from Weeks to 5 to 24 in the study.

Scores for Opioid Craving VAS, COWS and SOWS were measured at the same times as the urine drug samples (with the exception of the follow-up visit on Day 197). Opioid craving was additionally measured during the dose-adjustment period with SUBOXONE® film. (Days −8, −4 and/or −1). The COWS and SOWS scores were measured during both induction and dose adjustment with SUBOXONE film (Days −14, −13, −12, −11, −8, −4 and/or −1).

Figure 3:
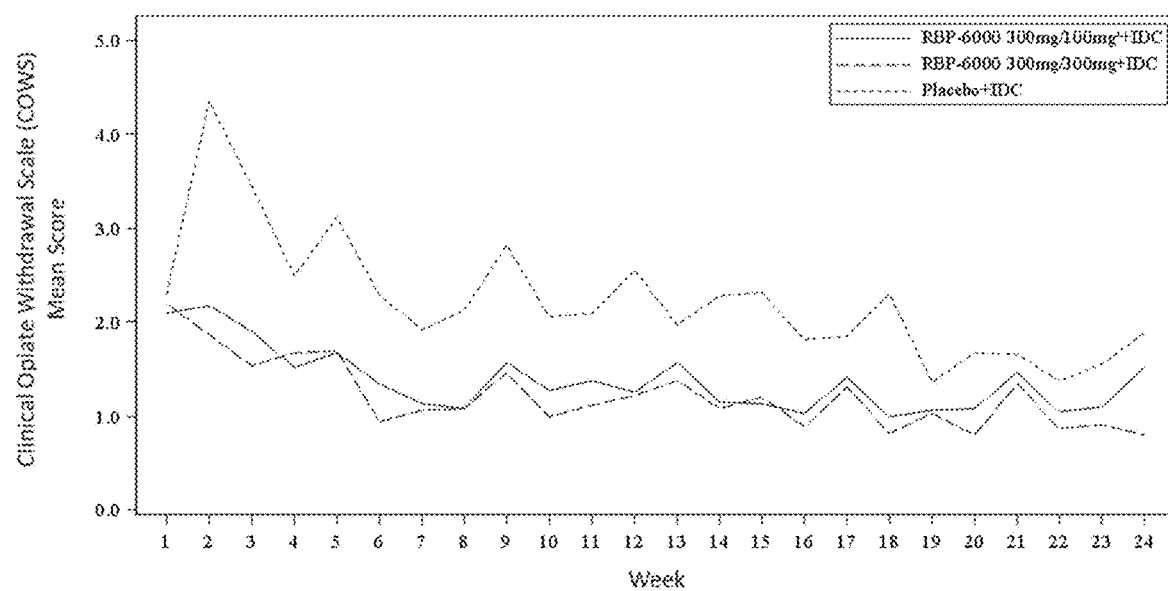
FIG. 3 shows the mean Clinical Opiate Withdrawal Scale (COWS) score over time for the clinical study described in the Example. The x-axis shows time in weeks. The y-axis shows the COWS mean score.
Figure 4:
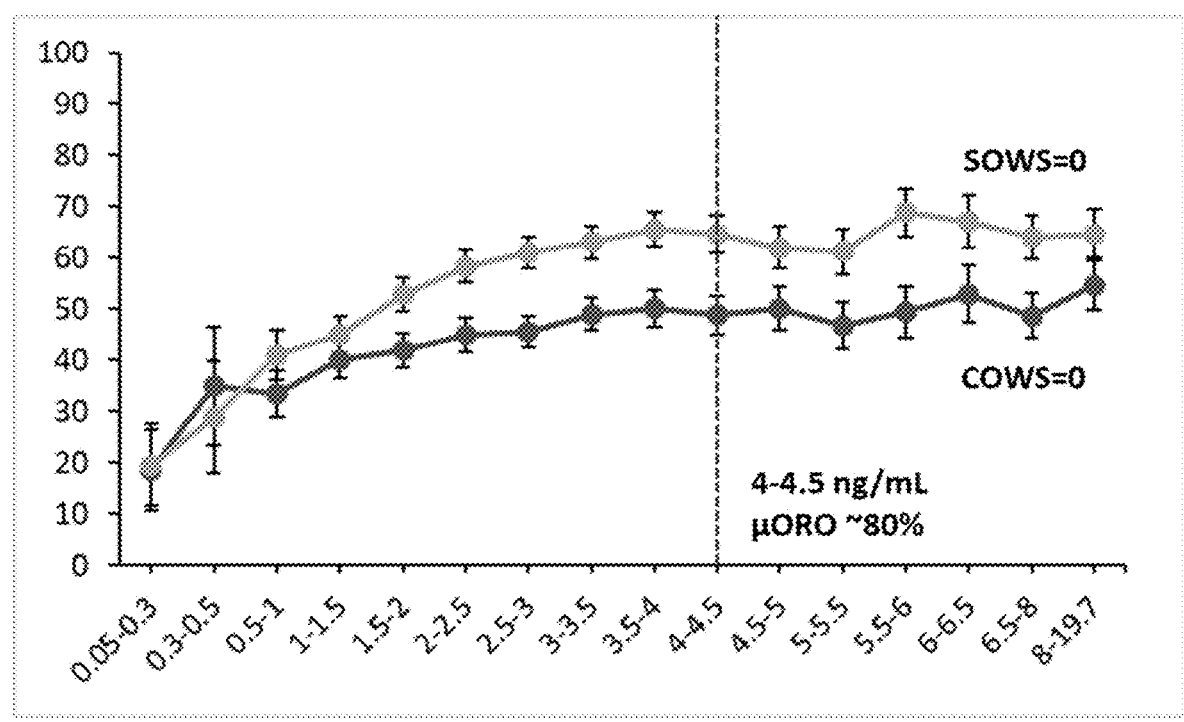
FIG. 4 shows the relationship between buprenorphine plasma concentrations (x-axis) and the percentage of SOWS scores equal to of 0 (y-axis, top line) and COWS scores equal to 0 (y-axis, bottom line). The vertical dotted-line shows that the predicted mu-opioid receptor occupancy is about 78% when the buprenorphine plasma concentration is from about 4 ng/mL to about 4.5 ng/mL. The error bars represent the 95% confidence intervals.

The COWS were used to quantify withdrawal symptoms, and the results of the study are shown in Table 1 and FIG. 3. The COWS scores ranged from 0 to 48 and were categorized as no withdrawal (0-4), mild (5-12), moderate (13-24), moderately severe (25-36) and severe withdrawal (>36). Following SUBOXONE® film run-in and treatment with Formulation D, withdrawal symptoms were controlled in more than 99% of the patients (scores ≤12), with the majority of patients having scores ≤4. In the placebo group, COWS scores were also ≤12 in 97% of the patients; however, this result is not surprising because over 90% of the subjects in the placebo group were using illicit opioids throughout the study, thus controlling their cravings and withdrawal symptoms with the use of illicit opioids. Only 2 patients from the placebo group were not using opioids at the end of the study. No patients showed severe withdrawal (COWS score >36). About 50% of COWS scores were equal to 0 when the buprenorphine plasma concentration was about 3.5 ng/mL to about 4 ng/mL, as shown in FIG. 4. Similar results were observed for SOWS scores, as shown in Table 2.

TABLE 1

| Clinical Opiate Withdrawal Scale (COWS) | Group 1 (300 mg/100 mg) | Group 2 (300 mg/300 mg) |
|---|---|---|
| Difference in LS means (SE) | −0.4 (0.38) | −1.0 (0.38) |
| 95% CI | −1.13, 0.36 | −1.72, −0.23 |
| p-value | 0.3143 | 0.0101 |

TABLE 2

| Subjective Opiate Withdrawal Scale (SOWS) | Group 1 (300 mg/100 mg) | Group 2 (300 mg/300 mg) |
|---|---|---|
| Difference in LS means (SE) | −1.6 (0.87) | −2.6 (0.87) |
| 95% CI | −3.29, 0.14 | −4.32, −0.90 |
| p-value | 0.0726 | 0.0028 |

Figure 5:
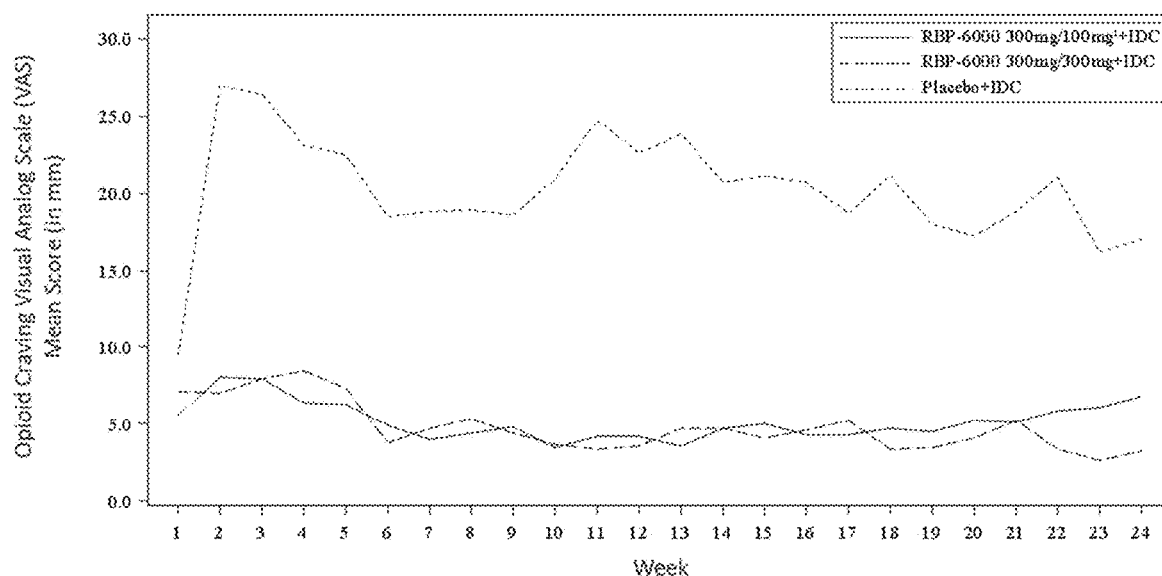
FIG. 5 shows the mean Opioid Craving visual analogue scale (VAS) over time for the clinical study described in the Example. The x-axis shows time in weeks. The y-axis shows opioid craving VAS mean score.
Figure 6:
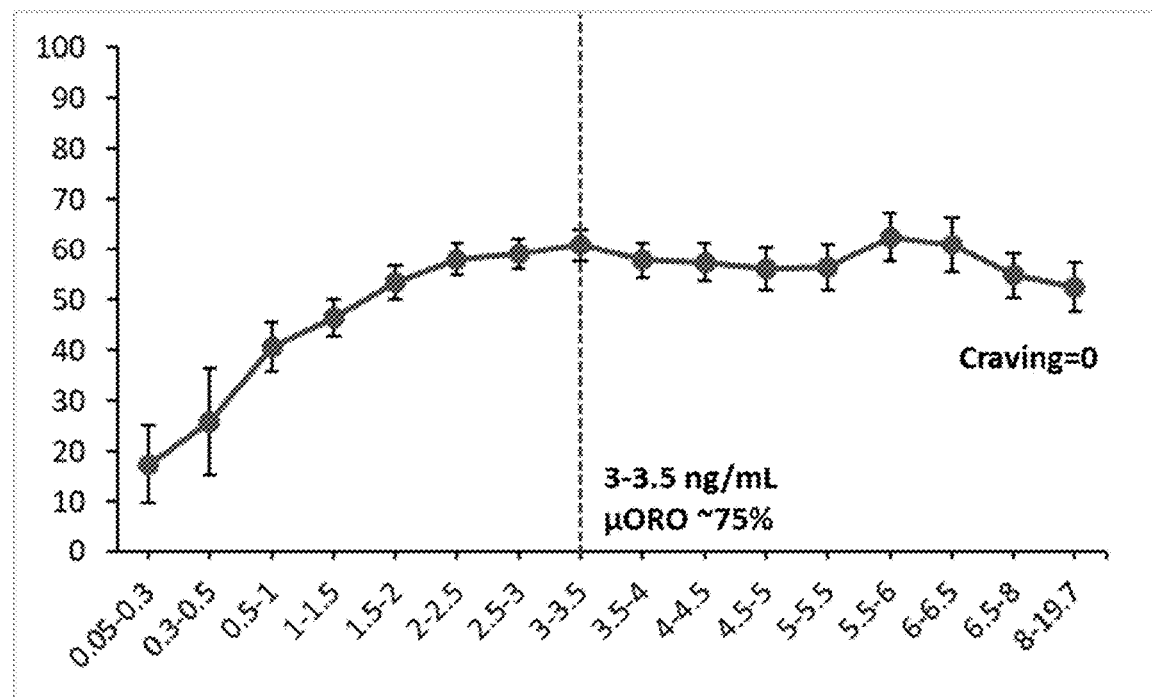
FIG. 6 shows the relationship between buprenorphine plasma concentrations (x-axis) and the percentage of Opioid Craving VAS scores equal to 0 (y-axis). The vertical dotted-line shows that the predicted mu-opioid receptor occupancy is about 75% when the buprenorphine plasma concentration is from about 3 ng/mL to about 3.5 ng/mL. The error bars represent the 95% confidence intervals.

Opioid craving VAS score chart is shown in Table 3. Most patients (81-90%) reported significant craving (>20) at screening. Opioid craving was also assessed during the induction and dose stabilization period with SUBOXONE® film. Following the first subcutaneous injection of Formulation D, the number of patients with zero craving increased rapidly to reach a plateau on Day 2. On average, 54-61% of patients in Group 1 and Group 2 reported zero craving between Day 2 and Day 169 (vs 27% for placebo); 84% of patients in Group 1 and Group 2 reported opioid craving VAS score ≤5 (vs 45% for placebo); and only 6-7% of patients in Group 1 and Group 2 reported craving >20 (vs 34% for placebo). Table 4 shows the mean changes in Opioid Craving VAS scores compared to placebo. Mean Opioid Craving VAS scores over the course of the study are shown in FIG. 5. About 60% of Opioid Craving VAS scores were equal to 0 at buprenorphine plasma concentration levels of about 2.5 ng/mL to 3 ng/mL, as shown in FIG. 6.

TABLE 3

| Opioid Craving Visual Analog Scale Score (VAS) |
|---|
| 0 (no craving) |
| 1-5 |
| 6-20 |
| 21-100 (significant craving) |

TABLE 4

| Opioid Craving Visual Analog Scale Score (VAS) | Group 1 (300 mg/100 mg) | Group 2 (300 mg/300 mg) |
|---|---|---|
| Difference in LS means (SE) | −9.4 (2.62) | −12.4 (2.61) |
| 95% CI | −14.56, −4.30 | −17.51, −7.28 |
| p-value | 0.0003 | 0.0101 |

Blood samples for PK assessment were taken during the run-in phase on Day −1 (within 1 hour prior to dosing and 1-2 hours post-dose) and during the double-blind treatment phase on Days 1, 2, 8, 15, 22, 29, 30, 36, 43, 50, 57, 58, 64, 71, 78, 85, 86, 92, 99, 106, 113, 114, 120, 127, 134, 141, 142, 148, 155, 162 and 169). On Days 1, 29, 57, 85, 113 and 141, blood samples were taken within 1 hour prior to subcutaneous injection of Formulation D and at 4 hours (±15 minutes) after subcutaneous injection of Formulation D.

Blood samples were collected in all subjects, including placebo, to preserve the blind. Plasma concentrations of buprenorphine were determined for subjects in active treatment arms using a previously validated LC-MS/MS assay. The lower limit of quantification was established as 0.0500 ng/mL for buprenorphine.

The predicted mean steady-state buprenorphine pharmacokinetic parameters for Patient Groups 1 and 2 are shown in Table 5A below. The steady-state concentrations are based on a 6 month treatment period. In Table 5A, the % mu-opioid receptor occupancy (μORO) is the predicted whole brain mu-opioid receptor occupancy corresponding to the mean steady-state $C_{avg}$.

TABLE 5A

| Dose Group | N | $C_{min}$ (ng/mL) | $C_{avg}$ (ng/mL) | $C_{max}$ (ng/mL) | % μORO |
|---|---|---|---|---|---|
| Group 1 300 mg/100 mg | 194 | 2.74 | 3.14 | 4.11 | 75 |
| Group 2 300 mg/300 mg | 196 | 5.11 | 6.32 | 8.68 | 83 |

The measured mean steady-state buprenorphine pharmacokinetic parameters for Patient Groups 1 and 2 are shown in Table 5B below. The steady-state concentrations are based on a 6 month treatment period.

TABLE 5B

| Dose Group | $C_{min}$ (ng/mL) | $C_{avg}$ (ng/mL) | $C_{max}$ (ng/mL) |
|---|---|---|---|
| Group 1 300 mg/100 mg | 2.48 | 3.21 | 4.88 |
| Group 2 300 mg/300 mg | 5.01 | 6.54 | 10.12 |

The study compared the opioid abstinence rates of patients in Patient Groups 1-3 and the results are shown in Tables 6 and 7 below. 61% of the patients in Group 1 and 64% of the patients in Group 2 completed the therapy, while only 33.3% of the patients in the placebo group completed the study. 47% of the patients in Group 2 were drug free in the last 4 weeks of the 6-month study.

TABLE 6

| % Abstinent Weeks | Group 1 (300 mg/100 mg) | Group 2 (300 mg/300 mg) | Placebo |
|---|---|---|---|
| Mean (SD) | 42.7% (38.50%) | 41.3% (39.66%) | 5.0% (16.98%) |
| p-value | <0.0001 | <0.0001 | — |

TABLE 7

| | Group 1 (300 mg/100 mg) | Group 2 (300 mg/300 mg) | Placebo |
|---|---|---|---|
| ≥80% Abstinent Weeks | 28.4% | 29.1% | 2.0% |
| p-value | <0.0001 | <0.0001 | — |

Figure 8:
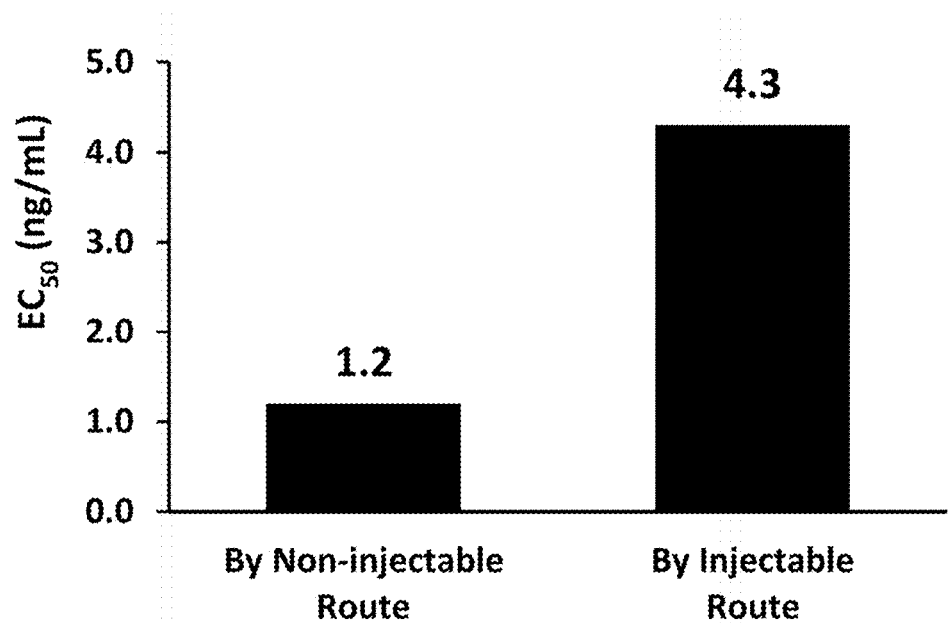
FIG. 8 shows that the $EC_{50}$ for injection drug patients ("by injectable route") was 4.3 ng/mL while the $EC_{50}$ for patients using opioids by non-injectable route at baseline was 3.6 times lower (1.2 ng/mL).
Figure 9:
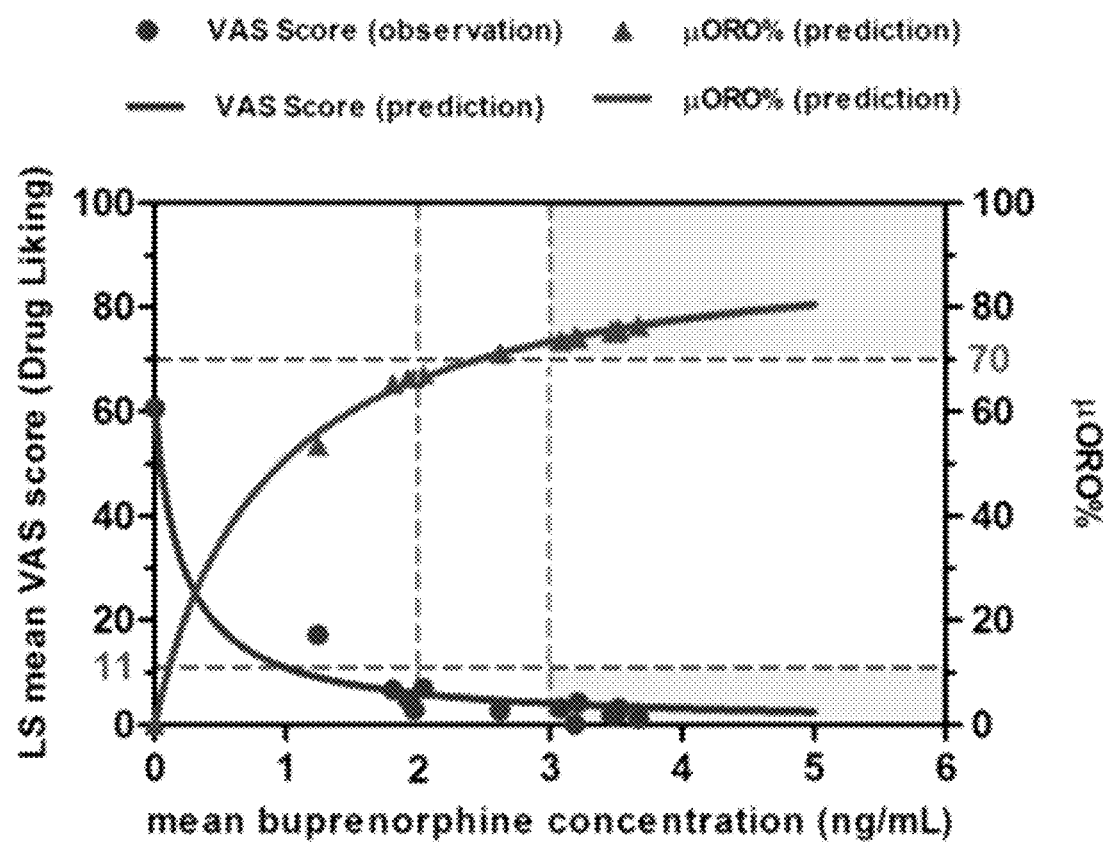
FIG. 9 shows the relationship between mean buprenorphine plasma concentrations (x-axis); mean differences in drug liking VAS scores (hydromorphone 18 mg vs. placebo) (y-axis on left hand side of figure), and predicted whole brain µ-opioid receptor occupancy (y-axis on right hand side of figure). With reference to the 2 ng/mL data point on the x-axis, the upper line refers to the µ-opioid receptor occupancy and the bottom line refers to the mean difference in VAS score.

The study compared the abstinence rate of Group 1 and Group 2 for injection drug patients compared to patients who had used opioids by other routes. Unexpectedly, non-linear mixed effect modeling of exposure/abstinence data indicated that the $EC_{50}$ for injection drug patients was 4.3 ng/mL while the $EC_{50}$ for patients who had abused opioids by non-injectable routes was only 1.2 ng/mL using an $E_{max}$ logistic regression model. These results are shown in FIG. 8. As shown in Table 8 below, it was also discovered that injection drug patients in Group 2 (who were administered the 300 mg dose of Formulation D for 6 months) achieved an opioid abstinence rate of 69% at Day 169 compared to injection drug patients in Group 1 (who were administered the 300 mg dose of Formulation D for 2 months, and then the 100 mg dose of Formulation D for 4 months) who only achieved an opioid abstinence rate of 53% at Day 169. Thus, the data unexpectedly showed that injection drug patients would strongly benefit from the 300 mg dose of Formulation D over a period of 6 months due to the higher $EC_{50}$ value.

TABLE 8

Abstinence Rate (Day 169) For Injection Drug Patients

| | |
|---|---|
| Group 1 (300 mg/100 mg) | 53% |
| Group 2 (300 mg/300 mg) | 69% |

Figure 7:
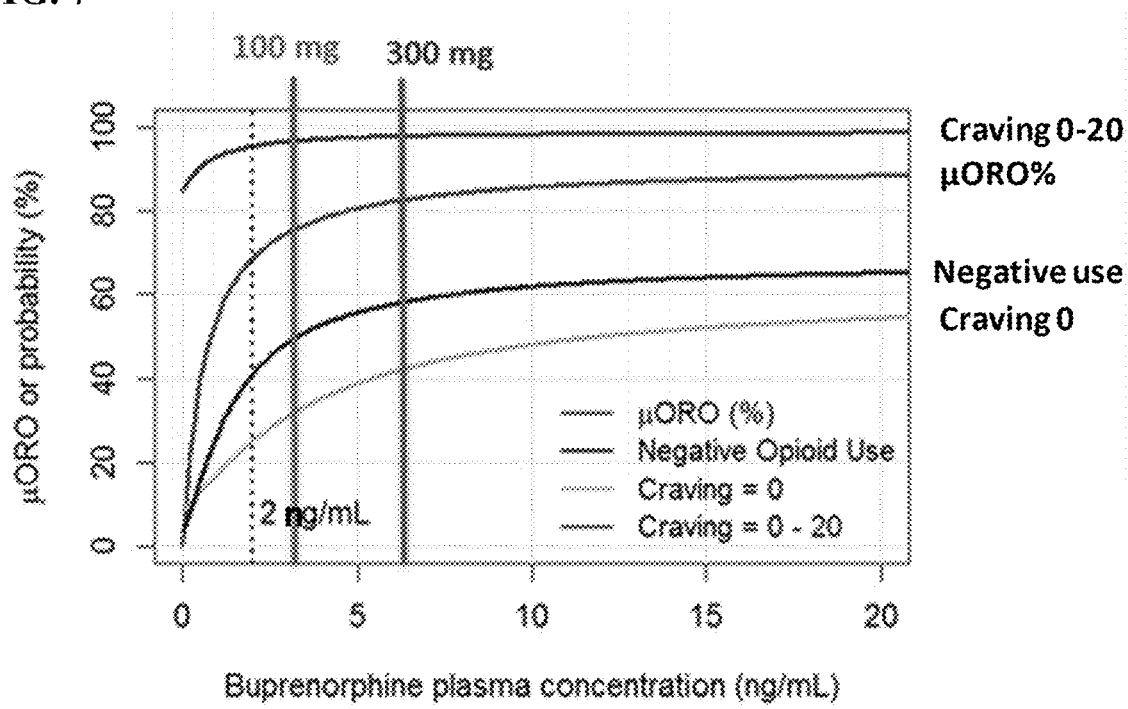
FIG. 7 shows the association between plasma concentrations of buprenorphine, predicted brain μ-opioid receptor occupancy (μORO) and clinical endpoints. With reference to the plasma concentration value of 2 ng/mL, the top line is the probability for a patient to have an Opioid Craving VAS score between 0 and 20 (in view of the buprenorphine plasma concentration shown on the x-axis), the second-from-top line is the percentage of brain µ-opioid receptor occupancy (µORO) (in view of the buprenorphine plasma concentration shown on the x-axis), the third-from-top line is the probability for a patient to have urine sample negative for illicit opioids together with a self-report negative for illicit opioid use (in view of the buprenorphine plasma concentration shown on the x-axis), and the bottom line is the probability for a patient to have an Opioid Craving VAS score of 0 (in view of the buprenorphine plasma concentration shown on the x-axis).

The results of this study confirmed that the dosing regimens for patients in Group 1 and Group 2 were efficacious and statistically superior to placebo. The relationship between clinical endpoints and buprenorphine plasma concentration was characterized by PK/PD modelling. The results of the PK/PD modelling analysis indicate similar shape of exposure-response for brain mu-opioid receptor occupancy and clinical endpoints investigated, consistent with the maximal effect ($E_{max}$) model, as shown in FIG. 7. The correlation between clinical endpoints and mu-opioid receptor occupancy was evaluated using the base population PK/PD models developed for illicit opioid use and craving. The overall probability of negative opioid use increased within the range of 70% to 90% mu-opioid receptor occupancy, indicating that patients would benefit from the 300 mg dose. The probability of zero craving also increased between 70% to 90% mu-opioid receptor occupancy.

The treatment was generally well-tolerated. There were no serious injection site reactions, and there were no discontinuations from the study due to injection site reactions. The treatment-emergent adverse events (TEAE) are shown in Table 9 below.

TABLE 9

| Occurrence (%) | Formulation D 300 mg/100 mg + IDC (n = 203) | Formulation D 300 mg/300 mg + IDC (n = 201) | Placebo + IDC (n = 100) |
|---|---|---|---|
| Any TEAE, n (%) | 155 (76.4) | 134 (66.7) | 56.0 (56.0) |
| Serious TEAE, n(%) | 4 (2.0) | 7 (3.5) | 5.0 (5.0) |
| Severe TEAE, n (%) | 15 (7.4) | 13 (6.5) | 4 (4.0) |
| Discontinuation due to TEAE, n (%) | 7 (3.4) | 10 (5.0) | 2.0 (2.0) |
| Any injection site TEAE | 13.8 | 18.9 | 9.0 |
| Serious injection site TEAE | 0 | 0 | 0 |
| Injection site TEAE leading to discontinuation from study | 0 | 1 (0.5) | 0 |
| TEAEs by preferred term, n (%) | | | |
| Constipation | 19 (9.4) | 16 (8.0) | 0 |
| Nausea | 18 (8.9) | 16 (8.0) | 5 (5.0) |
| Injection site pain | 10 (4.9) | 12 (6.0) | 3 (3.0) |
| Insomnia | 13 (6.4) | 17 (8.5) | 11 (11.0) |
| Headache | 19 (9.4) | 17 (8.5) | 6 (6.0) |
| Nasopharyngitis | 11 (5.4) | 10 (5.0) | 1 (1.0) |
| Injection site erythema | 9 (4.4) | 6 (3.0) | 0 |
| Injection site pruritius | 13 (6.4) | 19 (9.5) | 4 (4.0) |
| Vomiting | 19 (9.4) | 11 (5.5) | 4 (4.0) |
| Upper respiratory tract infection | 15 (7.4) | 12 (6.0) | 1 (1.0) |
| Fatigue | 8 (3.9) | 12 (6.0) | 3 (3.0) |
| Anxiety | 10 (4.9) | 8 (4.0) | 5 (5.0) |
| Drug withdrawal syndrome | 9 (4.4) | 7 (3.5) | 6 (6.0) |
| Blood creatine phosphokinase increase | 11 (5.4) | 5 (2.5) | 1 (1.0) |
| Diarrhea | 5 (2.5) | 5 (2.5) | 5 (5.0) |

The study's primary efficacy endpoint was the mean percentage abstinence (opioid-free weeks), assessed as a cumulative distribution function (CDF) and measured by the percentage of urine samples negative for opioids, combined with self-reports negative for illicit opioid use, from Weeks 5 to Week 24. The key secondary endpoint was treatment success, defined as any patient with ≥80% of urine samples negative for opioids combined with self-reports negative for illicit opioid use from Weeks 5 to 24. Additional secondary measures included the proportion of patients who completed the study, as well as the patients' scores on both opioid craving VAS and the COWS. The safety of Formulation D was also assessed relative to placebo.

The results showed that Formulation D met the primary efficacy endpoint, with both Formulation D dosage regimens demonstrating significantly superior abstinence rates versus placebo (300/300 mg: 41.3%; 300/100 mg: 42.7%; placebo: 5.0%, p<0.0001). Both Formulation D dosing regimens also met the key secondary endpoint of treatment success (300/300 mg: 29.1%; 300/100 mg: 28.4%; placebo: 2.0%, p<0.0001). In addition to the efficacy findings, PK/PD (exposure-response) analyses demonstrated a positive relationship between buprenorphine plasma exposure, mu-opioid receptor occupancy and clinical endpoints of abstinence and opioid craving. Patients taking the 300/300 mg dosage of Formulation D achieved buprenorphine plasma concentrations ≥2 ng/mL, resulting in improvements in abstinence and reductions in opioid craving. The majority of patients taking the 300/100 mg dosage of Formulation D achieved buprenorphine plasma concentrations ≥2 ng/mL, resulting in improvements in abstinence and reductions in opioid craving.

Significantly more patients in both dosing regimen Groups 1 and 2 completed the study compared with those on placebo (300/300 mg: 64.3%; 300/100 mg: 61.3%; placebo: 33.3%, p<0.0001). Formulation D was safe and well-tolerated. Treatment-emergent adverse events (TEAEs) were consistent with the known safety profile of Formulation D, with no unexpected safety findings. The most common TEAE was injection site reactions (300/300 mg: 18.9%; 300/100 mg: 13.8%; placebo: 9.0%), but these were not treatment-limiting. Serious TEAEs were observed in 2.7% of patients on Formulation D (both dosage regimens combined) compared with 5.0% of patients on placebo.

Phase III Clinical Trial Conclusions. Both dosing regimens of Formulation D demonstrated compelling, persistent, and statistically significant differences in percentage abstinence and treatment success when compared to placebo. The treatment benefits were consistent across other important clinical endpoints, including control of craving and withdrawal symptoms. The positive results were confirmed by exposure-response analyses demonstrating a clear relationship between buprenorphine plasma concentration levels, predicted whole brain mu-opioid receptor occupancy, abstinence, and opioid craving. Benefits from Formulation D started with the first dose that achieved a buprenorphine plasma concentration greater than or equal to 2 ng/mL and predicted brain mu-opioid receptor occupancy greater than or equal to 70%. The benefits of Formulation D were maintained for the one month dosing interval and over the entire treatment duration, reducing the risk of requiring rescue medication. Formulation D was safe and generally well-tolerated. The safety profile was consistent with the known safety profile of transmucosal buprenorphine with no unexpected safety findings. Injection site reactions were not treatment-limiting.

Example 2

The results of the Phase III clinical trial described in Example 1 were further analyzed to characterize exposure-response relationships Formulation D with respect to illicit opioid use and opioid craving, and to assess dropout patterns in the pivotal Phase III efficacy study. Abstinence was the primary efficacy variable defined as opioid negative urine samples combined with self-reports negative for illicit opioid use. Opioid craving was a secondary efficacy variable and was assessed on a visual analog scale (VAS) ranging from 0 (no craving) to 100 (strongest craving). Weekly measures of abstinence and craving were obtained following randomization. The integrated PK/PD model for abstinence utilized two categories: (i) opioid use=0 when there was a negative urine drug screen and negative self report; and (ii) opioid use=1. The craving VAS score used four categories: (i) craving=0; (ii) craving=1-5; (iii) craving=6-20; and (iv) craving=21-100. Dropout from the study was modeled using time-to-event analysis.

A sequential PK/PD modeling approach was used where empirical Bayes estimates (EBEs) of PK parameters were used to derive buprenorphine concentrations at the time of efficacy measurements. EBEs were estimated from a population PK model developed using combined PK data from a multiple ascending dose study and the Phase III double-blind efficacy study.

Abstinence was analyzed as a binary variable using an Emax logistic model shown in Equation 2:

$$\text{logit}[P(Y_{ij} = 0)] = \alpha + fd + \eta_i$$

$$fd = \frac{E_{max,i} \times C_{p,ij}}{EC50_i + C_{p,ij}}$$

wherein $P(Y_{ij}=0)$ is the probability of abstinence for subject i at time $t_{ij}$; $\alpha$ is the logit value in the absence of buprenorphine treatment; $\eta_i$ is the subject-specific random effect on $\alpha$; $C_{p,ij}$ is the buprenorphine plasma concentration for subject i at time $t_{ij}$; $E_{max,i}$ is the maximum of drug effect for subject i (fd); and $EC50_i$ is the buprenorphine plasma concentration at which 50% of the maximum drug effect is achieved.

Craving was analyzed as an ordinal variable with 4 categories described above using a proportional odds model as shown in Equation 3:

$$\text{logit}[P(Y_{ij} \leq m)] = \alpha_m + fd + \eta_i$$

wherein m defines the craving severity categories: 1, 2, or 3; $\alpha_m$ is the logit value in the absence of drug treatment for categories 1 ($\alpha_1$), 2 ($\alpha_2$), or 3 ($\alpha_3$) such that $\alpha_1 < \alpha_2 < \alpha_3$; and fd and $\eta_i$ are drug effect and random effect as defined in Equation 2.

Figure 17:
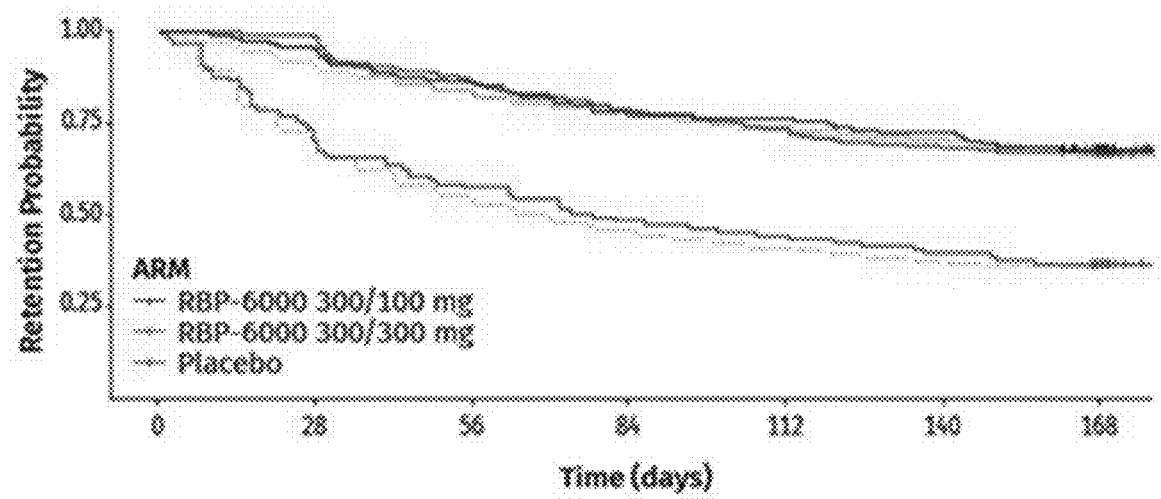
FIG. 17 shows the model predictions versus observations for dropout per treatment arm. Treatment was a significant predictor of dropout, with completion rates two times higher in the treatment arms (300/300 mg at 64%; 300/100 mg at 62%) compared to placebo (34%). The solid lines are the Kaplan Meier curves for observations, while the dashed line are the Kaplan Meier curves for model predictions.
Figures 18A, 18B:
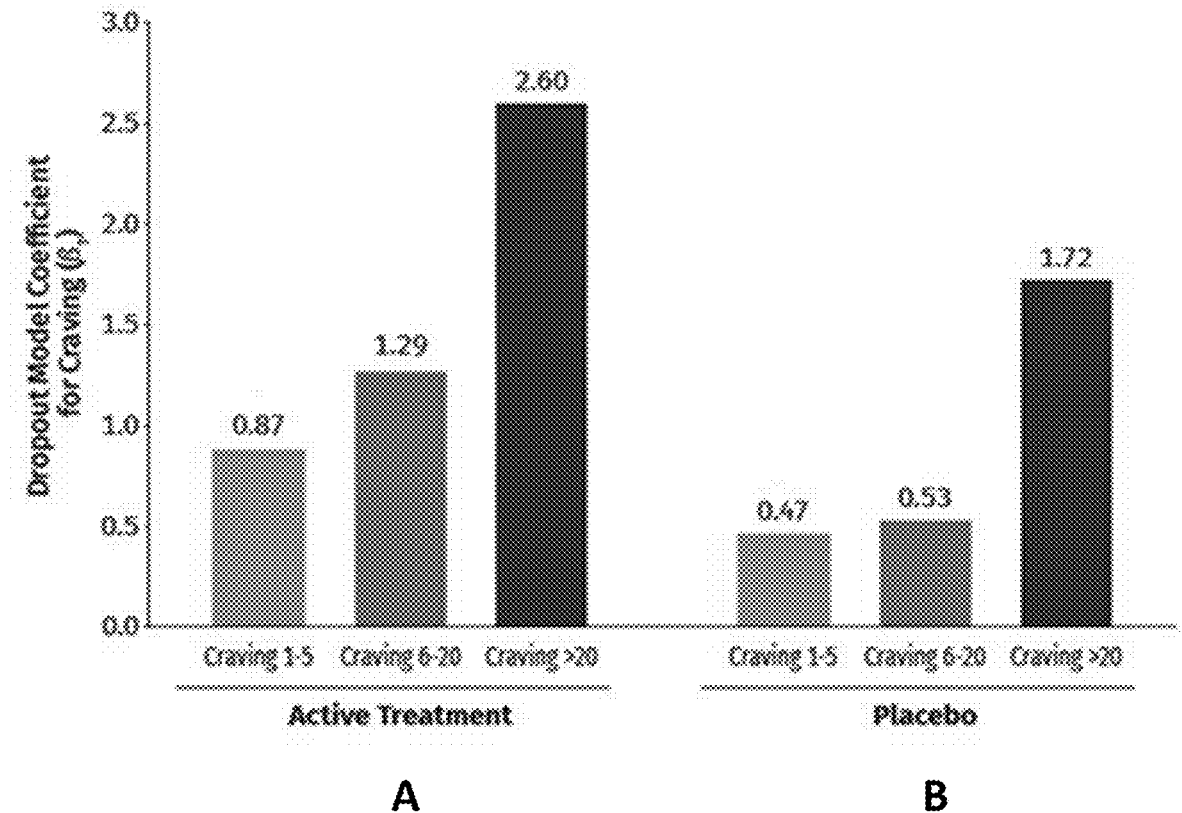
FIGS. 18A-B show the effect of opioid craving on the dropout rate.

Since dropout rates of 32-33% for the treatment arm vs. 64% for the placebo arm were observed (as shown in FIG. 17), dropout was modeled using time-to-event analysis. Several models were tested and the Gompertz model provided the best fit. Accordingly, the probability of staying in the trial up to time $t_i$ was given by Equation 4:

$$\text{Survival}(t_i) = \exp(-\int_0^{t_i} \text{hazard}(t)dt)$$

wherein hazard(t) is $\beta_0 \times \exp(-\text{ke} \times t)$; $\beta_0$ is the baseline instantaneous rate (hazard) of dropout; and ke is the rate constant for the exponential decrease in hazard over time (Gompertz model).

Covariate analyses were conducted for Equations 2, 3, and 4, including demographic characteristics, baseline clinical characteristics (e.g., Beck Depression, Pain, Clinical Global Impression of Disease Severity [CGI-S], injectable vs. non-injectable route for illicit opioid use), social characteristics (e.g., employment, health insurance) as well as genetic status for opioid receptors (OPRM1, OPRD1, OPRK1) and dopamine D2 receptors (DRD2). For time-to-event analysis, observed records of opioid use and craving were evaluated as predictors of dropout.

Data from 489 subjects was including in the PK/PD analyses. The baseline characteristics of subjects included in the PK/PD analyses are shown in Table 10, where numbers in brackets refer to standard deviation.

TABLE 10

| Characteristic | Formulation D (300 mg for 2 months; 100 mg for 4 months) | Formulation D (300 mg for 2 months; 300 mg for 4 months) | Placebo |
|---|---|---|---|
| Age | | | |
| Mean (SD) | 40.42 (11.23) | 39.34 (10.96) | 39.19 (10.96) |
| Sex (N(%)) | | | |
| Male | 128 (66) | 132 (67) | 64 (65) |
| Female | 66 (34) | 64 (33) | 35 (35) |
| Baseline BMI, mean (SD), kg/m² | | | |
| BMI | 25.3 (4.2) | 26.4 (4.4) | 25.3 (4.3) |
| Race (N(%)) | | | |
| White | 132 (68) | 140 (71) | 77 (78) |
| Black or African American | 56 (29) | 54 (28) | 20 (20) |
| Others | 6 (3.1) | 2 (1.0) | 2 (2.0) |
| OPRD1 (rs678849) (N(%)) | | | |
| CC | 66 (34) | 68 (35) | 33 (33) |
| TC | 80 (41) | 78 (40) | 47 (48) |
| TT | 38 (20) | 37 (19) | 15 (15) |
| not available | 10 (5.2) | 13 (6.6) | 4 (4.0) |
| Opioid Use (Screening)(N(%)) | | | |
| non-injectable route | 110 (57) | 116 (59) | 49 (50) |
| Injectable route | 84 (43) | 80 (41) | 50 (50) |

TABLE 10-continued

| Characteristic | Formulation D (300 mg for 2 months; 100 mg for 4 months) | Formulation D (300 mg for 2 months; 300 mg for 4 months) | Placebo |
|---|---|---|---|
| Employment Status (N(%)) | | | |
| Unemployed | 130 (67) | 113 (58) | 55 (56) |
| Employed | 55 (28) | 76 (39) | 34 (34) |
| not available | 9 (4.6) | 7 (3.6) | 10 (10) |
| Mean Baseline Scores | | | |
| Opiate Craving Visual Analog Scale | 4.6 (5.80) | 4.6 (8.75 | 7.6 (15.88 |
| Clinical Opiate Withdrawal Scale | 2.22 (2.56) | 2.1 (2.31) | 2.3 (2.50) |
| Subjective Opiate Withdrawal Scale | 4.4 (6.12) | 3.6 (5.42) | 4.5 (5.64 |

Figures 10A, 10B, 10C:
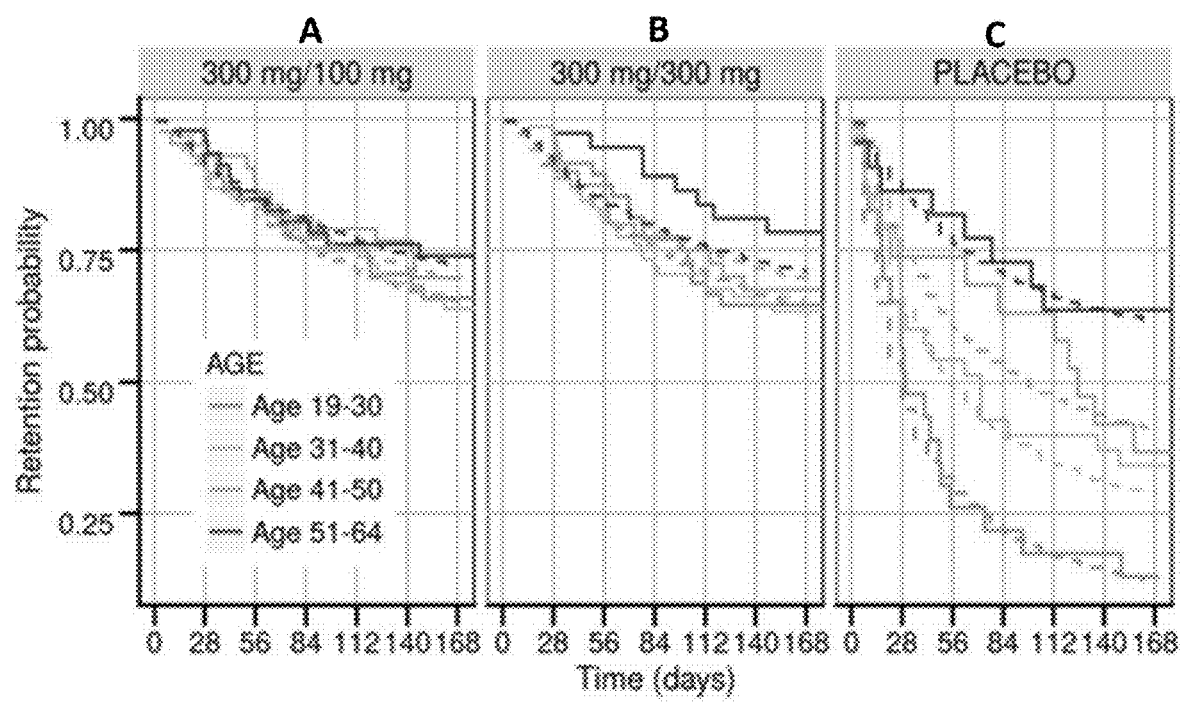
FIGS. 10A-C show the model predictions versus observations for dropout per treatment arm and age category.
Figures 15A, 15B, 15C:
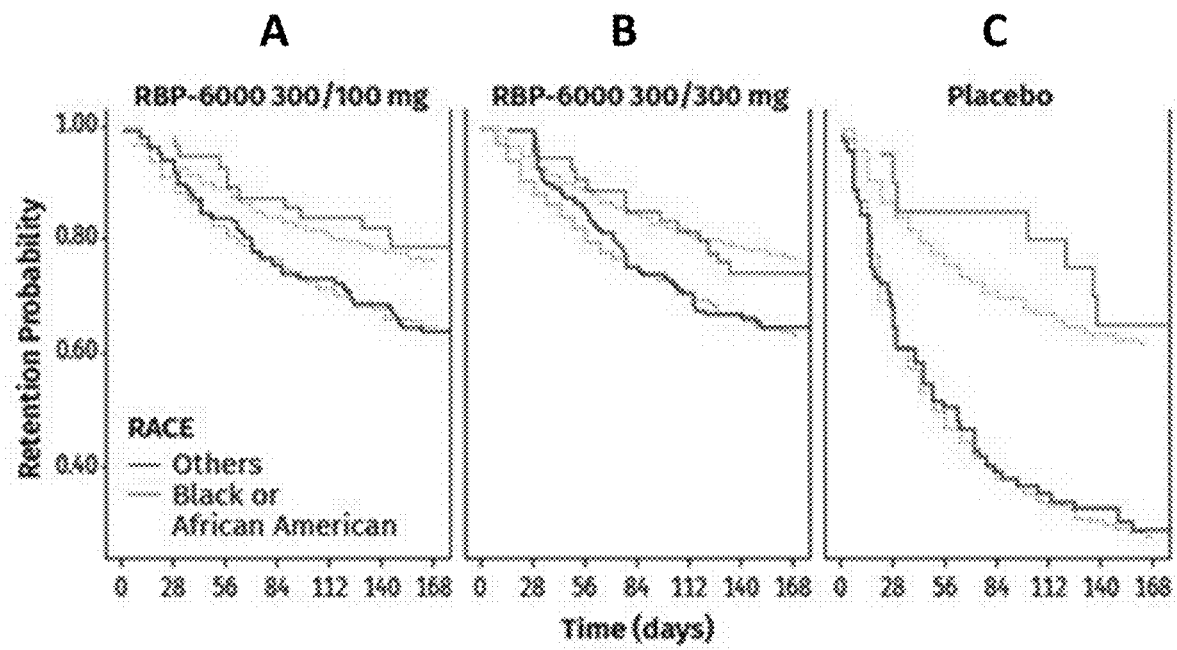
FIGS. 15A-C show the model predictions versus observations for dropout per treatment arm based on race, particularly comparing black/African-American patients to other races.
Figures 16A, 16B, 16C:
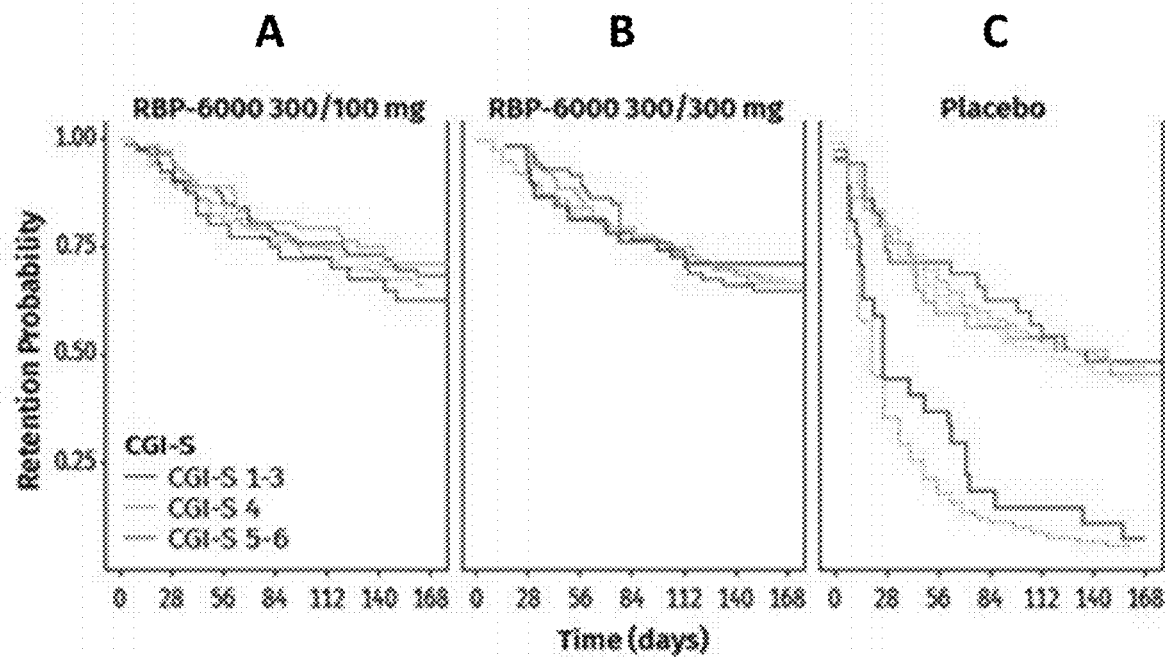
FIGS. 16A-C show the model predictions versus observations for dropout per treatment arm based on CGI-S score.
Figures 19A, 19B:
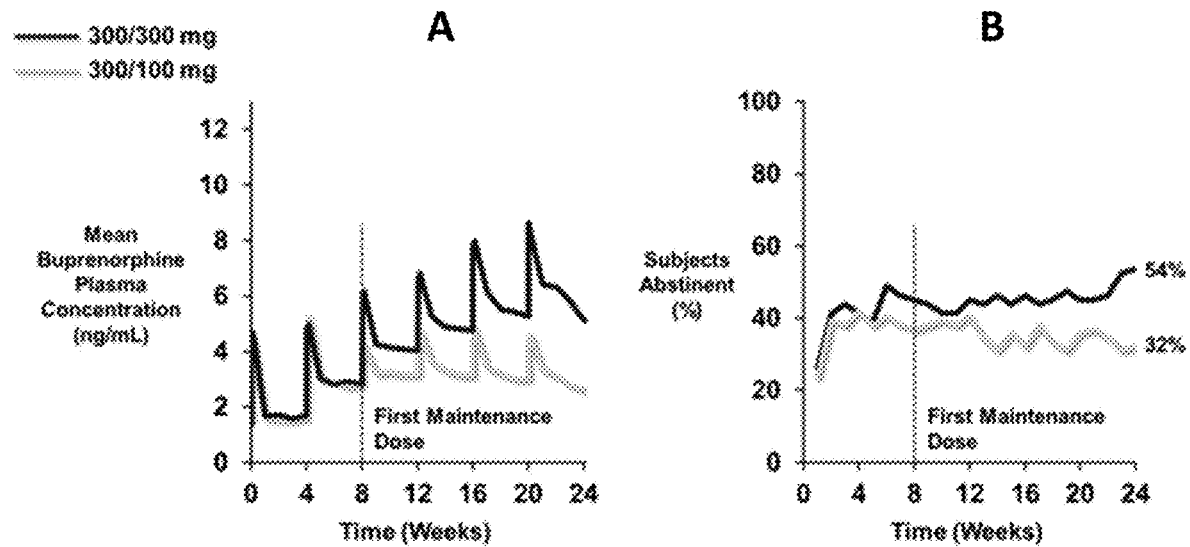
FIGS. 19A-B show the pharmacokinetic results (FIG. 19A) and pharmacodynamic results (FIG. 19B) for the two dosing regimens (300/300 vs. 300/100) administered to injection drug patients.

Dropout. Dropout was successfully predicted from baseline subject characteristics and recorded measures of efficacy (craving), supporting missing at random (MAR) mechanisms. Craving: A score greater than 20 was associated with up to 3.0-fold and 3.6-fold higher dropout rates in active and placebo arms, respectively, compared to craving score of 1-5 (FIGS. 19A-B). Thus, opioid craving was identified as a major predictor of dropout for both placebo and active treatment arms, indicating that craving should be closely monitored for treatment of OUD patients. CGI-S (baseline) (i.e., a score of disease severity): A higher dropout rate was only seen in the placebo group when the CGI-S score was less than or equal to 3, as shown in FIGS. 16A-C. As shown in FIGS. 15A-C, Black or African American subjects had a dropout rate that was about 40% lower in all treatment groups. As shown in FIGS. 10A-C, age had an effect only on subjects from the placebo group, which suggests that once treatment was started, age made no difference with respect to treatment retention.

Figure 11:
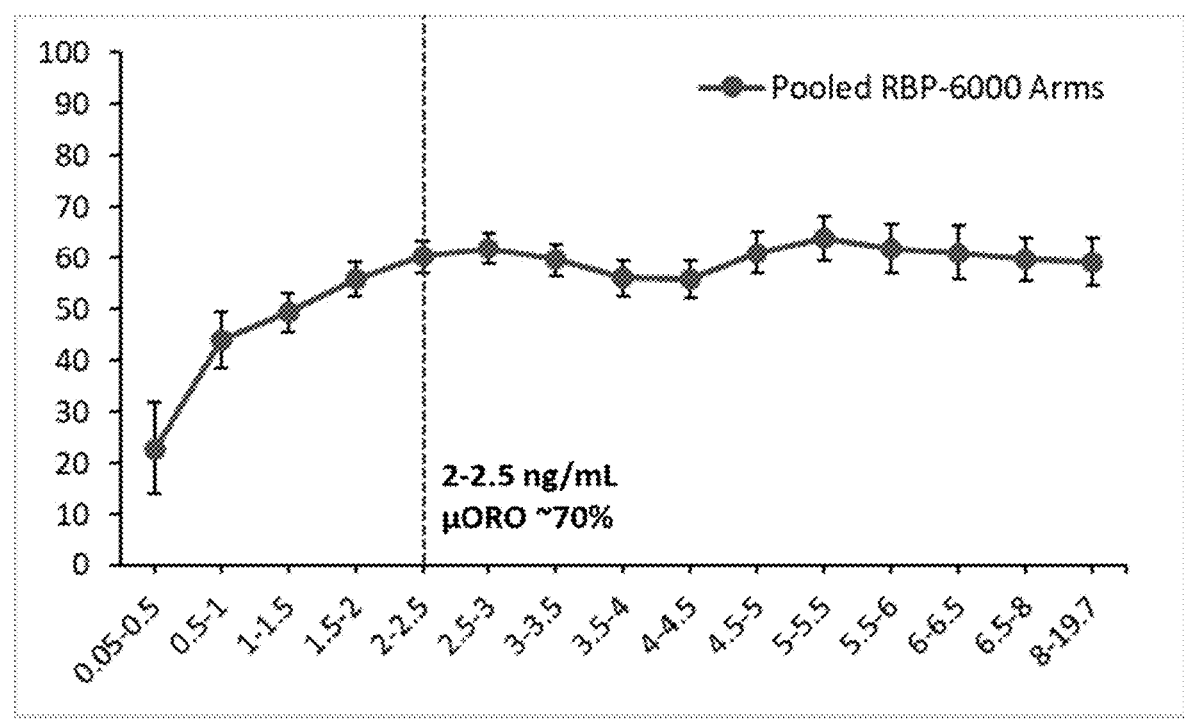
FIG. 11 shows the relationship between buprenorphine plasma concentrations (x-axis) and the probability of negative use (based on urines samples negative for opioids together with self-reports negative for illicit opioid use) (y-axis). The vertical dotted-line shows that the predicted mu-opioid receptor occupancy is about 70% when the buprenorphine plasma concentration is from about 2 ng/mL to about 2.5 ng/mL. The error bars represent the 95% confidence intervals.

Abstinence. At screening, all but one subject used opioids. During treatment with Formulation D, the percent abstinence increased from 37-40% on Day 1 (end of SUBOXONE® run-in) to 64-66% at the end of the trial. As expected, the percent abstinence in the placebo group rapidly declined after Day 2, reaching 6% at the end of the trial. Observations clearly supported an exposure-response relationship consistent with an $E_{max}$ model, as shown in FIG. 11. The plateau was reached at about 2 ng/mL. The logistic regression model successfully described the time course of the number and percent of subjects abstinent and non-abstinent in all treatment arms (data not shown).

Figure 12:
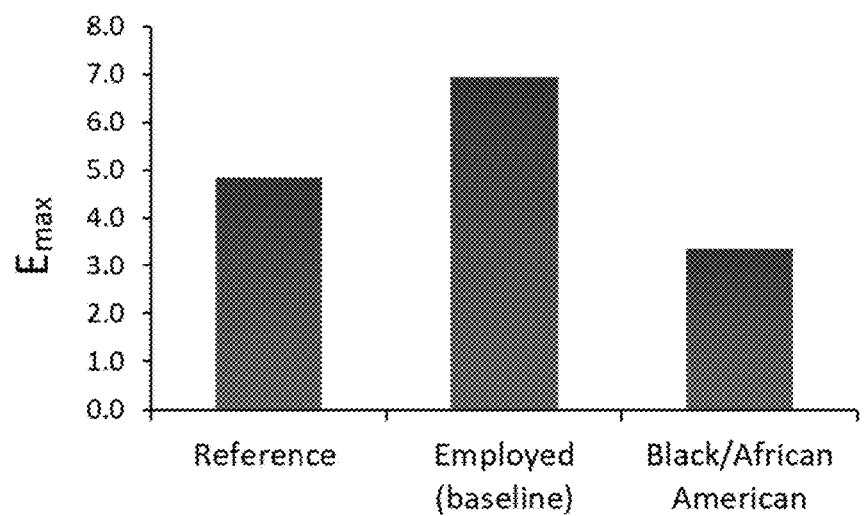
FIG. 12 provides a summary of the covariate effects on abstinence on the reference standard, employed subjects, and black or African American subjects.
Figure 13:
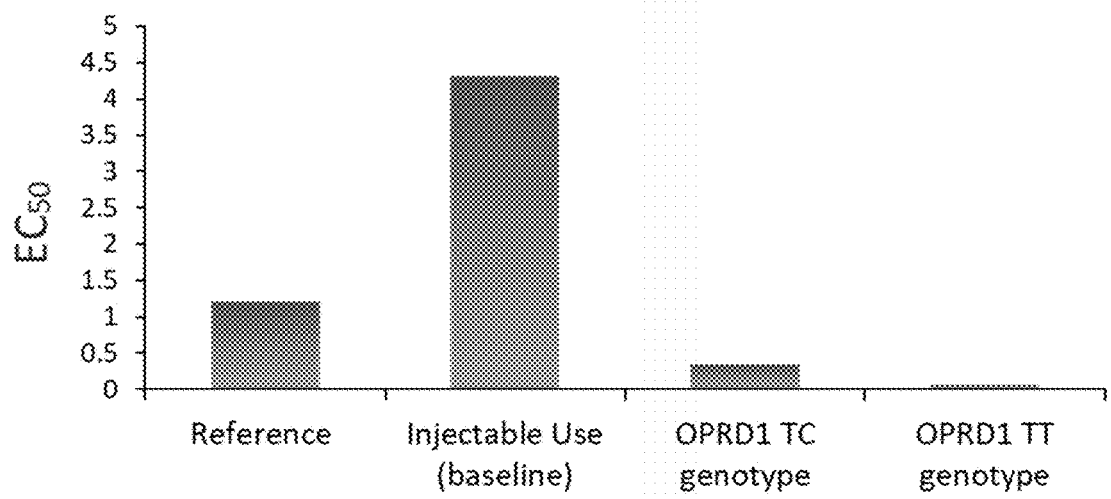
FIG. 13 provides a summary of the covariate effects on abstinence on the reference standard, injection drug patients ("Injectable Use"), subjects with the opioid delta receptor (OPRD1) TC genotype with respect to single nucleotide polymorphism (SNP) rs678849, and subjects with the OPRD1 TT genotype with respect to single nucleotide polymorphism (SNP) rs678849.

As shown in FIGS. 12 and 13, significant covariates were identified on $E_{max}$ and $EC_{50}$. Subjects who injected opioids at baseline had a 3.6-fold higher $EC_{50}$ than subjects using opioids by non-injectable route at baseline, indicating that those subjects would benefit from the higher 300 mg maintenance dose (as opposed to the 100 mg maintenance dose).

Figures 14A, 14B, 14C:
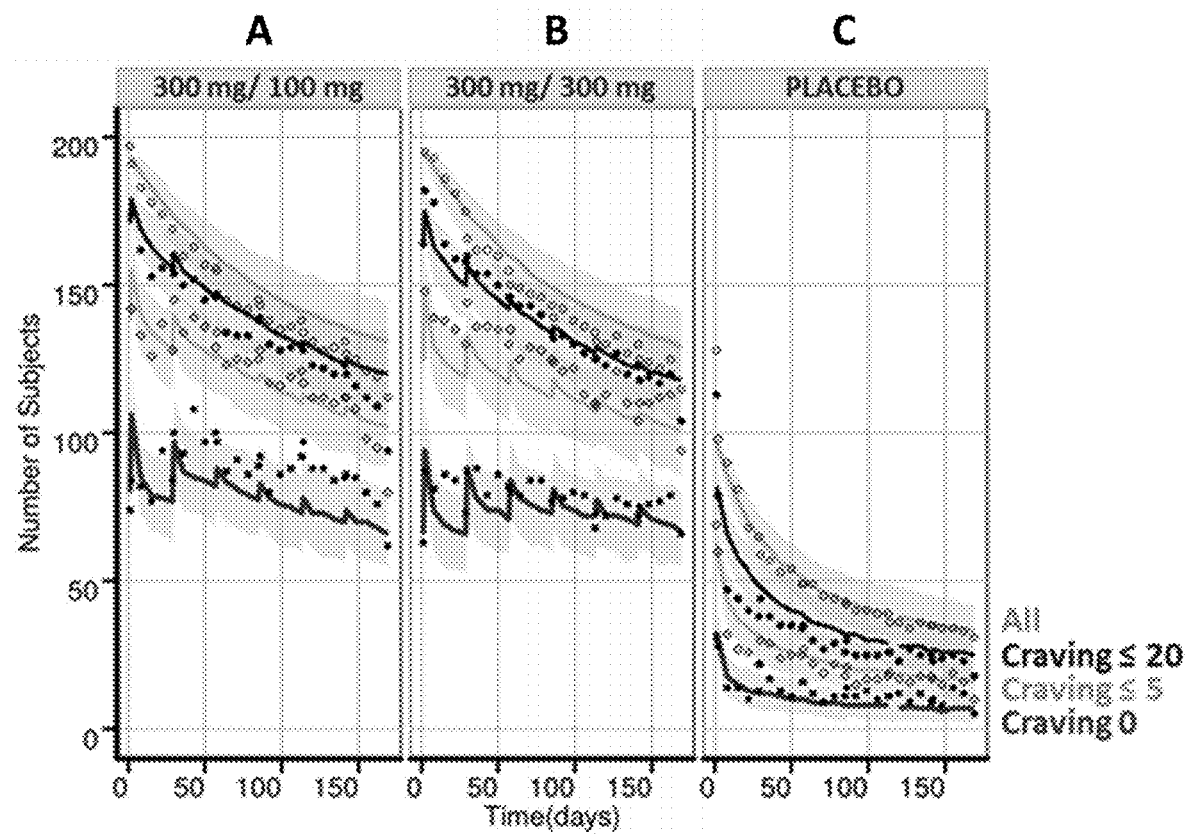
FIGS. 14A-C provide a visual predictive check for the number of subjects of each Opioid Craving VAS score category. In each figure, the upper row represents all patients, the next lower row represents patients having craving VAS score less than or equal to 20, the next lower line represents patients having a craving VAS score less than or equal to 5, and the bottom line represents patients having a craving VAS score of 0.

Craving VAS Score. Similar to abstinence, observed measures of craving supported an exposure-response relationship consistent with an $E_{max}$ model, where the plateau for maximal response was reached at about 3 ng/mL. The proportional odds model described the observed data over the course of the study, as shown in FIGS. 14A, 14B, and 14C. Body mass index was a significant covariate on $E_{max}$, but only explained 1% of the variability.

As shown in FIG. 7, the results indicated similar shape of exposure-response for mu-opioid receptor occupancy, abstinence, and craving VAS score, consistent with an $E_{max}$ model.

Example 3

The results of the Phase III clinical trial described in Example 1 were further analyzed to compare injection drug patients to non-injection drug patients (i.e., patients who used illicit opioids by a non-injectable route). The subgroup analysis found that injection drug patients achieved additional benefit from the higher dose regimen of RBP-6000 (300 mg buprenorphine once monthly for six months). Among injection drug patients, the mean (median) percentage abstinence was higher in the group administered 300 mg once monthly for six months (45% [40%]) than in the group administered 300 mg once monthly for two months followed by 100 mg once monthly for four months (36% [20%]). Among non-injection drug patients, the mean (median) percentage abstinence was higher in the group administered 300 mg once monthly for two months followed by 100 mg once monthly for four months (48% [48%]) than in the group administered 300 mg buprenorphine once monthly for six months (39% [25%]). These data were supported by an exposure-response analysis indicating maximal response for abstinence at higher buprenorphine concentrations (about 6 ng/mL) for injection drug patients, compared with non-injection drug patients. Buprenorphine plasma level of 6 ng/mL corresponds to the average plasma concentration delivered by the 300-mg maintenance dose at steady-state.

A consistent relationship was observed for the PK and PD results between the 2 dosing regimens (300/300 vs. 300/100) for injection drug patients as shown in FIGS. 19A-B. Mean levels start to diverge after the first maintenance dose (Week 8) and the difference in concentrations is greatest after the sixth injection. The right-hand panel of FIGS. 19A-B shows the percentage of injection drug patients who were abstinent over the course of the study, using the same pre-specified imputation method as the primary efficacy endpoint. The abstinence rates started to diverge after the administration of the first maintenance dose (Week 8), consistent with the divergence in the plasma concentrations. By the end of the study, the abstinence rate among injection drug patients was 54% with the 300/300 dosing regimen compared to 32% with the 300/100 dosing regimen. Based on the relative risk, subjects who received the higher maintenance dose were 1.7 times, or 70% more likely to be abstinent at 6 months than subjects who received the lower maintenance dose. This demonstrates that the 300/300 dosing regimen gives injection drug patients the best chance of success.

Example 4

Following the Phase 3 clinical study (NCT02357901) described in the preceding examples, a Second Study (NCT02510014) was conducted that enrolled: (i) 412 new or de novo patients and (ii) 257 roll-over patients who completed the Phase 3 clinical study without significant protocol deviations and who wished to roll-over into the second study. The Second Study protocol involved 12 total monthly injections of RBP-6000 where the new patients received 12 monthly doses, and where the roll-over patients received 6 monthly doses in the first Phase 3 clinical study and 6 monthly doses in the second study. "Monthly dose" refers to one dose per month, such that 6 monthly doses means the patient received one dose, once per month, for 6 months; and 12 monthly doses means the patient received one dose, once per month, for 12 months. The patient demographics for the Second Study are shown in Table 11.

TABLE 11

| Characteristic | Roll-Over Patients (n = 257) | New Patients (n = 412) |
|---|---|---|
| Age | | |
| Mean (SD) | 41.6 (11.1) | 38.4 (12.1) |
| Sex (N(%)) | | |
| Female | 88 (34.2) | 149 (36.2) |
| Male | 169 (65.8) | 263 (63.8) |
| Race (N(%)) | | |
| White | 167 (65.0) | 295 (71.6) |
| Black or African American | 85 (33.1) | 107 (26.0) |
| Baseline BMI, mean (SD), kg/m² | 26.1 (5.1) | 25.4 (4.3) |
| Opioid Use (Screening)(N(%)) | | |
| non-injectable route | 143 (55.6) | 217 (52.7) |
| Injectable route | 114 (44.4) | 195 (47.3) |
| Mean Baseline Scores | | |
| Opiate Craving Visual Analog Scale | 4.4 (9.6) | 5.9 (10.6) |
| Clinical Opiate Withdrawal Scale | 1.5 (2.0) | 2.1 (2.4) |
| Subjective Opiate Withdrawal Scale | 2.8 (5.4) | 3.8 (5.3) |

Between monthly dose three and twelve, 201 subjects in Study 2 had a dose reduction from the 300 mg dose of RBP-6000 to the 100 mg dose of RBP-6000, where the dose for 25 of these subjects was subsequently increased back from 100 mg to 300 mg before the conclusion of the Second Study. 49 subjects had a dose reduction from 300 mg to 100 mg due to an adverse event; and 8 of these subjects subsequently increased the dose back from 100 mg to 300 mg; and 39 of these subjects ultimately completed the Second Study. The most common adverse events leading to dose reduction were sedation (n=16), liver chemistry elevation (n=13), and constipation (n=5); and all cases were resolved.

The primary endpoint of the Phase 3 clinical study was the cumulative distribution function for percentage abstinence, defined as the percentage of urine samples negative for opioids, combined with self-reports negative for illicit opioid use (Weeks 5-24). Missing urine samples and/or self-reports were imputed as non-negative. The Phase 3 clinical study also evaluated the relationship between buprenorphine plasma concentration and efficacy outcomes, based on observations.

The Phase 3 clinical study and Second Study analyzed the following: (i) the percentage of subjects who were abstinent for each study visit to determine the persistence of efficacy of RBP-6000; (ii) the characterization of the buprenorphine plasma concentration-time profile over twelve months of treatment for population pharmacokinetic (PK) modeling; and (iii) long-term safety by identifying treatment-emergent adverse events (TEAEs), clinical laboratory tests, vital signs, electrocardiograms, and local injection site grading, e.g., pain, tenderness, erythema-redness, induration, and swelling.

In the Phase 3 clinical trial, both RBP-6000 treatment groups (300 mg/300 mg and 300 mg/100 mg) were significantly superior to placebo (p<0.0001) for the primary endpoint, with mean percentage abstinence from weeks 5-24 of 43% (300 mg/100 mg), 41% (300 mg/300 mg), and 5% (placebo). All missing urine samples and self-reports for opioids were considered non-negative.

Figure 20:
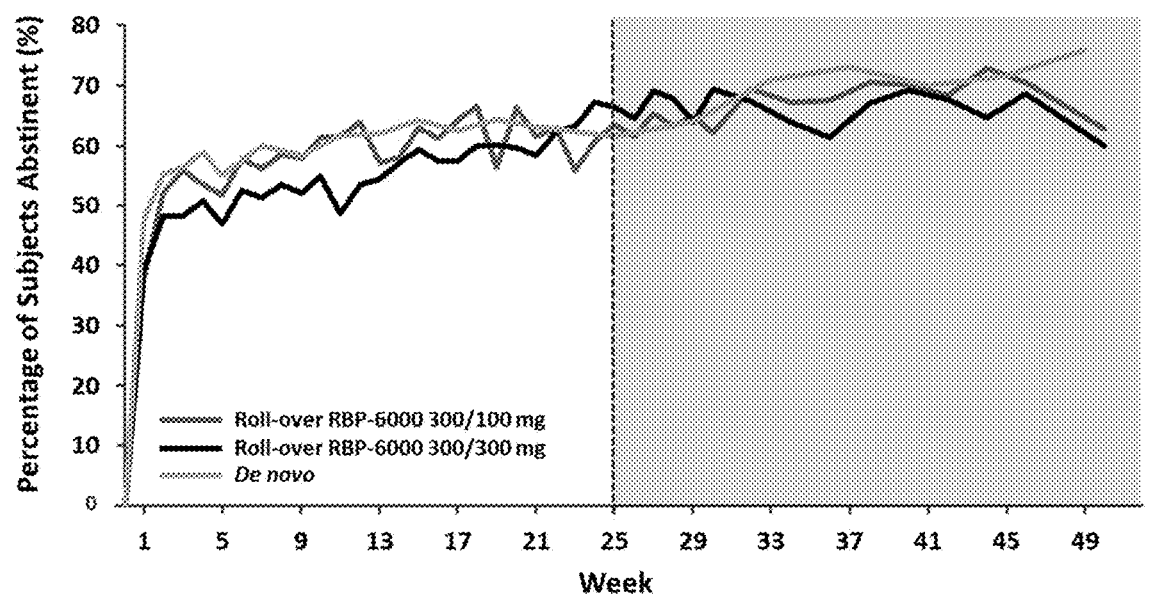
FIG. 20 shows the percent of abstinent subjects (y-axis) over the course of the weeks (x-axis) of the Phase 3 clinical trial and the Second Study, as discussed in Example 4.

Based on available assessments at week forty-nine, 61% (107/174) of roll-over subjects (excluding placebo roll-over) and 76% (157/207) of new subjects were abstinent. FIG. 20 shows the percentage of subjects abstinent over time for: (i) new subjects, (ii) roll-over subjects on the 300 mg/100 mg dosing regimen, and (iii) roll-over subjects on the 300 mg/300 mg dosing regimen.

Figure 21:
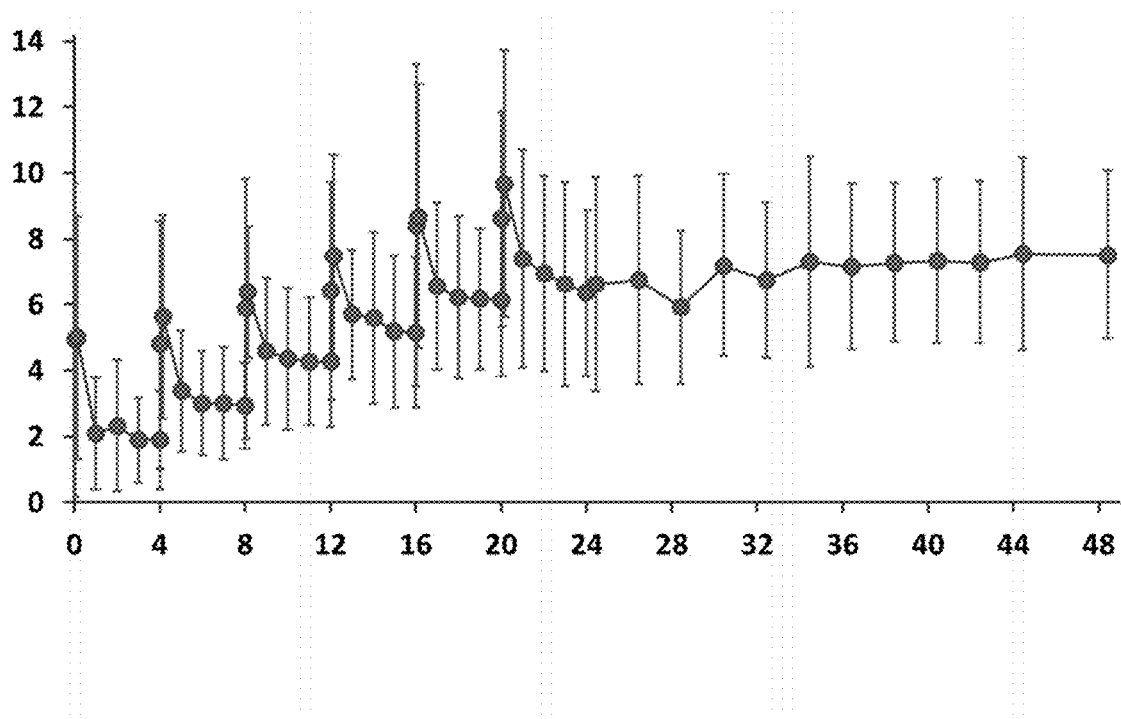
FIG. 21 is a graph showing the mean buprenorphine plasma concentrations (y-axis) over the course of weeks (x-axis) among roll-over subjects receiving twelve consecutive 300 mg doses of RBP-6000. The error bars represent the +/− standard deviation.

The population PK model indicated that target buprenorphine plasma concentrations associated with opioid blockade were achieved after the first 300 mg dose of RBP-6000, and that steady-state was reached after 6 doses, as supported by observed data in subjects receiving 12 consecutive monthly doses of 300 mg of RBP-6000. The results are show in FIG. 21.

FIG. 11 shows that the probability of abstinence (calculated from observed data) increased with buprenorphine plasma concentration up to a plateau of about 2 to 2.5 ng/mL or about 70% mu-opioid receptor occupancy. FIG. 6 shows a maximal response for a score of 0 on opioid craving VAS at a buprenorphine plasma concentration of about 3 to 3.5 ng/mL or about 75% mu-opioid receptor occupancy. FIG. 4 shows a maximal response for a score of 0 on COWS and SOWS at a buprenorphine plasma concentration of about 4 to 4.5 ng/mL or about 78% mu-opioid receptor occupancy.

As shown in Table 12, the incidence of TEAEs was higher in new subjects than in roll-over subjects in the Second Study. All non-serious injection site reaction TEAEs were reported in 13.2% of the subjects in the Second Study. Less than 1% of subjects had injection site reaction TEAEs that led to discontinuation. No clinically meaningful changes in vital signs, ECGs, and laboratory parameters were apparent during the Second Study.

TABLE 12

| Occurrence (%) | Roll-Over (n = 257) | New (n = 412) |
|---|---|---|
| Any TEAE, n(%) | 145 (56.4) | 302 (73.3) |
| Serious TEAE, n (%) | 9 (3.5) | 16 (3.9) |
| Severe TEAE, n (%) | 7 (2.7) | 36 (8.7) |
| TEAE leading to discontinuation from study | 4 (1.6) | 13 (3.2) |
| TEAEs by preferred term reported in at least 25% of patients, n(%) | | |
| Constipation | 9 (3.5) | 47 (11.4) |
| Nausea | 10 (3.9) | 37 (9.0) |
| Injection site pain | 7 (2.7) | 39 (9.5) |
| Insomnia | 10 (3.9) | 27 (6.6) |
| Headache | 5 (1.9) | 31 (7.5) |
| Nasopharyngitis | 6 (2.3) | 24 (5.8) |
| Injection site erythema | 5 (1.9) | 22 (5.3) |

In the Phase 3 clinical trial, both dosing regimens (300/300 and 300/100) showed statistically significant differences in the percentage of abstinent subjects versus the percentage of placebo subjects. The Second Study demonstrated that: (i) there was persistent efficacy of RBP-6000 for up to 12 months of treatment; (ii) therapeutic plasma concentrations of buprenorphine associated with abstinence, control of craving and withdrawal symptoms was reached after the first dose and maintained throughout 12 months of treatment; and (iii) the safety profile of new subjects in the Second Study was similar to that observed in the Phase 3 clinical trial. Roll-over subjects had quantitatively fewer TEAEs in the Second Study than the Phase 3 clinical trial, indicating that some TEAEs may tolerate out.

Example 5

A Third Study (NCT02896296) was a 25-week, open-label extension trial enrolling completers (55 rollover, 153 de novo) from the Second Study (NCT02510014) described in Example 4. In the Third Study, participants received Formulation D100 or Formulation D300 at the investigator's discretion. Abstinence was based on negative urine drug screens for opioids. Treatment retention rate/probability was estimated using the Kaplan-Meier method over the 18-month study period.

A total of 153 de novo participants and 44 rollover participants entered the Third Study. Among de novo participants, point prevalence abstinence rates increased from 53% (80/152) at Week 1 (following run-in with SUBOXONE® film) to 75% (115/153) at 6 months, to 89% (134/151) at 12 months, to 93% (115/124) at 18 months. Among rollover participants, point prevalence abstinence rates increased from 36% (16/44) at Week 1 (following run-in with SUBOXONE® film); to 67% (28/42) at 6 months and 66% (29/44) at 12 months; to 82% (27/33) at 18 months.

Overall retention rates at 6, 12, and 18-months were 66%, 50%, 41% among de novo participants and 65%, 45%, 33% among rollover participants. The probabilities of staying on treatment for another 6 months, conditional on having completed 6 or 12 months of treatment, were 76% and 81%, respectively, for de novo participants and 69% and 75%, respectively, for rollovers. More rollover participants were censored from the conditional survival analysis than de novo participants because the gap in initiation of Study 3 affected more rollover participants.

Long-term efficacy of Formulation D was demonstrated by a consistent increase in abstinence rates among study participants treated for up to 18 months. Retention in treatment for 12 or 18 months was high (≥76%) for those who completed 6 or 12 months of treatment. The longer the patients could stay on treatment, the less likely they would discontinue treatment over the time, and more likely they would achieve better treatment outcome.

Example 6

A concentration QT analysis was performed for the clinical studies conducted with Formulation D. Matching buprenorphine and norbuprenorphine plasma concentrations and 12-lead electrocardiograms (ECGs) were pooled across clinical studies conducted with Formulation D in opioid-dependent subjects. Concentration-QT models were developed to describe the effects of buprenorphine and norbuprenorphine on corrected QT (QTc) interval, after accounting for the effect of relevant concomitant medications and illicit drug use on heart rate and/or QT in opioid-dependent subjects. Data from the following studies were included in the analysis:

RB-US-10-0011: Matched concentrations and single 12-lead ECG measurements (110 samples) from 12 subjects who received a single subcutaneous injection of Formulation D containing 20 mg buprenorphine.

RB-US-11-0020: Matched concentrations and single 12-lead ECG measurements (767 samples) from 48 subjects who received a single subcutaneous injection of 50 mg, 100 mg or 200 mg Formulation D (cohorts 1-3), or a single injection of Formulation D100 following 7 consecutive days on SUBOXONE® tablets to achieve a stable dose of 12 mg once daily (QD) (cohort 4).

RB-US-12-0005: Matched concentrations and single 12-lead ECG measurements (1241 samples) from 122 subjects where 87 subjects received repeated subcutaneous injections of Formulation D following induction and stabilization on various doses of SUBUTEX® tablets, and 35 subjects received SUBUTEX® tablets alone. Stable doses of SUBUTEX® tablets ranged between 8 and 24 mg depending on the dose cohort. Formulation D was given repeated (≥4) SC injections of 50 mg, 100 mg, 200 mg or 300 mg of buprenorphine separated by 28 days (Q28D).

RB-US-13-0006: Matched concentrations and single 12-lead ECG measurements (543 samples) from 66 subjects, where 46 subjects received a single subcutaneous injection of 300 mg of different formulation of Formulation D, where the weight average molecular weight of the polymer therein was either low, intermediate, or high following induction and dose stabilization with SUBOXONE® film to achieve a stable dose of 12 mg QD. Twenty subjects received SUBOXONE® film alone.

RB-US-13-0001: Matched concentrations and single or triplicate 12-lead ECG measurements collected with and without Holter monitoring (9264 samples) from 866 subjects were included in the analysis, where 437 subjects have matched screening records but were not randomized and 429 subjects were randomized to receive the following treatments: (A) 300 mg/100 mg: 2 subcutaneous injections of Formulation D300 once every 28 days (±2 days) followed by 4 subcutaneous injections of Formulation D100 once every 28 days (±2 days)(165 subjects); (B) 300 mg/300 mg: 6 subcutaneous injections of Formulation D300 once every 28 days (±2 days)(174 subjects); or (C) Placebo: volume-matched to 300 mg/100 mg group or 300 mg/300 mg group (90 subjects). Subjects were inducted using SUBOXONE® film for 3 days, followed by 4- to 11-day SUBOXONE® film dose adjustment at doses ranging from 8 to 24 mg QD. SUBOXONE® film was tapered in subjects after amendment of study protocol (Day 1: 6 mg, Days 2 and 3: 4 mg, Days 4 and 5: 2 mg).

The objectives of the study were to evaluate whether there was a concentration-related effect of buprenorphine and norbuprenorphine on QT interval after accounting for the effect of relevant concomitant medications and illicit drug use on heart rate and/or QT in opioid-dependent subjects; and to predict the concentration-related effects of buprenorphine on QTc interval at therapeutic and supra-therapeutic concentration levels.

A concentration-QT model was developed to characterize the QTc in the absence of buprenorphine (QTCAbs) and the parameter describing the QT-RR relationship (alpha, fixed at 0.333), to estimate concomitant medication effects on alpha or QTcAbs, and to estimate buprenorphine or norbuprenorphine-related slope (describing drug-related effects on QTc) using nonlinear mixed effects modeling (NONMEM).

The following covariates were evaluated on alpha given their potential to affect heart rate: withdrawal symptoms (as measured by Clinical Opiate Withdrawal Scale (COWS)), clonidine and methocarbamol (used to treat withdrawal symptoms), cocaine, phencyclidine, cannabinoids, barbiturates, and methamphetamines (illicit drugs), amphetamines (taken for therapeutic, e.g., attention-deficit/hyperactivity disorder or illicit use), as well as albuterol (known to increase heart rate).

The following covariates were evaluated on QTcAbs: sex, age, opioids known to have an effect on QTc (methadone, oxycodone), opioids that may have an effect on QTc (hydrocodone, morphine, hydromorphone, oxymorphone, heroin, codeine), or opioids (as a general class, with exact type not recorded in CRF), benzodiazepines, barbiturates, triplicate vs single ECG readings, central vs non-centrally read ECGs, and Holter vs non-Holter. Covariates were selected using individual steps of backward elimination. The concentration-related slope was added and the model was refined. Bootstrap and visual predictive checks were conducted to evaluate model performance.

The two-sided 90% confidence interval of the concentration-related change in QTc (Delta QTc) was determined from the distribution of the bootstrapped values at the: (i) geometric mean $C_{max}$ for Formulation D100 at steady-state using 100 mg data from Studies RB-US-12-0005 and RB-US-13-0001; (ii) geometric mean $C_{max}$ for Formulation D300 at steady-state using 300 mg data from Studies RB-US-12-0005 and RB-US-13-0001; and (iii) supra-therapeutic concentrations (geometric mean $C_{max}$ for 300 mg at steady-state multiplied by a factor of 2). In addition, the bias-corrected two-sided 90% confidence interval of the Delta QTc distribution was determined using the boot package in R (boot( ) function), where an additional nonparametric bootstrap was performed. If the upper limit of the 90% confidence interval was <10 msec, then an effect of Formulation D on QTc was to be ruled out.

Changes in QTc (largest to smallest effect) were associated with age (+16.8 msec increase in a 70-year old compared to an 18-year old subject), central vs. non-central reading (−8.4 msec), sex (+7.6 msec in females), methadone (+6.1 msec), barbiturates (+5.0 msec), phencyclidine (+3.4 msec), hydroxyzine and cocaine (+1.7 msec each), Holter vs. non-Holter (−1.7 msec), oxycodone (−1.5 msec), and codeine (+1.3 msec). Alpha was affected by COWS scores only, with an alpha of 0.341 for a COWS score of 5 and 0.363 for a COWS score of 20, respectively. The mean, median, and 90% confidence intervals for the geometric mean $C_{max}$ and delta QTc and the bias corrected 90% confidence intervals for delta QTc are summarized below for therapeutic and supra-therapeutic concentrations of Formulation D.

TABLE 13

| Dose | Geometric Mean $C_{max}$ (ng/mL) | | | Delta QTc (msec) | | | |
|---|---|---|---|---|---|---|---|
| | Mean | Median | 90% Confidence Interval | Mean | Median | 90% Confidence Interval | Bias-Corrected 90% Confidence Interval |
| Formulation D100 Q28D | 3.44 | 3.43 | 3.25 to 3.63 | −0.1 | −0.16 | −0.65 to 0.29 | −0.65 to 0.29 |
| Formulation D300 Q28D | 8.12 | 8.12 | 7.54 to 8.72 | −0.40 | −0.38 | −1.52 to 0.66 | −1.52 to 0.67 |
| 2 x Formulation D300 Q28D | 16.2 | 16.2 | 15.1 to 17.4 | −0.79 | −0.75 | −30.4 to 1.32 | −3.05 to 1.34 |

The results demonstrate that Formulation D at therapeutic doses of 100 mg and 300 mg and at a supra-therapeutic dose of 600 mg did not have an effect on QT, after accounting for the covariates that may influence heart rate and QT in subjects with opioid use disorder.

Example 7

As discussed above, a pivotal Phase 3 double-blind (Ph3DB) trial demonstrated that 2 doses of Formulation D300 followed by 4 doses of Formulation D300 or Formulation D100 (the 300/300 mg and 300/100 mg dosing regimens, respectively) at monthly intervals led to significantly greater percentage abstinence from opioids in subjects with moderate or severe opioid use disorder (OUD) compared with placebo). An additional observation from the Ph3DB study was that the subgroup of injection drug patients achieved higher percentage abstinence at Week 24 with the 300/300 mg regimen compared with the 300/100 mg regimen (54% vs 32%, RR=1.7, 95% CI 1.2-2.4). Exploratory analyses determined that the percentage of injection drug patients who remained abstinent for the last 4 weeks of the 24-week treatment period, when differences in buprenorphine plasma concentrations between the 2 dosing regimens were the greatest, was higher with the 300/300 mg group than the 300/100 mg group (34% vs 18%).

This study is designed to compare the efficacy, safety and tolerability of 2 maintenance doses of Formulation D300 and Formulation D100 every month, in treatment-seeking subjects with moderate to severe opioid use disorder predicted to benefit from the higher 300 mg maintenance dose. The study will also evaluate initiation of treatment with Formulation D without a period of SUBOXONE® titration. The study will enroll injection drug patients (e.g., those with an average of 5 or more days of opioid injections per week in the previous 90 days). Subjects with no documented prior medical treatment with buprenorphine will first receive 1 or more doses of SUBOXONE® prior to Formulation D; subjects with documented prior medical treatment with buprenorphine will not receive SUBOXONE® prior to Formulation D. Subjects will receive 2 doses of Formulation D300 at a monthly interval, and will then be randomly assigned to receive Formulation D300 (300/300 mg regimen) or Formulation D100 (300/100 mg regimen) for an additional 11 monthly maintenance doses. Subjects will receive manual-guided counselling and psychosocial support throughout the treatment period.

After receiving two Formulation D300 doses given 1 month apart, approximately 432 injection drug patients will be randomized immediately prior to their third monthly injection of Formulation D at a 1:1 ratio to receive either Formulation D300 or Formulation D100 in order to achieve 90% power for detecting a 12.5% difference in the primary endpoint (i.e., percentage of abstinence for opioid use by subjects).

The primary endpoint will be the percentage of negative urine drug screens for illicit opioid use by injection drug patients over Weeks 21 to 52, based on 20 planned urine drug screen assessments (9 scheduled and 11 random), where missing urine drug screen assessments will be considered positive for opioid use.

The five secondary endpoints will include: (1) the percentage of subjects with ≥75% negative urine drug screens for illicit opioid use over Weeks 21 to 52 based on 20 planned urine drug screen assessments (9 scheduled and 11 random), where missing urine drug screen assessments will be considered as positive for opioid use; (2) the percentage of weeks with ≤3 days illicit opioid use via the injection route by subjects, based on daily self-report via IVR platform, over Weeks 21 to 52, by subject, where any missing daily self-report of opioid use will be considered as positive for opioid use via the injection route; (3) the percentage of weeks with ≤3 days illicit opioid use via any route by subjects, based on daily self-report via IVR platform, over Weeks 21 to 52, by subject, where any missing daily self-report of opioid use via any route will be considered as positive for opioid use via the injection route; (4) the percentage of subjects with 100% weeks of abstinence over Weeks 49 to 52, based on urine drug screen assessments (2 scheduled and 2 random), where missing urine drug screen assessments will be considered as positive for opioid use; and (5) the time from randomization to study discontinuation.

The ten exploratory assessments will include: (1) the total scores on opioid craving VAS, the COWS and Subjective Opioid Withdrawal Scale (SOWS) during the treatment period; (2) the number and percentage of urine samples positive for other substances of abuse during the treatment period; (3) the percentage of daily self-reports negative for opioid use (via all routes) over Weeks 21 to 52, by subject; (4) the percentage of daily self-reports negative for opioid use via injection route over Weeks 21 to 52, by subject; (5) the health-related quality of life (HRQoL) as measured by the Medical Outcomes Study Short-Form 36-Item Questionnaire, Version 2 (SF-36v2); (6) the treatment effectiveness as assessed by the Treatment Effectiveness Assessment (TEA); (7) the medication satisfaction as assessed by the Medication Satisfaction Questionnaire (MSQ); (8) the HIV risk behaviors as measured by the HIV Risk Behavior Survey (HRBS); (9) the employment and productivity as measured by the Work Productivity and Activity Impairment Questionnaire: Specific Health Problem (WPAI:SHP v2.0); and (10) the healthcare resource utilization (HCRU) and health insurance as assessed by custom forms.

Eligible subjects with no prior exposure to buprenorphine will be administered a test dose of 4 mg/1 mg of SUBOXONE® in the treatment clinic, followed by a 1 hour wait. Formulation D can be administered if the subject exhibits no allergic reaction to SUBOXONE®, if the subject exhibits no significant withdrawal signs/symptoms (e.g., their COWS score ≤12), and subjects report that they have not used opioids for at least 6 hours.

Subjects with a COWS score >12 and significant withdrawal signs/symptoms will be started on an initial dose of 8 mg/2 mg SUBOXONE®, and may be titrated upwards in 4-8 mg/1-2 mg increments, if COWS score is still >12, at approximately 1 to 2-hour intervals, under supervision in a treatment clinic to a total dose of up to 24 mg/6 mg of SUBOXONE® based on COWS score and the control of acute withdrawal signs/symptoms on SUBOXONE® Day 1. If a COWS score of ≤12 is achieved with no significant withdrawal signs/symptoms, subjects may receive the first dose of Formulation D. Subjects with a COWS score of >12 and reporting withdrawal signs/symptoms overnight will be continued on SUBOXONE® Day 2. Subjects will receive a dose of SUBOXONE® equal to the total dose given on SUBOXONE® Day 1, plus additional 4-8 mg/1-2 mg increments at 1-2-hour intervals (if COWS score is still >12) to a maximum dosage of 24 mg/6 mg based on COWS scores and the control of acute withdrawal signs/symptoms. If a COWS score of ≤12 is achieved with no significant withdrawal signs/symptoms, subjects may receive the first dose of Formulation D. The SUBOXONE® dosing regimen may be administered for a maximum of 2 days at a maximum daily dosage of 24 mg/6 mg based on COWS scores and control of acute withdrawal signs/symptoms, as well as physician judgment.

The second dose of Formulation D will be administered 1 month later. Subjects able to continue treatment will be randomized in a 1:1 ratio at Week 9 to receive maintenance doses of either Formulation D300 or Formulation D100 every month for a total of up to 11 maintenance injections. Randomization prior to the third dose of Formulation D will be stratified according to the number of previous treatments with MAT (no prior MAT vs. at least one prior MAT) and race (African American vs. Non-African American).

Following the first injection of Formulation D, all subjects will be contacted daily via an Interactive Voice Response (IVR) system to assess their opioid use that day (frequency and route). Subjects will return to the clinic for weekly urine drug screens for approximately 5 months (corresponding to Week 1 to Week 20). From the sixth monthly injection until the end of the treatment period (corresponding to Week 21 to Week 52), urine drug screens will be obtained at each monthly clinic visit for an injection of Formulation D, with 1 or 2 additional random urine drug screens per month. All subjects will receive manual-guided counselling and psychosocial support throughout the treatment period from Day 1 through the end of the treatment period, All subjects will continue study treatment until they complete Visit 15 (Week 51/End of Treatment (EOT) or prematurely discontinue treatment for another reason. During the EOT visit, the Investigator or a medically qualified sub-investigator will discuss available treatment options. an end-of-study (EOS) visit (or at 30 days after the last dose of study treatment, if prematurely discontinued) followed by a phone call twice every month for an additional 3 months, will capture follow-up information regarding adverse events (AEs) at EOT and the occurrence of new AEs since the EOT. Subjects who stop treatment prematurely will be encouraged to continue to attend clinic visits to complete any remaining follow-up assessments.

The study will demonstrate that the injection drug patients treated with the 300/300 mg dosing regimen will achieve a higher percentage of negative urine drug screens for illicit opioid use over Weeks 21-52 than those injection drug patients treated with the 300/100 mg dosing regimen.

While various embodiments and aspects are shown and described herein, it will be clear to the skilled artisan that such embodiments and aspects are provided by way of example. Variations, changes, and substitutions will occur to the skilled artisan. It will be understood that various alternatives to the embodiments described herein can be used.

What is claimed is:

1. A method of treating moderate-to-severe opioid use disorder in an injection drug patient in need thereof, the method comprising subcutaneously administering a buprenorphine composition once per month for at least six months to the injection drug patient; wherein the buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone.

2. The method of claim 1, comprising subcutaneously administering the buprenorphine composition once per month for at least twelve months.

3. The method of claim 1, wherein the method produces opioid abstinence in the injection drug user.

4. A method of treating opioid use disorder in an injection drug patient in need thereof, the method comprising subcutaneously administering a buprenorphine composition once per month for at least six months to the injection drug patient; wherein the buprenorphine composition comprises about 300 mg buprenorphine free base, a poly(lactide-co-glycolide) copolymer, and N-methyl-2-pyrrolidone.

5. The method of claim 4, wherein the opioid use disorder is moderate-to-severe opioid use disorder.

6. The method of claim 4, wherein the opioid use disorder is moderate opioid use disorder.

7. The method of claim 4, wherein the opioid use disorder is severe opioid use disorder.

8. The method of claim 4, wherein the buprenorphine composition comprises: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone.

9. The method of claim 4, wherein the buprenorphine composition comprises: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone.

10. The method of claim 4, wherein the buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone.

11. The method of claim 4, comprising subcutaneously administering the buprenorphine composition once per month for at least twelve months.

12. The method of claim 4, wherein the method produces opioid abstinence in the injection drug user.

13. The method of claim 4, wherein the method of treating opioid use disorder is a method for reducing opioid craving.

14. The method of claim 4, wherein the method of treating opioid use disorder is a method for eliminating opioid craving.

15. The method of claim 4, wherein the method of treating opioid use disorder is a method for reducing opioid withdrawal symptoms.

16. The method of claim 4, wherein the method of treating opioid use disorder is a method for eliminating opioid withdrawal symptoms.

17. The method of claim 4, wherein the method of treating opioid use disorder is a method for reducing illicit opioid use.

18. The method of claim 4, wherein the method of treating opioid use disorder is a method for eliminating illicit opioid use.

19. The method of claim 4, wherein the injection drug patient is an intravenous injection drug patient; an intramuscular injection drug patient; or a subcutaneous injection drug patient.

20. A method of treating opioid use disorder in an injection drug patient in need thereof, the method comprising subcutaneously administering a buprenorphine composition once per month to the injection drug patient; wherein the buprenorphine composition comprises about 300 mg buprenorphine free base, a poly(lactide-co-glycolide) copolymer, and N-methyl-2-pyrrolidone.

21. The method of claim 20, wherein the opioid use disorder is moderate-to-severe opioid use disorder.

22. The method of claim 20, wherein the opioid use disorder is moderate opioid use disorder.

23. The method of claim 20, wherein the opioid use disorder is severe opioid use disorder.

24. The method of claim 20, wherein the buprenorphine composition comprises: (i) about 300 mg buprenorphine free base at about 10 wt % to about 30 wt %; (ii) about 10 wt % to about 60 wt % of a poly(DL-lactide-co-glycolide) copolymer; and (iii) about 30 wt % to about 70 wt % of N-methyl-2-pyrrolidone.

25. The method of claim 24, wherein the buprenorphine composition comprises: (i) about 300 mg buprenorphine free base at about 14 wt % to about 22 wt %; (ii) about 22 wt % to about 42 wt % of a poly(DL-lactide-co-glycolide) copolymer; and (iii) about 40 wt % to about 60 wt % of N-methyl-2-pyrrolidone.

26. The method of claim 25, wherein the buprenorphine composition comprises: (i) about 300 mg buprenorphine free base at 18 wt %; (ii) about 32 wt % of a poly(DL-lactide-co-glycolide) copolymer; and (iii) about 50 wt % of N-methyl-2-pyrrolidone.

27. The method of claim 20, wherein the buprenorphine composition comprises: (i) about 300 mg buprenorphine free base at about 10 wt % to about 30 wt %; (ii) about 10 wt % to about 60 wt % of a 50:50 to 95:5 poly(DL-lactide-co-glycolide) copolymer having a weight average molecular weight of about 5,000 Daltons to about 40,000 Daltons; and (iii) about 30 wt % to about 70 wt % of N-methyl-2-pyrrolidone.

28. The method of claim 27, wherein the buprenorphine composition comprises: (i) about 300 mg buprenorphine free base at about 14 wt % to about 22 wt %; (ii) about 22 wt % to about 42 wt % of a 50:50 to 80:20 poly(DL-lactide-co-glycolide) copolymer having a weight average molecular weight of about 5,000 Daltons to about 30,000 Daltons; and (iii) about 40 wt % to about 60 wt % of N-methyl-2-pyrrolidone.

29. The method of claim 28, wherein the buprenorphine composition comprises: (i) about 300 mg buprenorphine free base at 18 wt %; (ii) about 32 wt % of a 50:50 poly(DL-lactide-co-glycolide) copolymer having a carboxy terminal group and a weight average molecular weight of about 9,000 Daltons to about 19,000 Daltons; and (iii) about 50 wt % of N-methyl-2-pyrrolidone.

* * * * *